United States Patent [19]
Canfield et al.

[11] Patent Number: 6,001,066
[45] Date of Patent: Dec. 14, 1999

[54] TYMPANIC THERMOMETER WITH MODULAR SENSING PROBE

[75] Inventors: Eric L. Canfield, Chester Springs; Edward P. Cheslock, Lincoln University, both of Pa.

[73] Assignee: Trutek, Inc., West Chester, Pa.

[21] Appl. No.: 09/089,417

[22] Filed: Jun. 3, 1998

Related U.S. Application Data

[60] Provisional application No. 60/048,752, Jun. 3, 1997.

[51] Int. Cl.⁶ .................................................. A61B 10/00
[52] U.S. Cl. ........................................................ 600/559
[58] Field of Search ................................... 600/549, 559; 374/121, 158

[56] References Cited

U.S. PATENT DOCUMENTS

| | | |
|---|---|---|
| Re. 34,507 | 1/1994 | Egawa et al. . |
| Re. 34,599 | 5/1994 | Susyznski et al. . |
| Re. 34,789 | 11/1994 | Fraden . |

(List continued on next page.)

FOREIGN PATENT DOCUMENTS

| | | |
|---|---|---|
| 66021/86 | of 0000 | Australia . |
| 778199 | 2/1972 | Belgium . |
| 1258052 | 8/1989 | Canada . |
| 1265355 | 2/1990 | Canada . |
| 1314407 | 3/1993 | Canada . |
| 0098402 | 1/1984 | European Pat. Off. . |
| 0445783A2 | 9/1991 | European Pat. Off. . |
| 0674162A2 | 9/1995 | European Pat. Off. . |
| 0715359A1 | 6/1996 | European Pat. Off. . |
| 2167973 | 8/1973 | France . |
| 2343234 | 9/1977 | France . |
| 4422974A1 | 1/1995 | Germany . |
| 19604201A1 | 8/1997 | Germany . |
| 55-154426 | 12/1980 | Japan . |
| 56-161134 | 12/1981 | Japan . |
| 56-167428 | 12/1981 | Japan . |
| 57-35739 | 2/1982 | Japan . |
| 57-35740 | 2/1982 | Japan . |
| 57-35741 | 2/1982 | Japan . |
| 57-212039 | 12/1982 | Japan . |
| 59-135439 | 9/1984 | Japan . |
| 60-187829 | 9/1985 | Japan . |

(List continued on next page.)

OTHER PUBLICATIONS

J. W. Moore et al., "Noncontact tympanic thermometer", *Medical & Biological Engineering & Computing*, vol. 16, No. 5, Sep. 1978, pp. 580–584.

(List continued on next page.)

Primary Examiner—Max Hindenburg
Attorney, Agent, or Firm—Nixon & Vanderhye P.C.

[57] ABSTRACT

A two-piece portable, self-contained tympanic thermometer temperature measuring system includes a measuring unit and a base unit. The measuring unit can be ergonomically designed as a compact, pencil-shaped, easy to hold unit that includes a removable sensing module that interfaces with the base unit and/or other host via digital signaling. All analog circuitry can be self-contained within the sensor module, and the sensing module circuitry components may be potted with thermally conductive epoxy to reduce variations due to differences in component temperatures. The sensing module casing may be made out of a conductor to provide electromagnetic field isolation. The sensing module can include a microcontroller that communicates with a microcontroller in the base unit via a removable modular 4-conductor telephone handset cord. The measuring unit preferably has the capability to measure the amount of pressure it is applying to the patient's ear—and thus, the ability to sense when it is in position and has sealed the patient's outer ear canal. Temperature measurement can be performed automatically and/or inhibited in response to this pressure sensing.

22 Claims, 34 Drawing Sheets

U.S. PATENT DOCUMENTS

| | | |
|---|---|---|
| D. 218,851 | 9/1970 | Sato . |
| D. 246,766 | 12/1977 | Everest . |
| D. 254,959 | 5/1980 | Everest . |
| D. 300,728 | 4/1989 | Ross . |
| D. 303,008 | 8/1989 | O'Hara et al. . |
| D. 317,414 | 6/1991 | Lanci et al. . |
| D. 318,812 | 8/1991 | Matsuura et al. . |
| D. 321,487 | 11/1991 | Manno . |
| D. 329,389 | 9/1992 | Hines . |
| D. 329,395 | 9/1992 | Mackay . |
| D. 329,396 | 9/1992 | Mackay . |
| D. 336,862 | 6/1993 | Ayton et al. . |
| D. 337,534 | 7/1993 | Swift . |
| D. 337,954 | 8/1993 | Makita et al. . |
| D. 338,412 | 8/1993 | Curbbun . |
| D. 342,681 | 12/1993 | Mackay . |
| D. 370,860 | 6/1996 | Pompei et al. . |
| 738,960 | 9/1903 | Vaughan et al. . |
| 1,363,259 | 12/1920 | Mills . |
| 2,696,117 | 12/1954 | Harrison . |
| 2,804,069 | 8/1957 | Schwamm et al. . |
| 2,844,031 | 7/1958 | Rosenthal . |
| 2,848,998 | 8/1958 | Bryan . |
| 2,877,500 | 3/1959 | Rainer et al. . |
| 2,904,480 | 9/1959 | Rainer et al. . |
| 2,969,141 | 1/1961 | Katzin . |
| 2,972,991 | 2/1961 | Burke . |
| 3,023,398 | 2/1962 | Siegert . |
| 3,054,397 | 9/1962 | Benzinger . |
| 3,156,117 | 11/1964 | Benzinger . |
| 3,179,805 | 4/1965 | Astheimer . |
| 3,190,436 | 6/1965 | Diamant . |
| 3,193,978 | 7/1965 | Bader . |
| 3,234,593 | 2/1966 | Lerner et al. . |
| 3,277,715 | 10/1966 | Vanderschmidt . |
| 3,282,106 | 11/1966 | Barnes . |
| 3,301,394 | 1/1967 | Baermann et al. . |
| 3,335,715 | 8/1967 | Hugenholtz et al. . |
| 3,349,896 | 10/1967 | Ensign et al. . |
| 3,367,186 | 2/1968 | Ensign et al. . |
| 3,368,076 | 2/1968 | Clifford . |
| 3,465,149 | 9/1969 | Flint . |
| 3,469,449 | 9/1969 | Keller . |
| 3,469,685 | 9/1969 | Baermann . |
| 3,491,596 | 1/1970 | Dean . |
| 3,500,280 | 3/1970 | Ensign . |
| 3,507,153 | 4/1970 | Jones et al. . |
| 3,526,135 | 9/1970 | Wortz . |
| 3,531,642 | 9/1970 | Barnes et al. . |
| 3,531,992 | 10/1970 | Moore . |
| 3,581,570 | 6/1971 | Wortz . |
| 3,605,750 | 9/1971 | Sheridan et al. . |
| 3,626,757 | 12/1971 | Benzinger . |
| 3,641,345 | 2/1972 | Coackley et al. . |
| 3,650,153 | 3/1972 | Schwab . |
| 3,653,263 | 4/1972 | Poole et al. . |
| 3,663,917 | 5/1972 | Mahmoodi . |
| 3,673,868 | 7/1972 | Beury, III et al. . |
| 3,678,751 | 7/1972 | Mead et al. . |
| 3,681,991 | 8/1972 | Eberly, Jr. . |
| 3,701,347 | 10/1972 | Belkin . |
| 3,703,892 | 11/1972 | Meyers . |
| 3,719,396 | 3/1973 | VanDeWalker et al. . |
| 3,724,448 | 4/1973 | Lima . |
| 3,729,998 | 5/1973 | Mueller et al. . |
| 3,735,864 | 5/1973 | Eckhart . |
| 3,738,172 | 6/1973 | Sato . |
| 3,738,173 | 6/1973 | Sato . |
| 3,738,479 | 6/1973 | Sato . |
| 3,738,892 | 6/1973 | Curcio . |
| 3,742,191 | 6/1973 | Poole et al. . |
| 3,750,471 | 8/1973 | Bremer . |
| 3,777,568 | 12/1973 | Risgin et al. . |
| 3,781,748 | 12/1973 | Bishop et al. . |
| 3,781,837 | 12/1973 | Anderson et al. . |
| 3,798,366 | 3/1974 | Hunt et al. . |
| 3,809,228 | 5/1974 | Fowler et al. . |
| 3,809,229 | 5/1974 | Wahlig . |
| 3,809,920 | 5/1974 | Cohen et al. . |
| 3,812,847 | 5/1974 | Moore et al. . |
| 3,812,897 | 5/1974 | Latinen . |
| 3,822,593 | 7/1974 | Oudewaal . |
| 3,822,598 | 7/1974 | Brothers et al. . |
| 3,832,669 | 8/1974 | Mueller et al. . |
| 3,833,115 | 9/1974 | Schapker . |
| 3,834,238 | 9/1974 | Mueller et al. . |
| 3,838,600 | 10/1974 | Ersek et al. . |
| 3,849,530 | 11/1974 | Wyeth et al. . |
| 3,851,029 | 11/1974 | Cornett, III et al. . |
| 3,878,836 | 4/1975 | Twentier . |
| 3,880,282 | 4/1975 | Naumann . |
| 3,929,018 | 12/1975 | Turner . |
| 3,942,891 | 3/1976 | Spielberger et al. . |
| 3,949,740 | 4/1976 | Twentier . |
| 3,987,899 | 10/1976 | Vyprachticky . |
| 3,999,434 | 12/1976 | Yen . |
| 3,999,537 | 12/1976 | Noiles . |
| 4,005,605 | 2/1977 | Michael . |
| 4,022,855 | 5/1977 | Hamblen . |
| 4,024,397 | 5/1977 | Weiner . |
| 4,054,057 | 10/1977 | Kluge . |
| 4,061,226 | 12/1977 | Essen . |
| 4,062,239 | 12/1977 | Fowler et al. . |
| 4,081,678 | 3/1978 | Macall . |
| 4,091,922 | 5/1978 | Egler . |
| 4,117,926 | 10/1978 | Turner et al. . |
| 4,148,304 | 4/1979 | Mull . |
| 4,159,766 | 7/1979 | Kluge . |
| 4,166,389 | 9/1979 | Montren . |
| 4,166,454 | 9/1979 | Meijer . |
| 4,168,626 | 9/1979 | Fullager . |
| 4,183,248 | 1/1980 | West . |
| 4,191,197 | 3/1980 | Benzinger . |
| 4,193,396 | 3/1980 | Wacker . |
| 4,197,944 | 4/1980 | Catlin . |
| 4,201,222 | 5/1980 | Haase . |
| 4,226,910 | 10/1980 | Dahlen et al. . |
| 4,233,512 | 11/1980 | Rupert . |
| 4,241,828 | 12/1980 | Bourdelle et al. . |
| 4,271,358 | 6/1981 | Schwarz . |
| 4,275,591 | 6/1981 | Wand . |
| 4,297,685 | 10/1981 | Brainard, II . |
| 4,301,682 | 11/1981 | Everest . |
| 4,312,357 | 1/1982 | Andersson et al. . |
| 4,315,150 | 2/1982 | Darringer et al. . |
| 4,341,992 | 7/1982 | Goldstein . |
| 4,343,182 | 8/1982 | Pompei . |
| 4,343,185 | 8/1982 | Knute . |
| 4,350,166 | 9/1982 | Mobarry . |
| 4,351,616 | 9/1982 | Farnstrom et al. . |
| 4,362,166 | 12/1982 | Furler et al. . |
| 4,372,690 | 2/1983 | Berman et al. . |
| 4,378,489 | 3/1983 | Chabinsky et al. . |
| 4,379,971 | 4/1983 | Smith et al. . |
| 4,380,998 | 4/1983 | Kieffer, III et al. . |
| 4,392,005 | 7/1983 | Mohrman . |
| 4,400,341 | 8/1983 | Sorensen . |
| 4,414,980 | 11/1983 | Mott . |
| 4,420,265 | 12/1983 | Everest et al. . |
| 4,425,921 | 1/1984 | Fujisaki et al. . |
| 4,433,924 | 2/1984 | Quinn, III . |
| 4,436,438 | 3/1984 | Voznick . |

6,001,066
Page 3

| | | |
|---|---|---|
| 4,454,370 | 6/1984 | Viznick . |
| 4,456,390 | 6/1984 | Junkert et al. . |
| 4,457,633 | 7/1984 | Andrews . |
| 4,471,354 | 9/1984 | Smith . |
| 4,475,554 | 10/1984 | Hyndman . |
| 4,481,417 | 11/1984 | Inglee . |
| 4,487,208 | 12/1984 | Kamens . |
| 4,493,564 | 1/1985 | Epstein . |
| 4,494,881 | 1/1985 | Everest . |
| 4,509,522 | 4/1985 | Manuccia et al. . |
| 4,510,115 | 4/1985 | Gokcen et al. . |
| 4,515,165 | 5/1985 | Carroll . |
| 4,524,779 | 6/1985 | Brown, Jr. . |
| 4,527,896 | 7/1985 | Irani et al. . |
| 4,536,851 | 8/1985 | Germanton et al. . |
| 4,537,791 | 8/1985 | Tarjan . |
| 4,566,808 | 1/1986 | Pompei et al. . |
| 4,572,365 | 2/1986 | Bruno et al. . |
| 4,588,306 | 5/1986 | Burger et al. . |
| 4,602,642 | 7/1986 | O'Hara et al. . |
| 4,607,963 | 8/1986 | Ulrickson . |
| 4,614,442 | 9/1986 | Poncy . |
| 4,619,271 | 10/1986 | Burger et al. . |
| 4,626,686 | 12/1986 | Pompei et al. . |
| 4,634,294 | 1/1987 | Christol et al. . |
| 4,636,091 | 1/1987 | Pompei et al. . |
| 4,644,163 | 2/1987 | Selander . |
| 4,652,145 | 3/1987 | Bjornberg . |
| 4,659,234 | 4/1987 | Brouwer . |
| 4,662,360 | 5/1987 | O'Hara et al. . |
| 4,679,949 | 7/1987 | Sakamoto . |
| 4,684,018 | 8/1987 | Jarund . |
| 4,691,712 | 9/1987 | Brown, Jr. . |
| 4,727,500 | 2/1988 | Jackson et al. . |
| 4,763,522 | 8/1988 | Pompei . |
| 4,765,752 | 8/1988 | Beynon et al. . |
| 4,784,149 | 11/1988 | Berman et al. . |
| 4,790,324 | 12/1988 | O'Hara et al. . |
| 4,797,840 | 1/1989 | Fraden . |
| 4,801,212 | 1/1989 | Imura . |
| 4,823,949 | 4/1989 | Bala . |
| 4,831,258 | 5/1989 | Paulk et al. . |
| 4,854,730 | 8/1989 | Fraden . |
| 4,859,079 | 8/1989 | Wickersheim et al. . |
| 4,863,281 | 9/1989 | Suszynski . |
| 4,874,253 | 10/1989 | Pompei et al. . |
| 4,895,164 | 1/1990 | Wood . |
| 4,900,162 | 2/1990 | Beckman et al. . |
| 4,907,895 | 3/1990 | Everest . |
| 4,911,559 | 3/1990 | Meyst et al. . |
| 4,914,673 | 4/1990 | Imura . |
| 4,919,505 | 4/1990 | Bartosiak et al. . |
| 4,932,789 | 6/1990 | Egawa et al. . |
| 4,955,980 | 9/1990 | Masuo . |
| 4,986,672 | 1/1991 | Beynon . |
| 4,993,419 | 2/1991 | Pompei et al. . |
| 4,993,424 | 2/1991 | Suszysnki et al. . |
| 5,001,657 | 3/1991 | Yagura et al. . |
| 5,011,296 | 4/1991 | Bartosiak et al. . |
| 5,012,813 | 5/1991 | Pompei et al. . |
| 5,017,018 | 5/1991 | Iuchi et al. . |
| 5,017,019 | 5/1991 | Pompei . |
| 5,018,872 | 5/1991 | Suszynski et al. . |
| 5,024,533 | 6/1991 | Egawa et al. . |
| 5,031,619 | 7/1991 | Pompei . |
| 5,046,482 | 9/1991 | Everest . |
| 5,051,590 | 9/1991 | Kern et al. . |
| 5,051,595 | 9/1991 | Kern et al. . |
| 5,054,936 | 10/1991 | Fraden . |
| 5,056,682 | 10/1991 | Meyst et al. . |
| 5,066,142 | 11/1991 | DeFrank et al. . |
| 5,081,359 | 1/1992 | Pompei . |
| 5,081,998 | 1/1992 | Yelderman et al. . |
| 5,088,834 | 2/1992 | Howe et al. . |
| 5,094,544 | 3/1992 | Ignatowicz . |
| 5,127,742 | 7/1992 | Fraden . |
| 5,150,969 | 9/1992 | Goldberg et al. . |
| 5,153,563 | 10/1992 | Goto et al. . |
| 5,159,936 | 11/1992 | Yelderman et al. . |
| 5,163,418 | 11/1992 | Fraden et al. . |
| 5,167,235 | 12/1992 | Seacord et al. .......................... 600/549 |
| 5,169,235 | 12/1992 | Tominaga et al. . |
| 5,172,978 | 12/1992 | Nomura et al. . |
| 5,178,464 | 1/1993 | Fraden . |
| 5,179,936 | 1/1993 | O'Hara et al. . |
| 5,183,337 | 2/1993 | Pompei . |
| 5,188,459 | 2/1993 | Mino et al. . |
| 5,199,436 | 4/1993 | Pompei et al. . |
| 5,229,612 | 7/1993 | Pompei et al. . |
| 5,232,284 | 8/1993 | Egawa et al. . |
| 5,264,375 | 11/1993 | Bang et al. . |
| 5,271,407 | 12/1993 | Pompei et al. . |
| 5,292,347 | 3/1994 | Pompei . |
| 5,293,862 | 3/1994 | O'Hara et al. . |
| 5,293,877 | 3/1994 | O'Hara et al. . |
| 5,313,951 | 5/1994 | Zhao . |
| 5,319,202 | 6/1994 | Pompei . |
| 5,325,863 | 7/1994 | Pompei . |
| 5,333,784 | 8/1994 | Pompei . |
| 5,340,215 | 8/1994 | Makita et al. .......................... 600/549 |
| 5,352,038 | 10/1994 | Schmidt et al. . |
| 5,352,039 | 10/1994 | Barral et al. . |
| 5,358,333 | 10/1994 | Schmidt et al. . |
| 5,368,038 | 11/1994 | Fraden . |
| 5,381,796 | 1/1995 | Pompei . |
| 5,388,907 | 2/1995 | Aoyama et al. . |
| 5,391,001 | 2/1995 | Rupert et al. . |
| 5,404,126 | 4/1995 | Mori et al. . |
| 5,411,032 | 5/1995 | Esseff et al. . |
| 5,445,158 | 8/1995 | Pompei . |
| 5,458,121 | 10/1995 | Harada . |
| 5,469,855 | 11/1995 | Pompei et al. . |
| 5,479,931 | 1/1996 | Mooradian . |
| 5,487,607 | 1/1996 | Mikata et al. .......................... 600/549 |
| 5,515,847 | 5/1996 | Braig et al. . |
| 5,516,010 | 5/1996 | O'Hara et al. . |
| 5,522,662 | 6/1996 | Shiokawa . |
| 5,528,041 | 6/1996 | Pompei . |
| 5,609,564 | 3/1997 | Makita et al. . |
| 5,619,195 | 4/1997 | Allen et al. .............................. 347/20 |
| 5,645,350 | 7/1997 | Tang . |

FOREIGN PATENT DOCUMENTS

| | | |
|---|---|---|
| 100319 | 6/1987 | Japan . |
| 147818 | 11/1962 | U.S.S.R. . |
| 1425765 | 2/1976 | United Kingdom . |
| 1518521 | 7/1978 | United Kingdom . |
| WO96/19938 | 7/1986 | WIPO . |
| WO93/03666 | 3/1993 | WIPO . |
| WO93/19662 | 10/1993 | WIPO . |
| WO95/14913 | 6/1995 | WIPO . |
| WO95/18961 | 7/1995 | WIPO . |
| WO96/07877 | 3/1996 | WIPO . |

OTHER PUBLICATIONS

D. E. Lees et al., "Noninvasive Determination of Core Temperature During Anesthesia", *Southern Medical Journal,* vol. 73, No. 10, Oct. 1980, pp. 1322–1324.

J. Fraden et al., "Application of Pyro–electric Polymer Film to Medical Thermometry," *Proceedings of the Eighth Annual Conference of the IEEE/Engineering in Medicine and Biology Society,* 86CH2368.9, vol. 3 of 3, Fort Worth, Texas, Nov. 7–10, 1986.

J. Fraden, "Application of Piezo/Pyroelectric Films in Medical Transducers," *Journal of Chemical Engineering,* vol. 13, No. 3, Mar./Apr. 1988, pp. 133–138.

J.M. Looney, Jr. et al., "Ear Thermometry," *Medical Electronics,* Jun. 1989.

M. Benzinger et al., "Tympanic Clinical Temperature," presented at the Fifth Symposium on Temperature, Washington, D.C., Jun. 21–24, 1971, sponsored by the National Bureau of Standards, American Institute of Physics, and Instrument Society of America.

Information Sheet, Model 1M, Thermopile Detector, Dexter Research Center, 2 pages, Oct. 1980, Michigan.

Information Sheet, Model 2M, Thermopile Detector, Dexter Research Center, 2 pages, Oct. 1980, Michigan.

Information Sheet, Model M5, Thermopile Detector, Dexter Research Center, 2 pages, Oct. 1980, Michigan.

Information Sheet, Model DR26, Dual Element Thermopile Detector, Dexter Research Center, 3 pages, Oct. 1980, Michigan.

Information Sheet, Model DR46, Thermopile Detector, Dexter Research Center, 1 page, Oct. 1979, Michigan.

Information Sheet, Model 1010, Low Noise Amplifier, Dexter Research Center, 2 pages, Oct. 1980, Michigan.

Dexter Research Center, Inc., Product Price List—Domestic, Jan. 1, 1983.

Y. Houdas, et al., "Human Body Temperature, Its Measurement and Regulation," p. 83, Plemum Press, New York and London.

Advertisement, "Optical Calibration," Det Tronics, Sunnyvale, CA, *In Tech,* p. 48, Oct. 1987.

P. Gaudet, "Omega Tympanic Infrared Temperature Measuring Instrument, Product Specification," Exergen Corporation, pp. 1–3.

ASTM Designation: E 1112–86 (Reapproved 1991), "Standard Specification for Electronic Thermometer for Intermittent Determination of Patient Temperature," pp. 1–4 (Reprinted from the Annual Book of ASTM Standards, Philadelphia, PA).

"Electronic Thermometers," *Medical Electronics,* Jun. 1996, pp. 118–120.

Schieferdecker, J., et al., "Infrared thermopile sensors with high sensitivity and very low temperature coefficient," *Sensors and Actuators* A 46–47 (1995) 422–427 (printed in the Netherlands).

P.C. Lanchester, "Digital thermometer circuit for silicon diode sensors," *Cryogenics* 1989 vol. 29 Dec., (Received May 30, 1989), Southampton, UK, pp. 1156–1159.

Trial Exhibit list from Thermoscan, Inc. V. Sherwood Medical Co.

Standard Specification for Infrared Thermometers for Intermittent Determination of Patient Temperature, ASTM Designation: EXXXX–97 (May 9, 1997).

Intelligent Medical Systems, Inc. FirstTemp Thermometer Model #2000A.

Sherwood Medical FirstTemp Genius Model #3000A.

Ivac Core Check Model #2090.

Diatek Insta–Temp Model #9000.

Thermoscan, Inc. Instant Thermometer Pro–1 Model #IR–1A.

Exergen Corporation LighTouch LTX Infrared Thermometer Model #LTX–1.

Exergen Corporation LighTouch.

Omron Gentle Temp Model #MC–502.

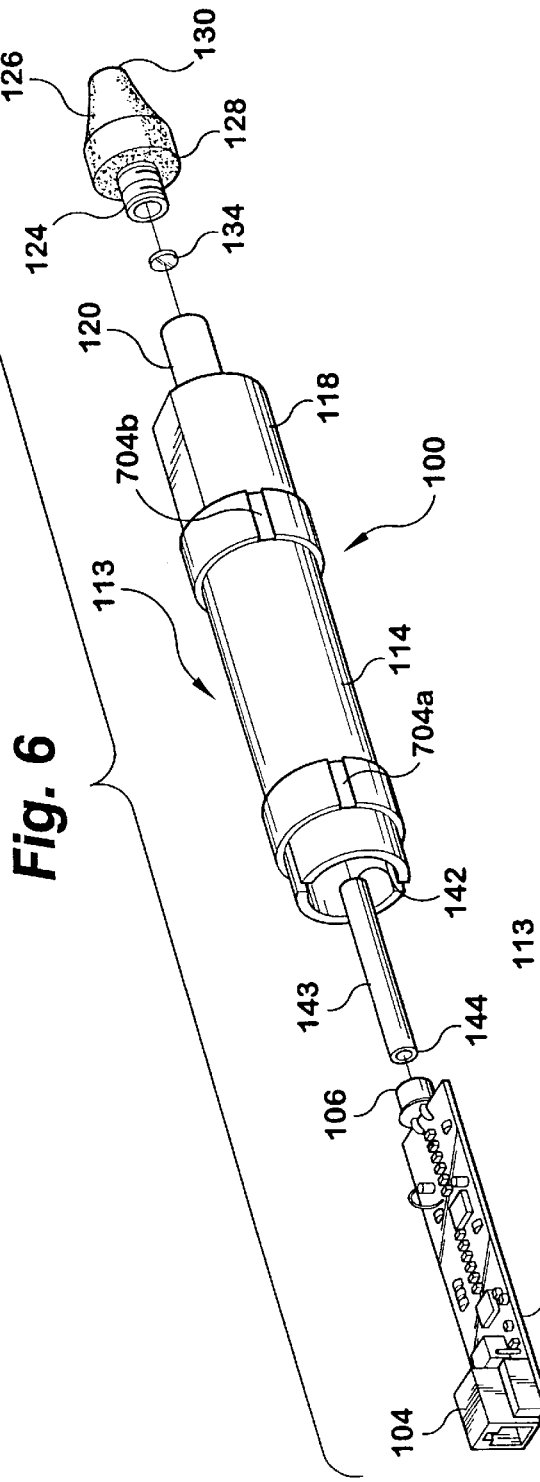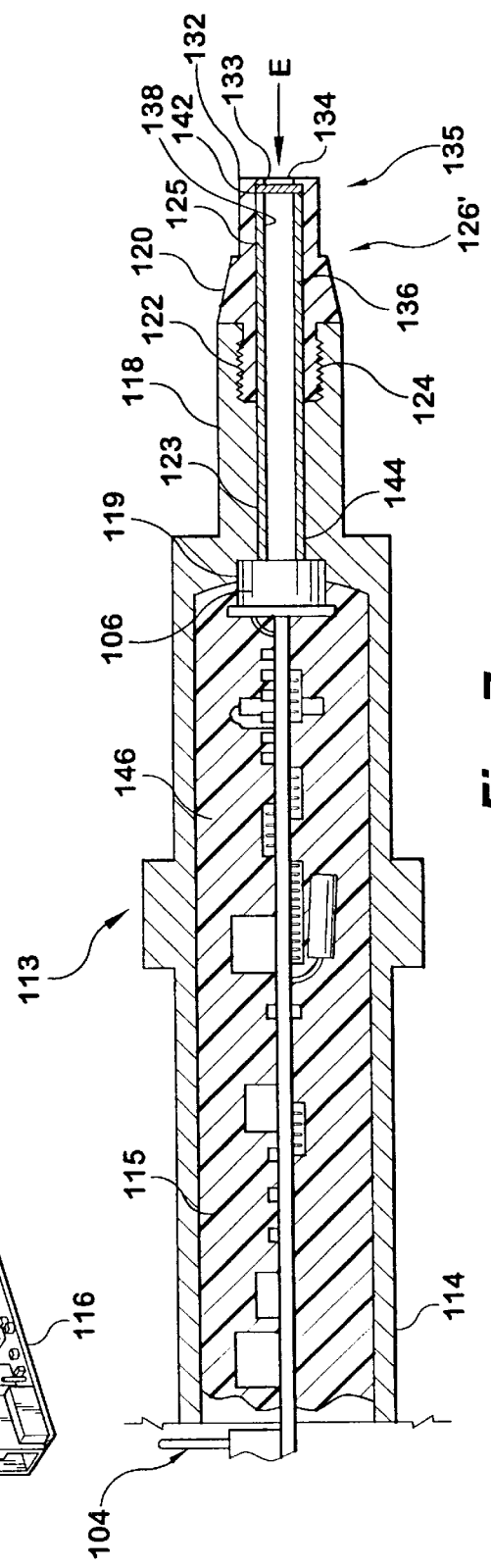

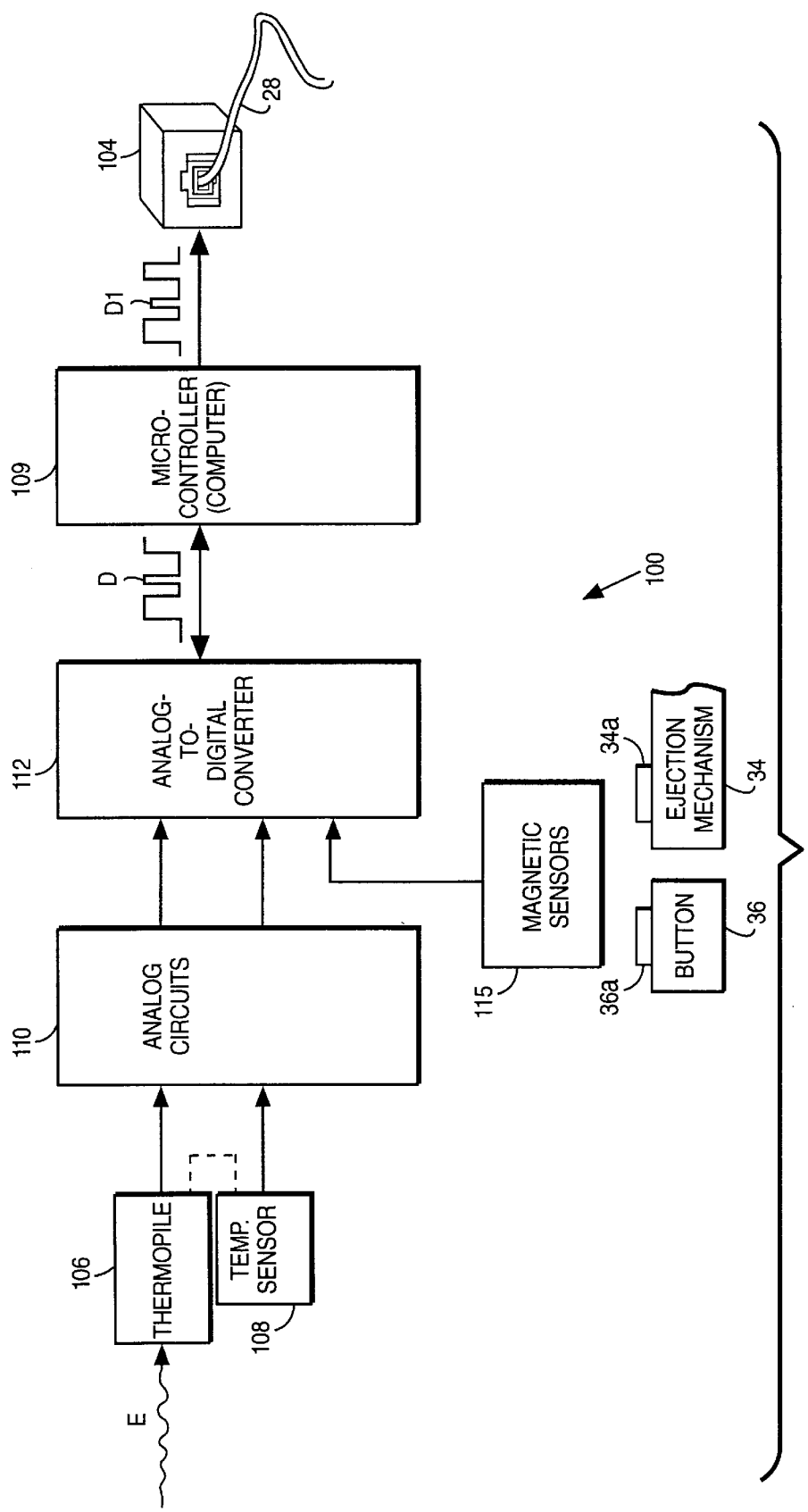
Fig. 10 SIMPLIFIED BLOCK DIAGRAM

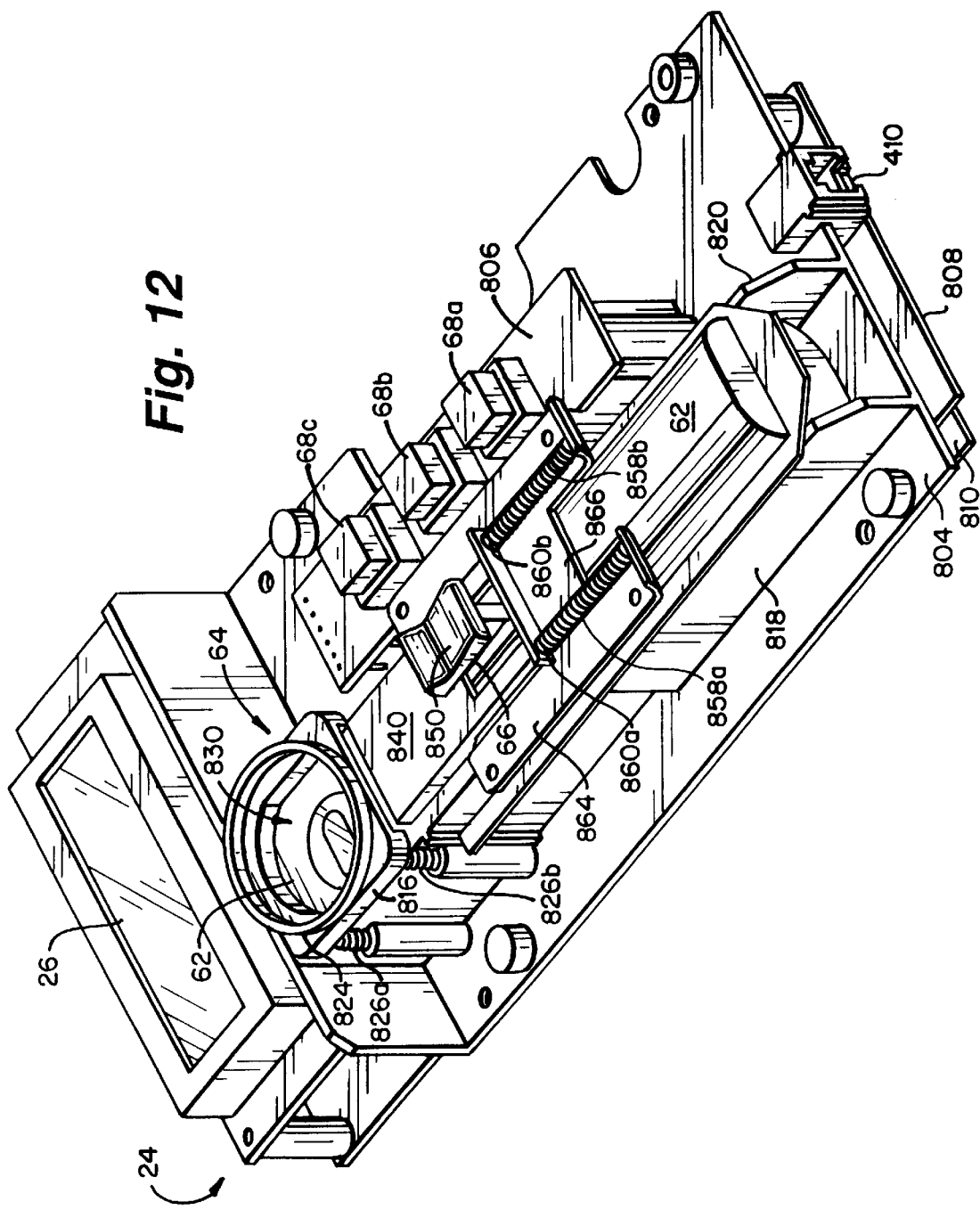

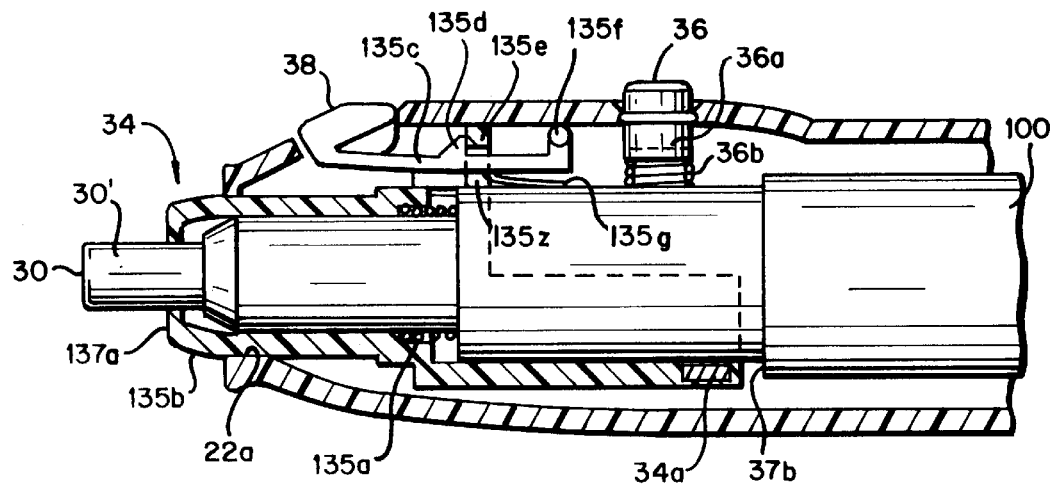
*Fig. 21A* LATCHED
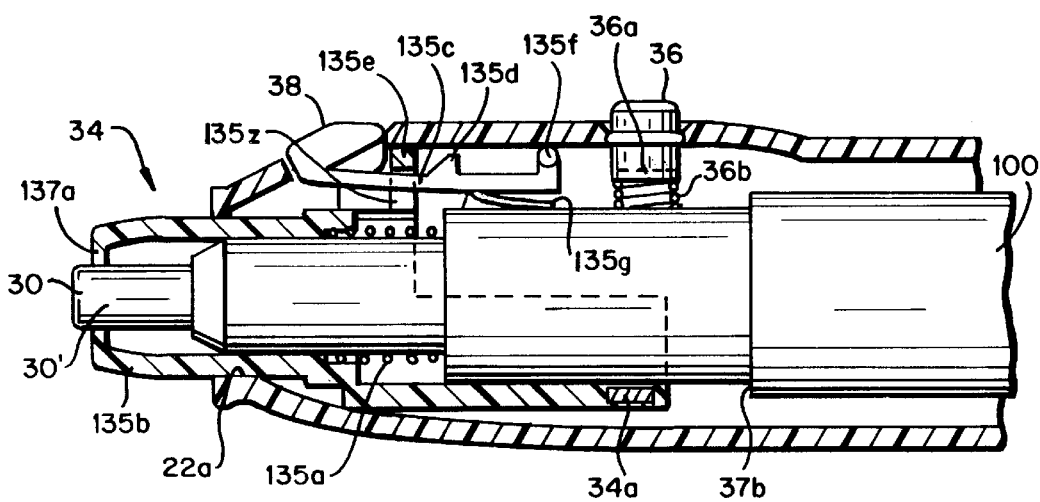
*Fig. 21B* UNLATCHED

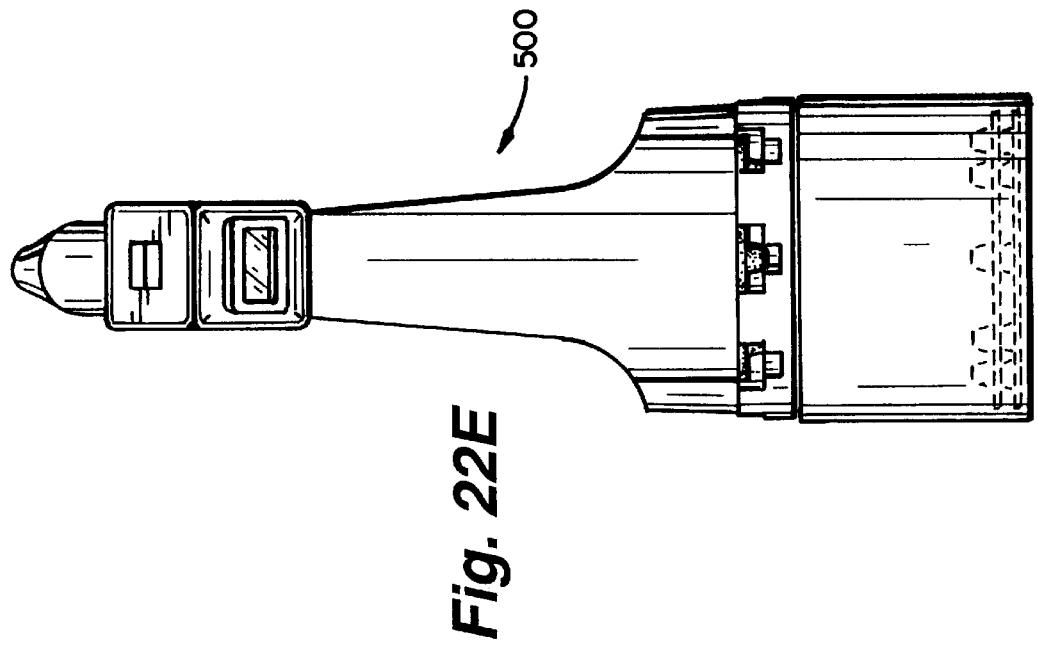
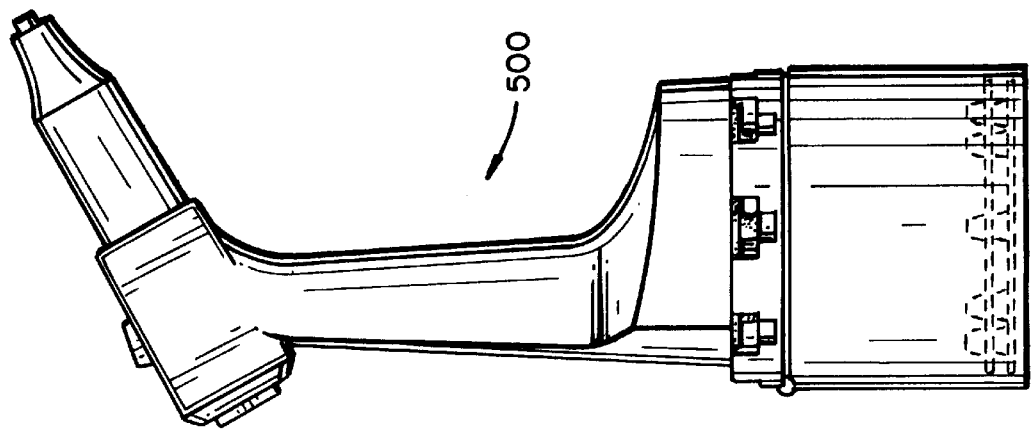
Fig. 22E

TYMPANIC THERMOMETER WITH MODULAR SENSING PROBE

CROSS-REFERENCE TO RELATED APPLICATIONS

This application claims the benefit of U.S. provisional application no. 60/048,752 filed Jun. 3, 1997 entitled "Tympanic Thermometer With Modular Sensing Probe" (attorney docket no. 2204-9). This application is also related to commonly-assigned copending application Ser. No. 08/747,423 filed Nov. 12, 1996 entitled "Probe Cover For Tympanic Thermometer" (attorney docket no. 2204-2); and commonly-assigned copending application Ser. No. 08/867,838 filed on Jun. 3, 1997 entitled "Tympanic Thermometer Probe Cover" (attorney docket no. 2204-7). The entire disclosures (including the drawings) of each of these related patent applications is incorporated by reference into this application.

FIELD OF THE INVENTION

This invention relates to biomedical instrumentation, and more particularly to portable electronic temperature measuring instruments. Still more particularly, the present invention relates to a modular sensing probe, and to systems and methods, for measuring the core body temperature of a human or animal by receiving and characterizing infrared radiation emitted by the eardrum.

BACKGROUND AND SUMMARY OF THE INVENTION

Doctors, nurses, parents, and other care providers all need to be able to rapidly and accurately measure a person's body temperature. To find out whether a person is sick, the first thing a care provider usually does is take the person's temperature. Someone running a fever is likely to have an infection. A doctor or nurse can tell a lot about how a patient is doing by monitoring the patient's temperature over time and noting how it has changed.

There are three kinds of thermometers in wide use today:

glass thermometers,

"electronic" thermometers, and ear ("tympanic") thermometers.

Glass thermometers are very inexpensive, very small and easy to store, and don't require batteries or other special supplies. For this reason, glass thermometers are probably the most widely used temperature measuring device in the home. However, glass thermometers have the disadvantage that they are very slow in making measurements—they typically require several minutes to reach body temperature. This is uncomfortable for the patient, and may be very troublesome when it is necessary to take the temperature of a small child or an invalid. In addition, glass thermometers are typically accurate only to within a degree, may be susceptible to errors in placement, and can be broken easily.

Because of these disadvantages, most hospitals and doctors' offices now use instruments commonly known as "electronic" thermometers. Most of us have had our temperature taken by an electronic thermometer at one time or another. The electronic thermometer includes a portable, hand-held battery powered unit with a display, and a separate probe. A wire usually connects the probe to the hand-held unit. The probe is long and thin, and has the same general shape as a glass thermometer. To use this kind of electronic thermometer, a nurse first covers the probe with a long thin disposable plastic probe cover that completely covers the probe. The disposable probe cover helps prevent the spread of disease by avoiding direct contact between the reusable probe and the germs in the patient's mouth. The nurse then puts the end of the probe under the patient's tongue. An electronic temperature sensor within the probe electrically senses the patient's temperature, and sends a signal to a microcomputer in the hand-held unit. The hand-held unit usually beeps when the temperature measurement is finished, and displays the patient's temperature on the display. The nurse can then remove the probe from the patient's mouth, strip the probe cover off the probe, and throw away the used disposable probe cover.

This type of electronic thermometer has achieved wide acceptance in hospitals because it is reasonably accurate, can be used with familiar placement techniques, and is (because of its disposable, replaceable probe covers) easily reusable for a number of different patients. Although the electronic hand-held unit is itself more expensive than most households are willing to pay, the overall cost of using this kind of electronic thermometer is relatively low because the disposable probe covers are inexpensive (two to three cents per cover, for example) and a single hand-held electronic unit may last for years and can be used to take the temperatures of many thousands of patients.

Electronic thermometers offer speed, ease of reading, and accuracy improvements over glass thermometers, and also eliminate the possibility of mercury poisoning. Although such electronic thermometers have achieved a fair degree of success, they have certain significant disadvantages. For example, they need to be constantly calibrated, are relatively easily broken, and often require a relatively long time (thirty seconds or more in many cases) to make an accurate measurement. There are also problems with taking a temperature from the patient's mouth due to breathing, keeping the thermometer under the patient's tongue, etc. Cross-contamination of infectious diseases is also a concern because the mouth is a "wet orifice."

More recently, a new kind of electronic thermometer has appeared on the market. This new kind of thermometer works by measuring the temperature of your eardrum. Since the eardrum is also known as the "tympanic membrane," these thermometers are sometimes called "tympanic thermometers."

Why the eardrum? The carotid artery that supplies blood to the hypothalamus—the body's temperature control center—passes through the eardrum. For this reason, the temperature of your eardrum corresponds very closely to the core temperature of your body. Although doctors and scientists have known this fact for many years, only since the mid-1980's have commercial devices been available to measure eardrum temperature in a clinical setting.

Ear or "tympanic" thermometers work by receiving and analyzing the radiant heat ("infrared") energy coming from the eardrum. Just as you can feel the heat when you hold your hands up in front of a warm fire, a tympanic thermometer can detect eardrum temperature without having to actually touch the eardrum by receiving the radiant heat energy coming from the eardrum.

Commercially available tympanic thermometers consist of a portable, hand-held battery powered main unit providing electronics, a display and a probe containing a special type of heat sensor such as a "thermopile" or a pyroelectric heat sensor. This special heat sensor is especially sensitive to the eardrum's radiant heat energy. Microelectronics can determine eardrum temperature from the electrical signals provided by the special heat sensor. The thermopile's sensing probe is typically an integral part of the tympanic thermometer's main unit—reducing the potential for breakage of the sensor assembly and (at least potentially) increasing reliability and accuracy.

To use the ear thermometer, a nurse or other care provider inserts a disposable probe cover onto the instrument's sensing probe. Once the disposable probe cover is in place, the nurse or other caregiver inserts the covered sensing probe into the patient's outer ear and then presses a button to command the instrument to make a measurement. The measurement time is usually very rapid—on the order of two seconds or less. The patient's temperature instantly shows on the instrument's display. The instrument may then be removed from the patient's ear, and the disposable cover can be stripped off the instrument and discarded.

Ear thermometry has advantages over other temperature measuring techniques. For example:

The measuring time is very rapid—usually less than two seconds.

The eardrum is at or near the body's core temperature, providing the most accurate location for non-invasive temperature measurement.

Because the ear is a dry orifice, cross-contamination is not much of an issue—and individual, disposable probe covers further reduce the already low cross-contamination risks.

The theoretical accuracy of the measurement is very high (for example, on the order of one tenth of one degree).

Because of the short measurement time and the use of either ear as the measuring point, it is possible to rapidly measure the temperature of children, invalids and sleeping patients—and in other situations where it is difficult to get a patient to sit still for thirty seconds with a probe under their tongue.

Despite these many clear advantages, ear thermometry has not yet achieved wide success in the medical marketplace. Even though many hospitals are believers in the concept of ear thermometry, the hospital market overall has converted less than twenty-five per cent of its temperature measurements to ear thermometry—and the hospitals that have converted are often displeased with their choice.

The main reason for past failures is that existing ear thermometer/probe cover combinations do not provide the high, repeatable accuracy required in a demanding hospital environment. Nurses are often unable to duplicate ear thermometer readings. If you try to measure the same person's temperature twice with existing commercial ear thermometer/probe cover combinations, you may get two very different readings. Since accurate, repeatable, temperature measurements are important or even critical to medical diagnosis and treatment (for example, to detect a 101.5° F. hospital fever threshold or to establish a temperature pattern over time), it is important for temperature measurements to be as accurate and repeatable as possible.

The sensing probe used to sense the infrared radiation emitted by the eardrum plays an important role in the overall accuracy, repeatability and usability of the tympanic thermometer. For example, the sensing probe needs to be rugged and robust to withstand dropping and other rough treatment it may be subjected to in hospitals and other clinical setting. The sensing probe must also be sensitive to the low level of infrared energy emitted by an eardrum while providing a high degree of accuracy, repeatability and noise immunity. Much work has been done in the past to improve the reliability and accuracy of tympanic thermometer measuring systems. Several units currently on the market comply with the current industry standards. See, for example, "Standard Specification For Electronic Thermometer For Intermittent Determination of Patient Temperature" Designation E 1112—86 (Reapproved 1991) published by the American Society For Testing and Materials ("ASTM"); and the more recent draft proposed "Standard Specification for Infrared Thermometers For Intermittent Determination of Patient Temperature" (ASTM EXXXX-97, May 9, 1997), which specifications are incorporated by reference into this patent specification). However, further improvements are possible.

For example, several past designs incorporate the sensing probe as an integral part of the overall tympanic thermometer's structure. In one past example approach, the thermopile heat sensor is mounted on the same main circuit board that supports electronics used to measure and display temperature. One problem with this prior approach is that it can be difficult to repair or replace the sensing structure if anything goes wrong in the field. Thermometer head failure accounts for a large percentage of all tympanic thermometers being removed from service, so this integral design approach leads to inefficiencies in terms of long term product maintenance, repair and replacement. There are numerous other problems with prior tympanic thermometers that need to be solved.

The present invention solves many of these problems by providing a portable, self-contained tympanic temperature sensing system having many improvements in accuracy, repeatability, and reliability.

In accordance with one aspect provided by the present invention, an ear thermometer comprises a housing and a probe disposed within the housing. The probe is displaceable between first and second positions relative to the housing. A Hall Effect sensor disposed on at least one of the housing and the probe measures the displacement of the probe relative to the housing.

In accordance with a further aspect of the invention, the probe is biased to a forward position. In use, the probe is inserted into a patient's outer ear and the clinician applies pressure to seal the outer ear canal with the probe (and associated disposable probe cover if desired). This applied pressure forces the probe to move against the bias, rearwardly from its forward position. By measuring rearward probe displacement against this bias, the Hall Effect sensor can measures the amount of force the clinician is exerting to press the probe into the patient's outer ear. The thermometer can perform a predetermined action (e.g., automatically take a temperature) when the measured pressure exceeds a certain threshold (thus indicating that the ear canal has been sealed).

In accordance with a further aspect provided by the invention, an ear thermometer comprises an infrared sensor having a cold junction, and analog processing circuitry electrically coupled to the infrared sensor. Thermally conductive material bonded to the infrared sensor cold junction and the analog processing circuitry maintains the infrared sensor cold junction and the analog processing circuitry at substantially the same temperature.

In accordance with a still further aspect of the present invention, an ear thermometer modular sensing probe comprises a thermally and electrically conductive tubular body defining a hollow cavity therein. A miniature circuit board is disposed within the hollow cavity. The miniature circuit board has at least an infrared sensor and a temperature sensor disposed thereon. The infrared sensor having a cold junction, and the temperature sensor measures the temperature of the infrared sensor cold junction. The body also shields the miniature circuit board from electrostatic and RF fields, while virtually eliminating RFI emissions.

In accordance with a further aspect provided in accordance with the present invention, the tubular body is non-magnetic, and at least one Hall Effect sensor is disposed on the miniature circuit board. The Hall Effect sensor measures the position of at least one magnet moveable relative to the tubular body.

In accordance with a still further aspect provided by the present invention, an ear thermometer comprises a modular sensing probe including a probe casing defining a cavity therein, and electronics disposed within the cavity, the electronics including at least an infrared sensor and a temperature sensor, the infrared sensor having a cold junction, the temperature sensor measuring the temperature of the infrared sensor cold junction. A base unit is electrically coupled to the modular sensing probe, the base unit including at least one pluggable memory device. The base unit can be interchangeably used with any of plural modular sensing probes upon installation into the base unit of a pluggable memory device containing information specific to the modular sensing probe.

In accordance with a still further aspect of the present invention, an ear thermometer kit includes a sensor module comprising an infrared sensor having a cold junction, a tip mounting structure optically coupled to the infrared sensor, a temperature sensor thermally coupled to the cold junction, and electronics coupled to the infrared sensor and the temperature sensor, the electronics determining a patient's temperature in response to outputs from the infrared sensor and the temperature sensor. The kit further includes a first replaceable probe tip defining a first form factor that is specially adapted to accept a first disposable probe cover type, and a second replaceable probe tip defining a second form factor different from the first form factor. The second form factor is specially adapted to accept a second disposable probe cover type. Either of the first or second probe tips can be interchangeably coupled to the tip mounting structure and the infrared sensor.

In accordance with a further aspect provided by the present invention, the sensing system includes a base unit and a measuring unit. The measuring unit preferably provides a self-contained, removable, replaceable temperature sensing probe module. The base unit can, for example, support the measuring unit by providing a temperature display, batteries, a receptacle for storing the measuring unit when not in use, and/or a dispenser for dispensing disposable probe covers. The measuring unit can accept and hold disposable foam probe covers during measurements.

In one example, the sensing probe module measures the quantity of infrared (heat) energy coming from the eardrum, and delivers the measurement to a separate base unit. The base unit develops and displays a temperature indication based on the measurement.

In one example, the base unit includes a dispensing arrangement that dispenses removable probe covers. These probe covers are placed onto the measuring unit probe end before taking a temperature to prevent cross-contamination and for other reasons. The measuring unit probe end may include an ejection mechanism that automatically strips off the probe cover after use. In accordance with a further feature provided by the invention, the measuring unit may sense (e.g., magnetically) the position of the ejection mechanism to determine whether a disposable probe cover is in place and/or whether the probe end has been inserted into the outer ear. By sensing ejection mechanism position, the system can, for example, remind the clinician to put on a new probe cover and/or to prevent taking a temperature before the unit has been properly positioned in the ear.

The electronic signal interface between the module and other system components is digital in the preferred embodiment—improving noise performance and associated accuracy and repeatability and allowing non-shielded cabling such as, for example, a conventional telephone handset cord to be used to connect the display and measuring units. In one example system, all analog signal processing components are contained within the sensing module—with all interfaces to and from the sensing module being purely digital.

In one example, the sensing module provides independent, separately measured thermistor and thermopile digital outputs neither of which is used to "compensate" or otherwise affect the other in any way. These outputs can be digitized by an analog-to-digital converter, and provided to the base unit. The base unit may further process the information to generate an accurate, repeatable temperature reading of the patient's core body temperature.

The following is a non-exhaustive list of additional features and advantages provided by preferred embodiment temperature measuring system in accordance with this invention:

Highly accurate and sensitive; capable of achieving 0.1 degree Fahrenheit resolution.

Cost-effective and easy to use.

Measuring unit probe end is specially adapted to use foam probe covers of the type disclosed in U.S. patent application Ser. No. 08/867,838 of Cheslock et al entitled "Tympanic Thermometer Probe Covers" (attorney docket no. 2204-7) filed Jun. 3, 1997.

Different, interchangeable probe end tips can be used to accommodate various types of probe covers including a foam design, a rigid polystyrene design and a thin film design.

Modularized temperature-sensing head and electronic control package streamlines production and testing while providing for various packaging configurations and deployment methods.

Meets or exceeds all current ASTM requirements.

The modular sensing probe has unique thermal characteristics, and is capable of operating over a wide dynamic temperature range with accuracy down to a fraction of a degree, in both Fahrenheit and Celsius.

The modular sensing probe provides excellent thermal characterization while accommodating versatile hardware support and generous software headroom.

The modular sensing probe can provide a high degree of accuracy and compatibility with a range of different host platforms and configurations.

Low power requirements.

Sensor module is programmable; base unit or other host can download configuration information to sensor module.

The self-contained, removable, replaceable sensor module and memory module allow for simple field replacement without returning the entire thermometer to the manufacturer for reconditioning.

A conventional 4-conductor modular coiled telephone handset cord can be used to communicate signals and power between the base unit and the measuring unit.

All analog circuitry is mounted on a compact circuit board within the sensor module. The single compact circuit board can contain all power supply and analog circuitry (including A/D converter and associated digital signal processor) required to make thermopile and thermistor fully functional.

Epoxy material can be used to pot all components of a sensor module. For example, the analog circuitry and thermopile can be bonded permanently with thermally-conductive epoxy to a screw-machined, cylindrical housing. The epoxy minimizes any chance of mechanical damage to the thermopile and electronic components—and the entire sensor module is watertight, water-proof and shock-resistant.

Analog components, including the thermopile, can be potted together in thermally conductive epoxy to equalize temperatures between components—constraining all electrical thermal drift offsets isothermally and providing an isothermal relationship of the thermopile cold junction and the analog processing circuitry.

All communications to and from the sensor module are in the form of digital signals. All interfacing between the sensor module and the rest of the system is at a TTL digital level. In one example embodiment, a single (e.g., 4-pin or 12-pin) connector can be used as the only normally used interface to the sensor module—providing an unregulated DC supply and a digital interface for thermometry operation.

The sensor module casing can be made of a conductive material such as machined aluminum—providing high electrostatic field and RF isolation and good heat transfer. The analog circuitry and the screw-machined housing are electrically grounded externally to the sensor module. This configuration allows the sensor module screw-machined housing to act as an electrostatic and Faraday shield, increasing the signal-to-noise ratio (e.g., to −160 dB for 50–60 Hz), and offering general isolation from radiated noise sources across a wide bandwidth. The shield also reduces spurious RF emissions such as radiated broadband noise—ensuring compliance with FCC Part 15 specifications.

The thermistor can be embedded within the thermopile can to simplify construction and ensure higher reliability and close thermal coupling.

An operational amplifier within the sensor module amplifies the thermopile output with a gain optimized to ensure that at conventional ambient hospital temperatures, there is adequate separation between two adjacent 0.1 degree A/D conversion points.

The sensor module may include an A/D converter and an on-board microcontroller—providing programmability and flexibility.

An A/D converter integral within the sensor module housing may employ a scaleable and programmable analog gain amplifier and low pass digital filter—allowing for characteristic responsivity differentials between thermopiles so that the sensor modules can be made identically. The lowpass filter decreases the overall noise figure while providing high noise rejection (e.g., rejection of noise in the 50–60 Hz range).

The tip of the sensor module (where the removable probe covers attach) can be made of a thermally non-conductive material—reducing adverse potential accuracy degradation due to "drawdown." A non-conductive thermal barrier reduces any tendency of the sensor module to draw heat off of the ear canal, and further coupled with the preferred thermally insulative foam-based probe cover design, better permits the clinician to secure same-ear repeatability The tip of the sensor module, the lens, and the optical waveguide are removable and replaceable parts. This allows for the easy and simple replacement of the most vulnerable mechanical components.

The cylindrical sensor module housing is a screw-machined part with no moving assemblies. This design negates the need for any kind of mold for manufacturing while permitting multiple vendor sources. It dramatically reduces the initial manufacturing investments while keeping production-quantity costs low. It also significantly increases the total MTBF (mean time between failures) of the assembly.

In one embodiment, the sensor module includes waveguide closed by a polyethylene, silicon or germanium lens. The lens protects against accuracy degradation due to dirt and grime. The waveguide can easily be removed and replaced in the event that the lens becomes scratched.

The machined sensor module and its associated analog circuit design easily allows for multiple-sourced thermopiles without tooling or design changes being made. This takes advantage of the subtle size and responsivity differences seen from thermopile manufacturer to manufacturer, without compromising performance. It also negates the cost of carrying different types of physical inventory in the event that an alternate thermopile is required, as well as the cost of any additional design burden.

The sensor module can, in one embodiment, provide an analog input for resolving black body target reference temperature during calibration. This feature serves at least two purposes: it allows an external voltage source to be used to set the system gain and calibration ranges, and it simplifies the manufacturing support tooling used to calibrate sensor modules.

The sensor module can withstand rough treatment and dropping without significant damage. The overall design is virtually impervious to damage when physically mounted to a thermometer chassis so that the connector pins are not exposed. Damage to the waveguide lens resulting from dropping the unit in such a way that the lens absorbs most or all of the impact of a drop from a significant height can be cured by replacing the waveguide and recalibrating.

The sensor module can be commanded to perform multiple A/D conversions, separated in time, to separate signal from noise. In one embodiment, the A/D converter for each displayed temperature, samples the thermistor output, then samples the thermopile output multiple times, then again samples the thermistor output. Sample averaging can be used to improve accuracy and noise rejection.

Since positioning technique is an important part of temperature repeatability and the clinician may know best when all the criteria have been met for proper placement, the measuring unit may include a temperature button that the clinician manually depresses to trigger a temperature reading.

In another embodiment or mode of operation, the thermometer can automatically initiate a temperature measurement when it senses that the patient's ear canal has been sealed, and the proper pressure applied.

Probe cover sensing mechanism prevents cross-contamination from an unprotected probe tip being inserted into the ear, or by a used probe cover being inserted into the patient's ear.

Magnetic (e.g., linear Hall Effect) sensors within the sensing probe module can be used to detect push button depression and/or probe cover positioning—allowing the sensing probe module to house all measuring unit electronics, and eliminating all wires or interconnects from the sensing probe module.

Possible to sense when the probe cover has sealed the patient's ear canal, and to automatically perform and/or disable temperature measurement until sealing has occurred (thus achieving a high degree of repeatability and encouraging the clinician to use an improved technique).

Magnetic (e.g., linear Hall Effect) sensors within the sensing probe module can be used to sense when the probe cover has sealed the patient's ear canal by sensing over-travel and force exerted by the patient's ear onto the sensing probe module. One example senses force by allowing the probe module to be moveable with respect to its outer case, and spring biasing the probe module toward a forward position. A Hall Effect sensor can determine the amount of force being applied to the probe module by sensing its position—which has a predetermined relationship to the amount of force acting against the spring bias.

Over-travel and force-sensing can be used to achieve a high degree of repeatability by automatically activating a temperature measurement and/or disabling temperature measurement until sealing has occurred (thus effecting improved technique).

Probe module can be linked to a "personality" or memory module for simple and fast field replacement and/or repair.

All tasking for probe cover position sensing, push button activation, A/D conversion, sampling and averaging and other functions can be performed within the sensing module.

The microcontroller within the sensing probe module can be programmed to determine quiescent state and change of state of the Hall Effect sensor outputs. For example the microcontroller can look for an output change greater than a threshold to determine if a button has been pushed or a probe cover position-indicating magnet has been moved into a predetermined position.

The probe cover ejection mechanism carriage can be spring loaded and movable, so a magnet that it carries moves away from an associated magnetic sensor when the probe is pressed into the outer ear. This allows the microcontroller to detect when the probe has been pushed into the outer ear. The system can be designed to remind the clinician to install a new probe cover before taking a temperature.

Alternate unitary system embodiment can provide all necessary functions and capabilities within a single handheld, portable unit that also includes a unique probe cover ejection mechanism and a removable probe cover dispenser.

BRIEF DESCRIPTION OF THE DRAWINGS

These and other features and advantages of the presently preferred example embodiments provided by these inventions may be better and more completely understood by referring to the following detailed description in conjunction with the drawings, of which:

FIG. 6 is an exploded view of an example sensing probe module;

FIG. 7 is a cut-away view of an example sensing probe module;

FIG. 10 is a simplified block diagram of an example sensing probe module;

FIG. 12 is a perspective view of an example base unit probe cover dispensing structure;

FIGS. 21A–21B show another example probe cover ejection system;

FIGS. 22A–22E show another example tympanic temperature measuring system providing a gun-shaped thermometer and a probe cover dispensing base.

DETAILED DESCRIPTION OF PRESENTLY PREFERRED EXAMPLE EMBODIMENTS

Overall Tympanic Thermometer Measuring System

Figure 1:
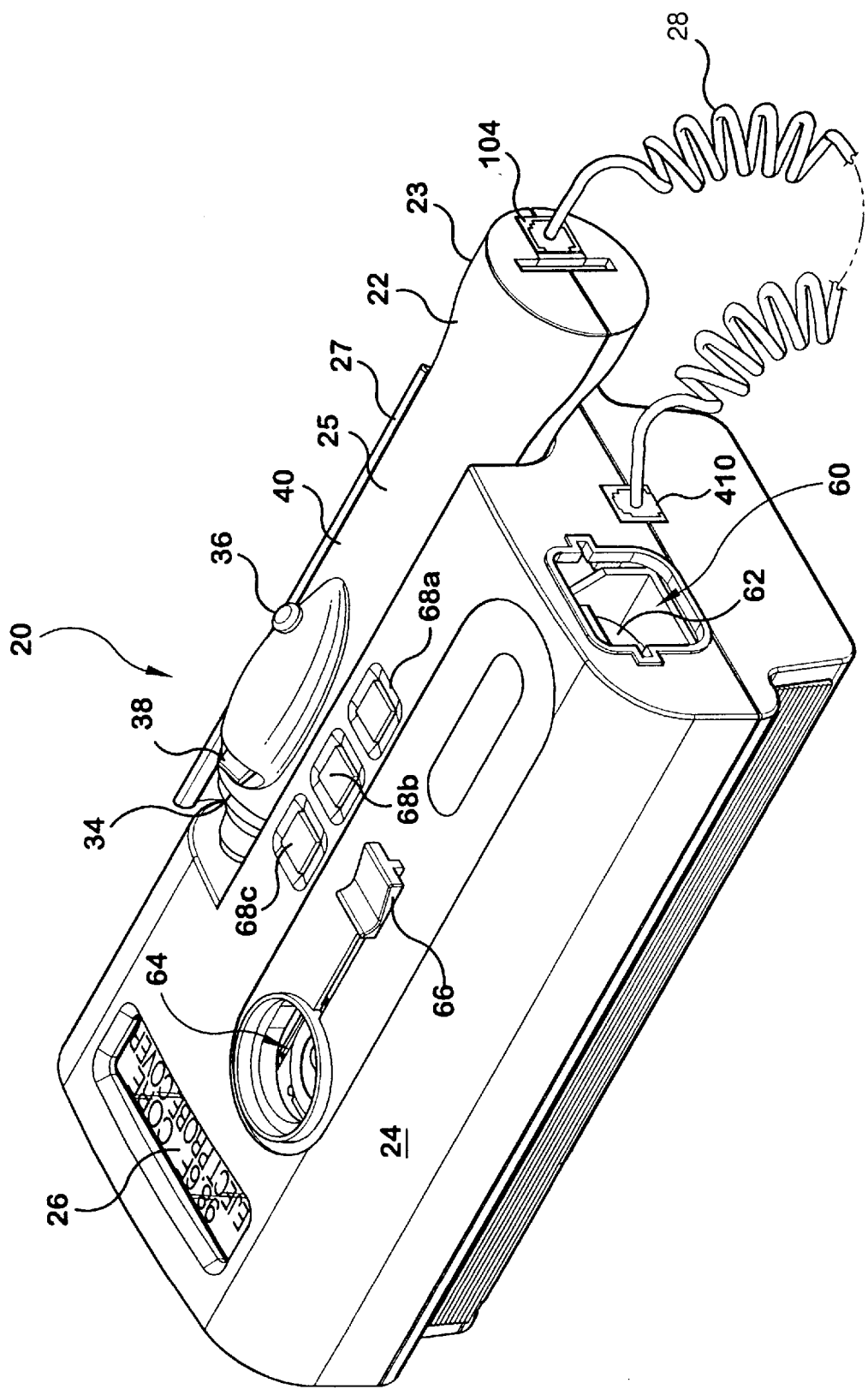
FIGS. 1 and 2 show a preferred example embodiment tympanic temperature measuring system in accordance with these inventions.
Figure 2:
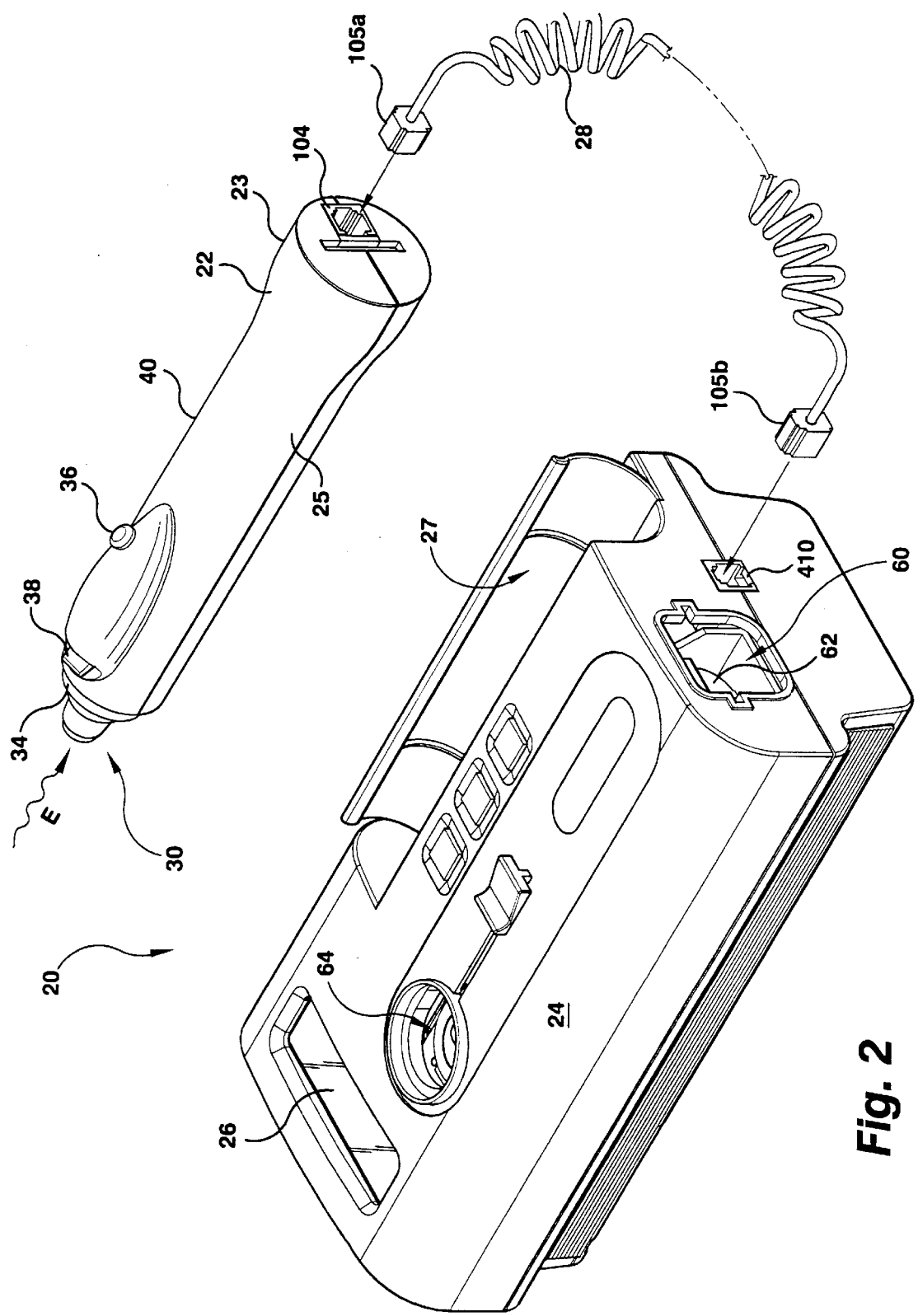

FIGS. 1 and 2 show an example preferred embodiment portable tympanic measuring system 20 in accordance with the present invention(s). System 20 receives infrared (heat) radiation E emitted by the eardrum of a person or animal, and displays on a display 26, an accurate, repeatable indication of the core body temperature of the person or animal.

System 20 in this example includes two major components:

a hand-held portable measuring unit 22; and a base unit 24 which may be portable or stationary.

The hand-held measuring unit 22 receives and measures the infrared radiation E from the eardrum. It sends information about what it measures to the base unit 24. Based on this information, the base unit 24 displays the core body temperature on display 26.

The hand-held measuring unit 22 in this example is small, lightweight, and comfortable to hold in the hand. For example, measuring unit outer housing 40 is preferably thin and tapered so it can be held comfortably in the hand like a large pen or pencil. As one example, measuring unit 22 may have a length of about 6 inches, and a maximum diameter of about 1.1 inches for most of its length. The last 20% of the measuring unit 22's length (see portion 23) preferably is enlarged to a diameter of 1.5 inches to accommodate an electrical connector, but 1.1 inches is preferable in the area 25 which makes contact with the hand. Furthermore, measuring unit 22 preferably is lightweight, having a weight of no more than a few ounces. Providing the measuring unit 22 in a pen or pencil like configuration allows the clinician to more easily manipulate and position the unit in the patient's ear irrespective of whether the patient is standing, sitting, or lying down.

In one example, base unit 24 may include a cavity or cradle 27 (see FIG. 2) sized to accept measuring unit 22. Measuring unit 22 can be inserted into this cradle 27 in base unit 22 when the measuring unit is not in use (see FIG. 1). Storing measuring unit 22 within base unit 24 makes it easier to carry system 20 from one place to another, and can also prevent the measuring unit from damage.

In this example, a standard coiled four-conductor telephone handset cord 28 connects hand-held measuring unit 22 with base unit 24. Standard handset cord 28 is rugged, readily available in a variety of lengths, inexpensive, easy to replace when worn out, and stretchable due to its coiling. Measuring unit 22 and base unit 24 can also exchange measurement data, commands and other information over cord 28. The cord 28 includes standard RJ-11 connectors 105a, 105b that mate respectively with a standard connector 104 on measuring unit 22 and a standard connector 410 on base unit 24.

In this example, power for both units 22, 24 comes from internal batteries within base unit 24. The base unit 24 also sends power to the measuring unit 22 over cord 28. If desired, cord 28 could be replaced with a wireless link, and measuring unit 24 could be provided with a self-contained power source such as miniature batteries, solar cells, etc.

Measuring unit 22 has a probe end 30 (see FIG. 2) that is inserted into the outer ear canal of a patient. Probe end 30 accepts removable, disposable probe covers 32 (see FIGS. 3A–3D). By way of non-limiting example, probe end 30 may accept a foam probe cover as described in U.S. patent application Ser. No. 08/867,838 of Cheslock et al. entitled "Tympanic Thermometer Probe Cover" filed on Jun. 3, 1997 (attorney docket no. 2204-7). Measuring unit 22 in the configuration shown in FIGS. 1 and 2 of this example is especially adapted to accept such foam probe covers. Such disposable probe cover 32 can, among other things:

prevent cross-contamination, protect measuring unit 22 from contacting ear wax and other body secretions, thermally isolate measuring unit 22 from the patient's outer ear, pad the measuring unit probe end 30 to minimize patient discomfort, help direct the probe end toward the eardrum to achieve more repeatable measurement results, and provide other features and/or advantages as described in the above-referenced Cheslock et al patent application.

If desired, base unit 24 may define a receptacle 60 for storing and dispensing unused probe covers 32. Such a receptacle could, for example, accept a disposable cartridge 62 containing any number of probe covers 32. The receptacle may dispense the probe covers 32 one at a time, and provide a platform 64 with a depression in it that retains a probe cover while measuring unit probe end 30 is pressed into the probe cover and the probe cover slides over the probe end. An advance mechanism 66 may be operated to remove the next probe cover 32 from cartridge 62 and advance it into position on platform 64 for receipt by probe end 30.

Measuring unit probe end 30 may have a probe cover ejector mechanism 34. This probe cover ejector mechanism 34 can be spring loaded and retractable. The force a user applies to measuring unit 22 to insert a probe cover 32 onto the measuring unit can cause the ejector mechanism 34 to retract and latch in the retracted position. After taking a temperature reading, the user can depress a button 38 on the measuring unit 22 to release the ejector mechanism 34. Spring bias can automatically return the ejector mechanism 34 to an initial, unretracted position—causing the used probe cover 32 to fly off the measuring unit probe end 30 and into a sanitary waste receptacle. In the preferred embodiment, measuring unit 22 can sense the position of ejector mechanism 34 (retracted or unretracted) to determine whether and when a probe cover 32 has been placed onto probe end 30. Measuring unit 22 can display a reminder on display 26 to apply a new probe cover 32, and can inhibit temperature taking until a new probe cover 32 is placed on prove end 30.

In this example, the measuring unit 22 includes an internal biasing mechanism that biases probe end 30 forwardly. When a clinician inserts the probe end 30 into a patient's ear canal and applies pressure to seal the ear canal, the probe end 30 moves rearwardly against the biasing force. Measuring unit 22 senses this rearward movement and uses it to determine when the patient's ear canal is sealed. This force sensing can be used, for example, to automatically trigger and/or allow a temperature reading.

Push button controls 68a–68c may be provided on base unit 24. These push button controls 68a–68c may be used interactively with information displayed on display 26 to accomplish various results. For example, display 26 could display prompts that a user could select by operating controls 68. Controls 68 may be located adjacent display 26 to facilitate selection of displayed options.

Example Process for Taking a Temperature With System 20

Figure 3A:
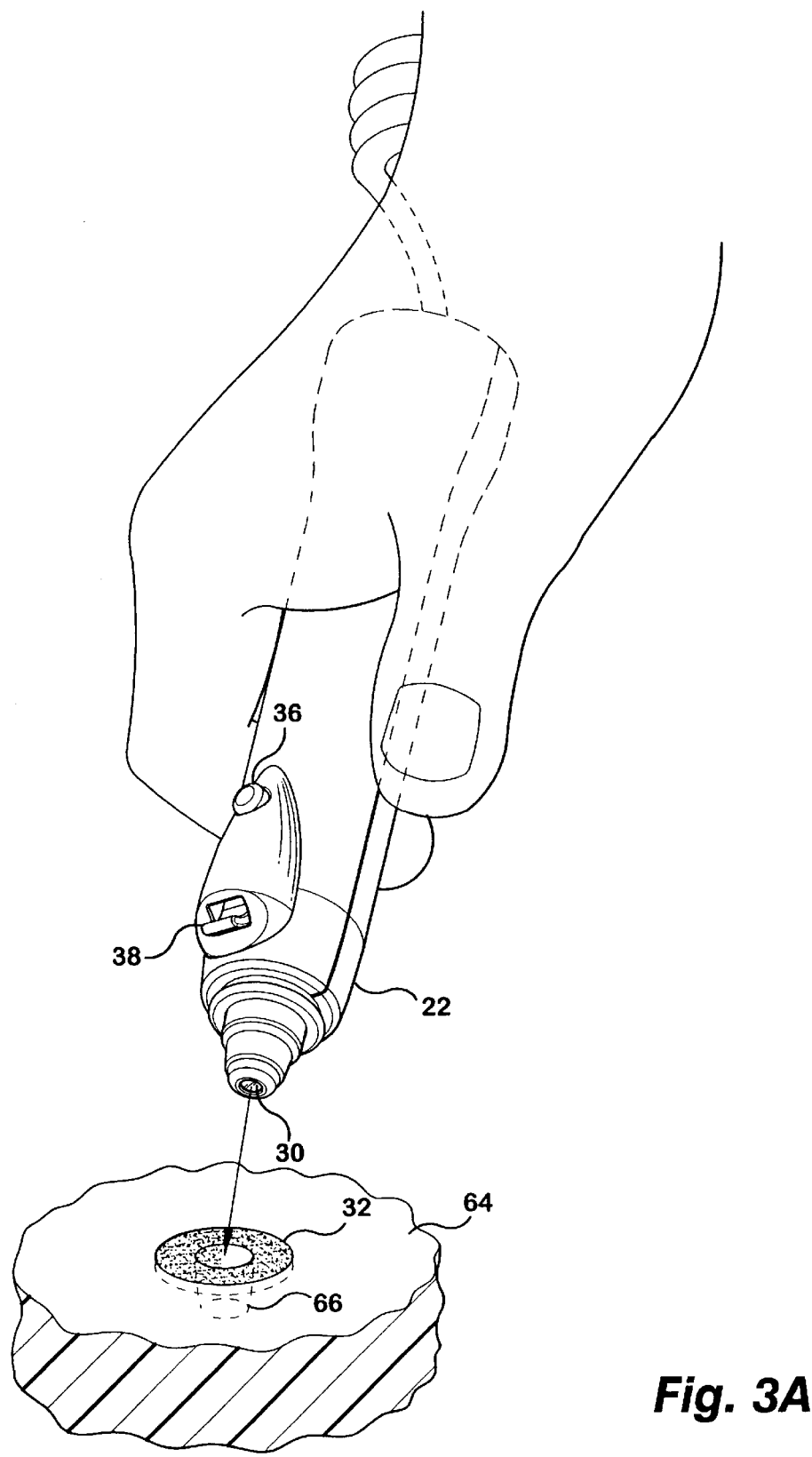
FIGS. 3A–3D show an example process for using the FIG. 1 system to take a temperature.
Figure 3B:
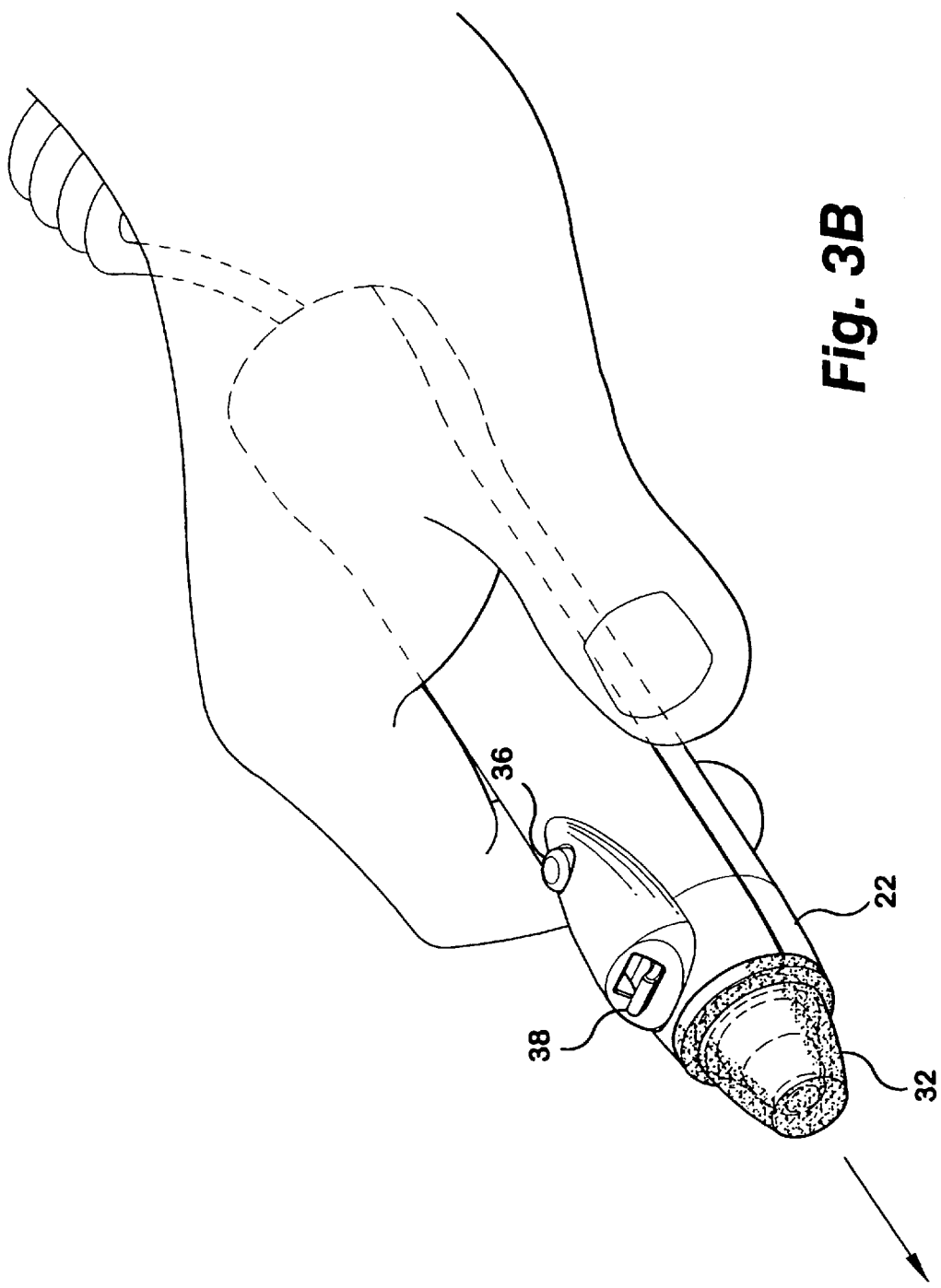

FIGS. 3A–3D show an example process for taking a temperature using system 20. A clinician picks up the measuring unit 22 and inserts the probe end 30 into a disposable probe cover 32 (FIG. 3A). In one example, base unit platform 64 can provide a depression that fits the form of disposable probe cover 32 and retains the probe cover while the clinician inserts the probe end 30 into the probe cover 32. By applying force, the clinician causes the probe cover 32 to stretch around and frictionally adhere to the probe end 30. In this example, this same force also causes the measuring unit ejector mechanism 34 to retract rearwardly and snap into a latched position (see FIG. 3B and FIG. 7A). In this example, measuring unit 22 automatically senses this rearward retraction of ejector mechanism 34 and takes it as an indication that a probe cover 32 has been applied.

Figure 3C:
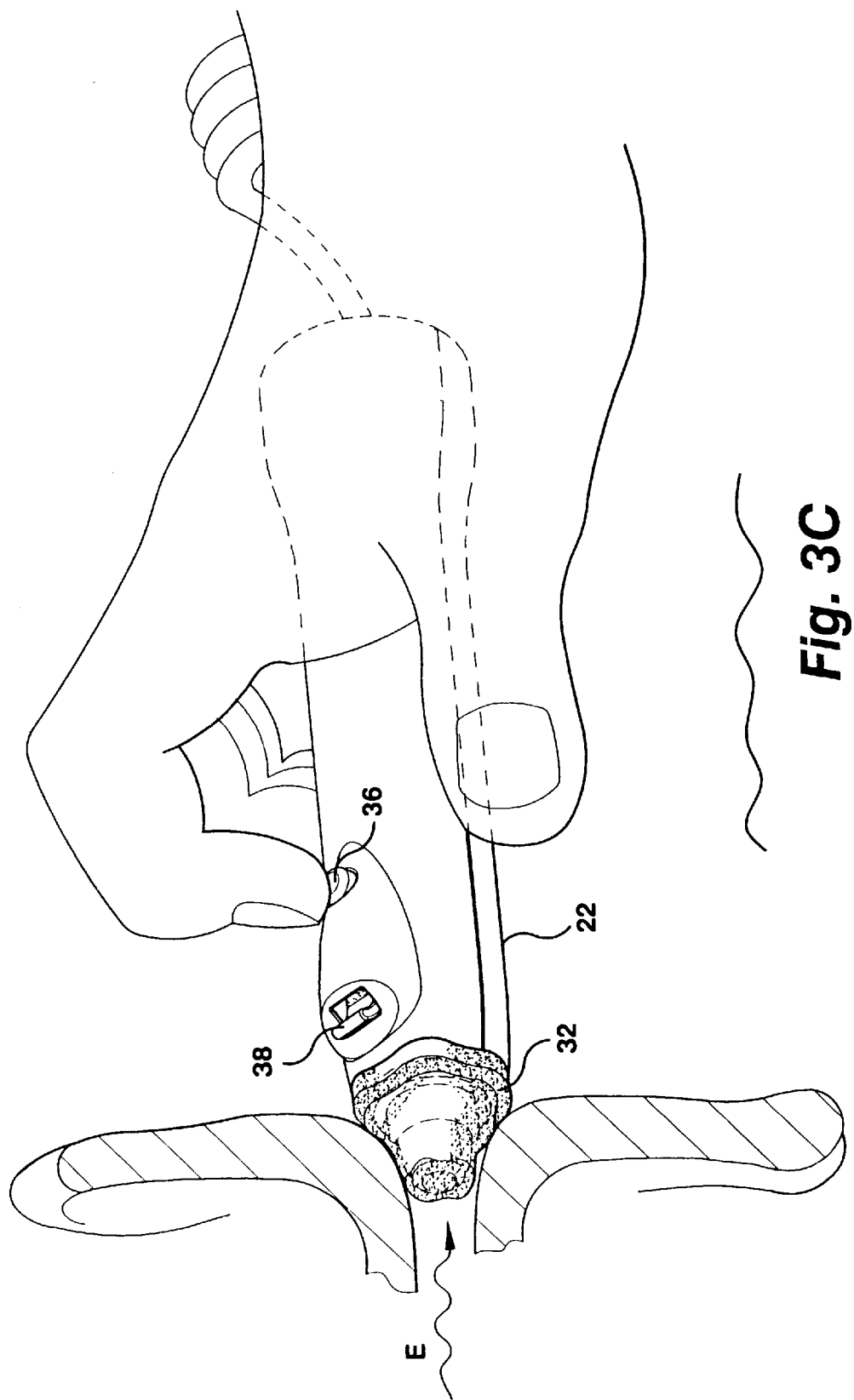

The clinician may then lift the measuring unit 22 (see FIG. 2B), insert the measuring unit probe end 30 (now covered with a probe cover) into the outer ear of a patient, and position the measuring unit relative to the outer ear so that the probe end is aimed at the patient's eardrum (FIG. 3C). Once the clinician has properly positioned the measuring unit 22, he or she may press a push button 36 on the measuring unit to cause system 20 to read the patient's temperature (FIG. 3C). In another mode or embodiment, measuring unit 22 automatically determines when probe end 30 has sealed the patient's eardrum, and automatically initiates a temperature measurement in response. System 20 measures infrared radiation emitted by the eardrum, develops a temperature value based on it, and displays the temperature on display 26 (FIG. 1 and 3C).

Figure 3D:
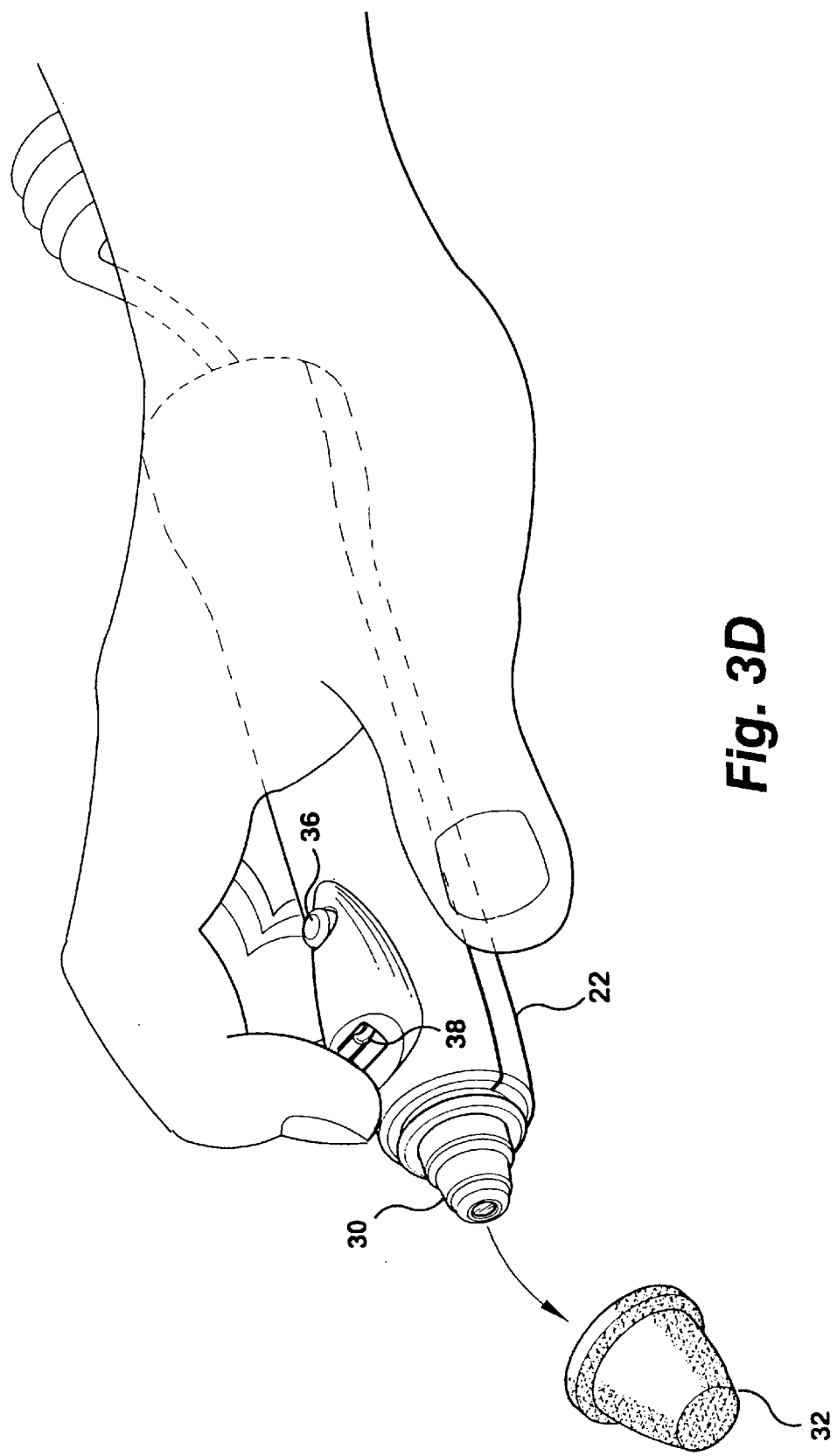

After reading the temperature, the clinician removes the measuring unit probe end 30 from the patient's outer ear, holds the measuring unit 22 over a sanitary waste receptacle, and depresses button 38 (FIG. 3D). Depressing button 38 allows spring-loaded ejector mechanism 34 to spring back to its unretracted position (see FIG. 7B)—causing probe cover 32 to fly off the probe end 30 and into a sanitary waste receptacle. Measuring unit 22 can automatically sense that the ejector mechanism has moved to its unretracted position, and display an indication that the clinician needs to insert a new probe cover 32 before taking the next temperature (see FIG. 1). Measuring unit 22 can now be returned to base unit cradle 27 until the next temperature is to be taken.

Handheld Measuring Unit

Figure 4:
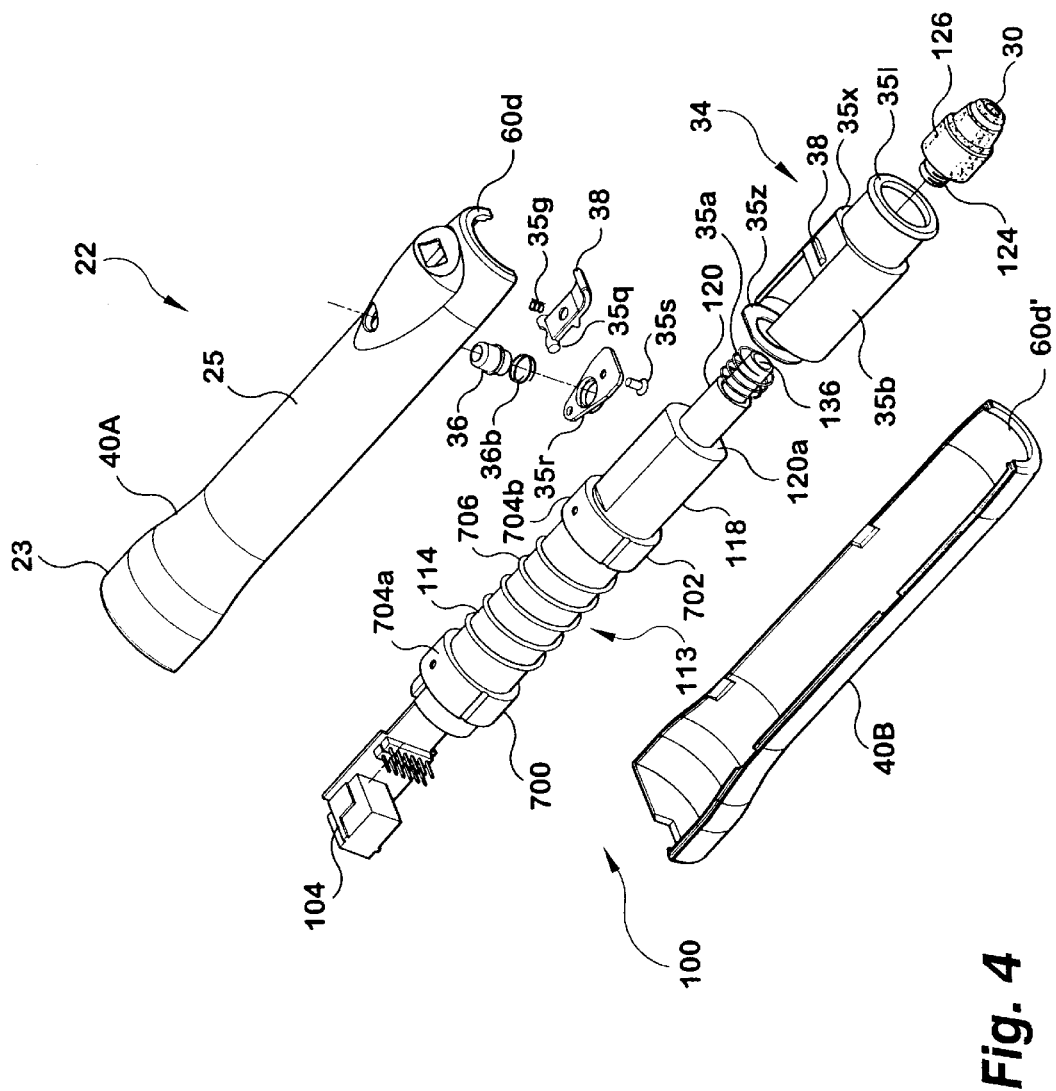
FIG. 4 is a partially exploded view of an example hand-held measuring unit.

FIG. 4 is a partially exploded view of some of the internal workings of measuring unit 22 revealed when pencil-shaped outer housing 40 is removed. As can be seen from FIG. 3, the main components of measuring unit 22 include:

- a two-piece housing 40a, 40b,
- a sensing module 100,
- a spring-loaded push button 36 and associated components, and
- probe cover ejector mechanism 34 including a push button release unit 38.

Figure 5:
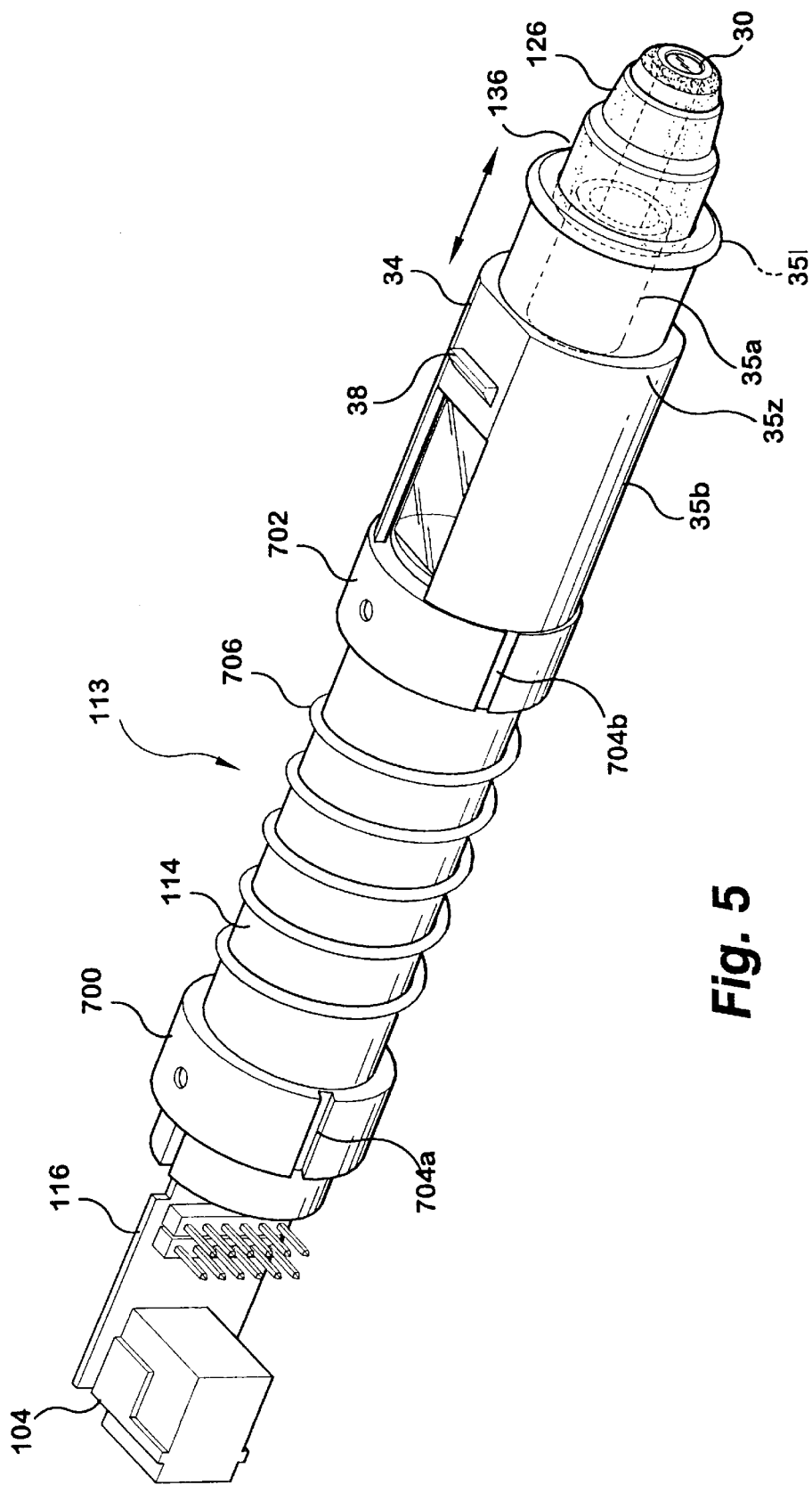
FIG. 5 is a perspective view of an example sensing probe module and associated biasing spring and probe cover stripping sheath.

In more detail, as shown in FIGS. 4 and 5, sensing module 100 is a modularized self-contained sensing module that contains sensors and associated electronic circuitry needed for measuring temperature based on received infrared radiation energy from a patient's eardrum. Sensing module 100 supplies measurement information to connector 104 for communication and further processing by base unit 24.

Connector 104 may be configured as a standard RJ-11 connector of the type that may connect to a standard coiled telephone cord. In the example shown, one or two auxiliary electrical connectors 104a may be provided in addition to module phone cord type connector 104. Auxiliary electrical connectors 104a may have any desired number of electrical pins. In the example shown, auxiliary connector 104a includes two rows of six straight copper or gold-plated pins each. Auxiliary connector 104a can be used for testing and/or diagnostic purposes, to interface with other components (e.g., a display) within hand-held measuring unit 22.

In this particular example, sensor module 100 includes a housing 113 that has a main body portion 114 and an extension portion 118 that extends from the main body portion. Main body portion 114 in this example is generally circularly cylindrical in shape, an extension portion 118 that is also tubular and circularly cylindrical, and a distal end portion 120. Extension portion 118 and distal end portion 120 may, in one example, be screw machined from the same piece of electrically conductive non-magnetic metal (e.g., aluminum) as main body portion 114, so that portions 114, 118, 120 are integral with one another and comprise material which is electrically conductive.

In this example, as shown in FIGS. 4 and 5, two collars 700, 702 are mounted or fabricated onto the main body portion 114 outer surface. Collars 700, 702 are used to allow housing portions 40a, 40b to be fastened to sensing module 100 while permitting the sensing module to move longitudinally with respect to the housing portions. Collars 700, 702 may also act as stops to abut against structures defined by the internal surfaces of housing portions 40a, 40b to limit such longitudinal movement. In one example, collars 700, 702 conveniently can provide longitudinal mounting slots 704a, 704b for mounting and retaining corresponding longitudinal ridges (not shown) within housing portions 40a, 40b while permitting rectilinear movement of sensing module 100 relative to housing 40. See FIGS. 8A & 8B and discussion below. Additionally, a spring 706 is preferably disposed around main body portion 114 between collars 700, 702. As will be explained below, the purpose of spring 706 is to bias module 100 (which is moveable along its longitudinal axis within housing 40) toward a forward end of the measuring unit 22 (i.e., in the direction toward probe end 30). In one example embodiment, at least one of collars 700, 702 is removable to allow spring 706 to be slid over sensing module housing 113.

Ejection mechanism 34 includes a sleeve 35b that is slideably moveable over sensing module distal end portion 120 and extension portion 118. A spring 35a and a washer 35z are disposed between distal end portion 120 and sleeve 35b (the spring being disposed over a waveguide 136 extending out of distal end portion 120. Spring 35a and washer 35z bias sleeve 35b forwardly to provide a probe cover 32 stripping/ejection action (see also FIGS. 9A and 9B). In more detail, double "D" ("D"-shaped) washer 35z is an interference washer that mates with the interior of the "stepped" portion 35x of sleeve 34b. Spring 35a is disposed over sensing module distal end portion 120, one end of the spring abutting sensing module housing stepped portion 120a and the other end of the spring abutting washer 35z. Spring 35a thus acts as a compression spring that tends to push ejection sleeve 35b forwardly away from sensing module 100. The force of spring 35a is exerted onto sleeve 35b at appropriate times to automatically strip a probe cover 32 from cap piece 126. The outer surface of sleeve stepped portion 35x is stopped by a ring portion 60d defined by housing 40—thus retaining sleeve 35b within the housing. See FIGS. 9A–9B and discussion below.

Also as shown in FIG. 4, cap piece 126 in the preferred embodiment is a separate unit including a threaded portion 124 that mates with corresponding threads within distal end portion 120. Cap piece 126 is thus removable and easily replaceable. The particular cap piece 126 shown in FIG. 4 has a form factor design to accept foam based probe covers 32 as described in the above-referenced Cheslock patent applications. However, different cap pieces 126 can be used to accept prove covers 32 of different configurations.

Figure 4A:
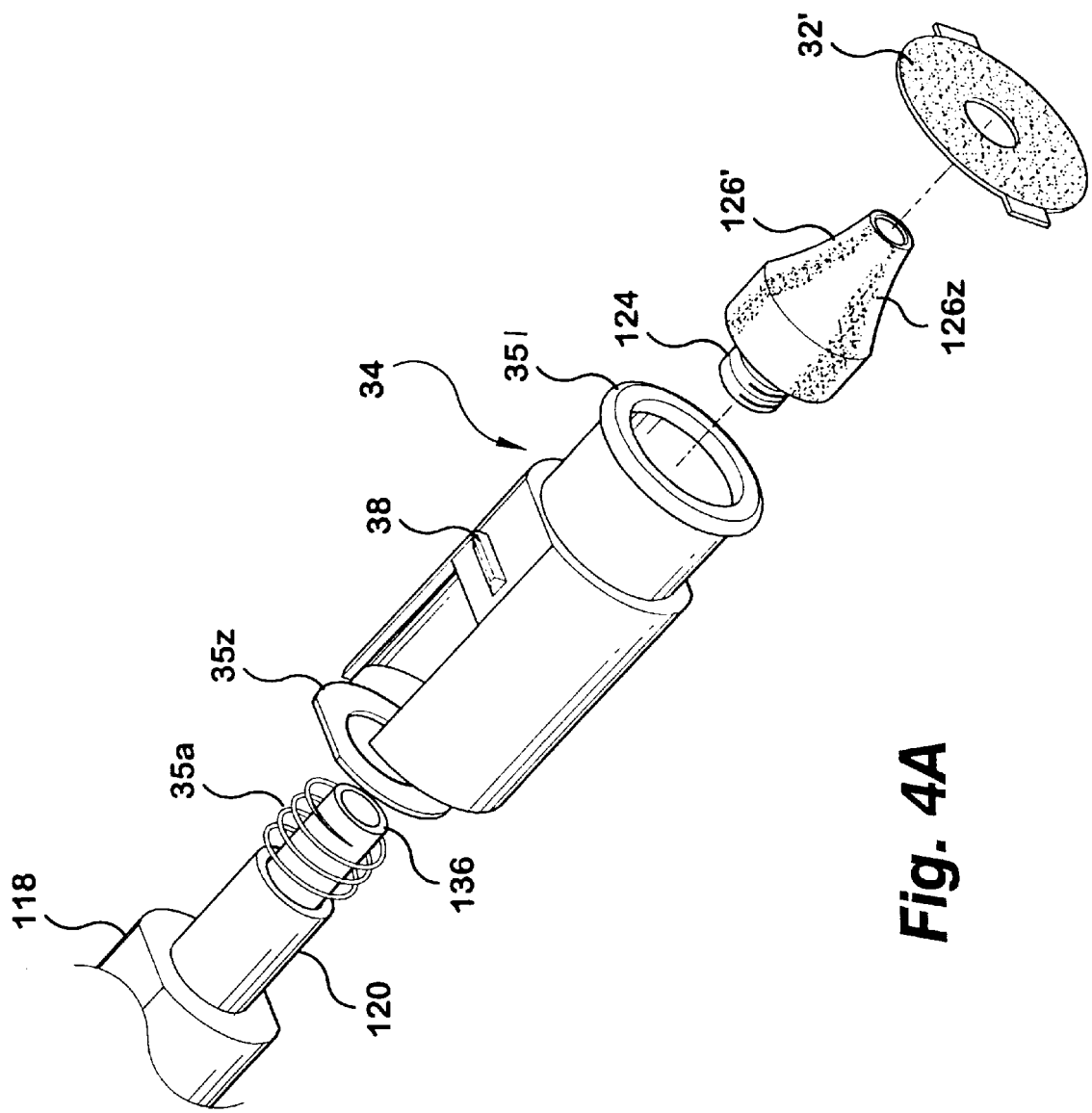
FIGS. 4A and 4B show the use of interchangeable probe tips to accommodate different types of probe covers.

For example, FIG. 4A shows a cap piece 126' having a form factor that is designed to accept thin film type probe covers 32' of the type manufactured by Diatek (a division of Welch-Allyn Co.) Cap piece 126' has an insertion portion 126z defining a curve that is similar to cap pieces commonly used on otoscopes—providing accurate and repeatable aiming of waveguide 136 within the patient's outer ear.

Figure 4B:
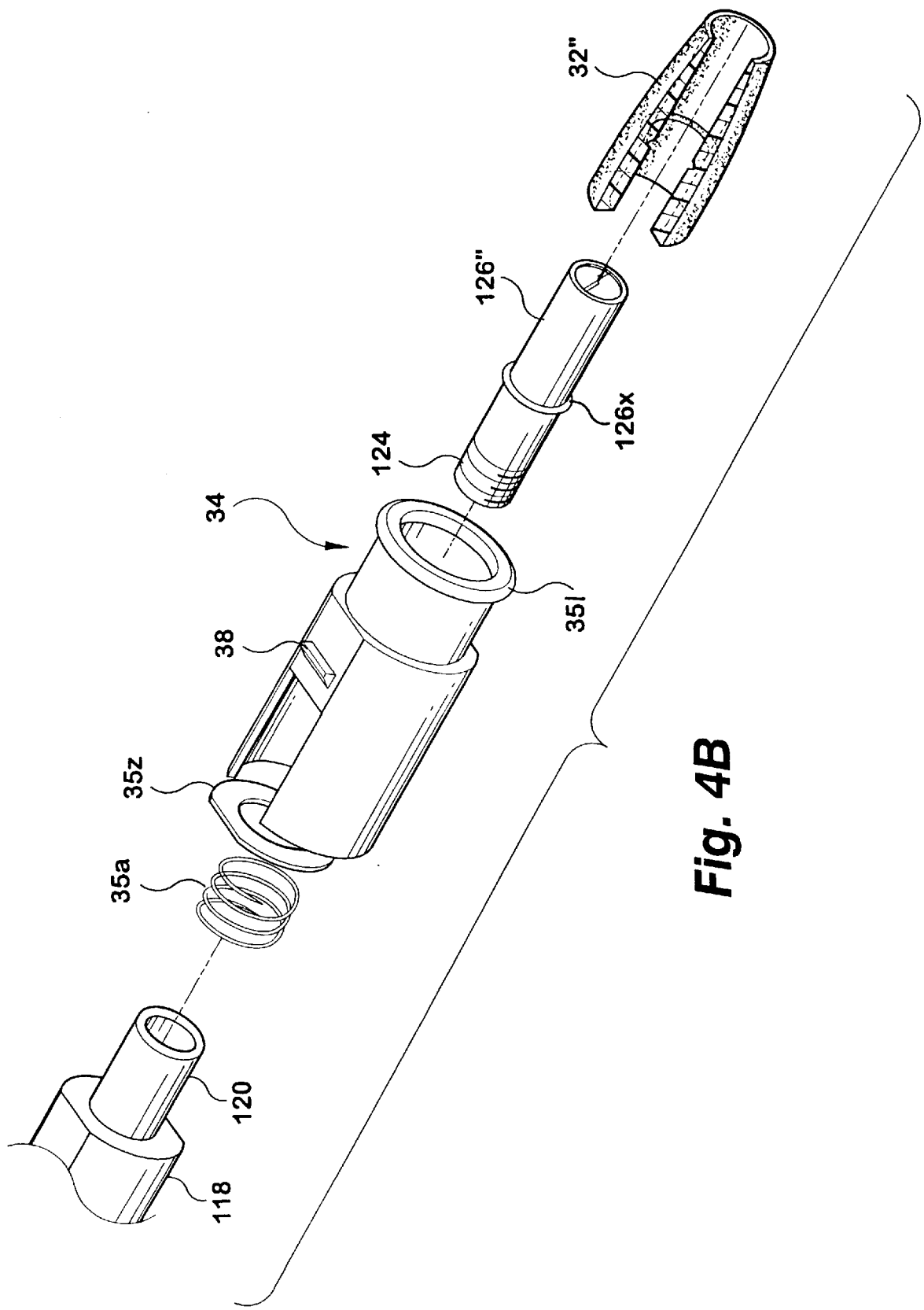

As another example, FIG. 4B shows a cap piece 126" that is hollow tubular and includes a locking ring type structure 126x for mating with a polystyrene type relatively rigid probe cover 32" of the type manufactured by Sherwood IMS and described in U.S. Pat. No. 5,179,936. As described in this '936 patent, locking ring structure 126x may define detents (not shown) which mate with ears located on the inner wall of the probe cover 32" so as to retain the probe cover 32" in place.

System 20 could be sold as a kit with several different cap pieces 126, 126', 126"—or different cap pieces could be separately purchased for use with a previously purchased system 20. Users could select cap pieces 126, 126' and 126" for different probe cover designs (recalibration is necessary since the optical properties of the different probe tips and covers may differ significantly).

Example Sensing Module Construction

FIGS. 6 & 7 show one example construction of sensing module 100 comprising the following main components:

a housing 113, a printed circuit board 116, a waveguide 136, a probe end cap piece 126, and a lens 134.

The waveguide 136 channels infrared radiation from the ear drum so it strikes thermopile 106 with minimal loss. Cap piece 126 retains the waveguide 136, and also houses lens or filter 134 used to prevent foreign matter from entering the sensor module 100 and to band-restrict the IR. The infrared radiation passes through cap piece 126, lens 134 and waveguide 136 before impinging on thermopile sensor 106. Housing 113 houses printed circuit board 116 on which are mounted the various electrical components shown in FIG. 7.

In more detail, thermopile 106 and other components are mounted on a miniature, elongated 6-layer printed circuit board 116. Housing 113 is preferably hollow, defining within it a cavity 115 (see FIGS. 6 & 7). Miniature printed circuit board 116 is disposed within housing cavity 115. Housing 113 is preferably made out of a non-magnetic material such as aluminum or plastic to make the main body transparent to the magnetic fields from magnets 34a, 36, allowing those magnetic fields to reach magnetic sensors 115.

In one example, printed circuit board 116 is epoxied into cavity 115 so that electrical connector 104 extends just beyond cavity annulus 115a. In this example, thermally conductive epoxy 115 is used to hold printed circuit board 116 within the housing cavity 115. In this example, all components of printed circuit board 116 are potted together with such highly thermally conductive epoxy 146. This means that all of these components are at substantially the same temperature—eliminating or minimizing variables due to temperature differences between the various components. Epoxy 146 may, for example, be inserted into cavity 115 using a syringe or other injection technique. Thermally conductive epoxy 115 forces all components (including the thermopile) to drift together thermally. This provides a high degree of repeatability regardless of varying temperature coefficients of the individual parts.

As an example, it is possible in some other designs for the heat transfer characteristics of the thermopile 106 cold junction assembly and the analog circuitry 110 to be exposed to a change in temperature—allowing the two assemblies to change temperatures at different rates. However, calibration is normally performed in a stable thermal environment— meaning that despite their different heat transfer characteristics, that they are essentially at the same temperature during calibration. But when the product is deployed into the marketplace, two separate assemblies may rarely be at the same temperature, as they were in calibration. And even a small temperature differential can result in several hundred parts-per-million offset in an analog circuit. This can dramatically impact accuracy. Since thermopiles typically output in microvolts which must then be amplified before being resolved, even small errors in the thermopile output can lead to substantial measurement errors during signal amplification. The preferred embodiment provided by this invention avoids such errors by holding all electrical components at the same temperature.

In this example, main body portion 114, extension portion 118 and distal end portion 120 are all hollow. Main body portion 114 in this example is generally circularly cylindrical in shape, and defines a cylindrical cavity therein that snugly holds printed circuit board 116. Extension portion 118 is also tubular and circularly cylindrical, and defines a hollow internal cylindrical cavity dimensioned to snugly accept waveguide 136. A portion 119 of main body portion 114 within cavity 115 can be further drilled out to snugly accommodate the form factor of thermopile 106 when the circuit board 116 is fully inserted into the cavity. Extension portion 118 may, in one example, be screw machined from the same piece of electrically conductive metal (e.g., aluminum) as main body portion 114, so that portions 114, 118 and 120 are integral with one another and comprise material which is electrically conductive. This structure ensures that thermopile 106, waveguide 136 and printed circuit board 116 are all maintained at substantially the same temperature.

The printed circuit board 116 and housing 113 can be electrically grounded together—allowing the housing to act as an electrostatic and Faraday shield. The shielding provided by electrically conductive housing 113 can offer general isolation from radiated noise sources across a wide bandwidth. For example, this shielding can reduce the amount of 60 Hertz electromagnetic radiation from reaching the components on circuit board 116—providing for example a signal-to-noise ratio of −160 dB for 50–60 Hz. The shielding can also reduce spurious RF emissions such as radiated broadband noise—ensuring compliance with FCC Part 15 specifications.

In this example, the distal end 120 of housing extension portion 118 may include an internal threaded portion 122 (see FIG. 7). Housing threaded portion 122 may be adapted to mate with corresponding threaded portion 124 of cap piece 126. Housing extension portion 118 defines a central, axial circularly cylindrical passage 123 through its center, and cap piece 126 similarly defines a central, axial circularly cylindrical passage 125 therethrough. When housing threaded portion 122 and cap piece threaded portion 124 are mated together by screwing the cap piece into the housing extension portion 118 by a predetermined number of revolutions, the cap piece passage 125 and the extension portion passage 123 connect to form an overall continuous cylindrical passage extending from thermopile 119 to an opening 133 at the cap piece distal end 135. Infrared radiation travels through opening 133 and down this continuous passage 123, 125 to impinge upon thermopile 106.

In this example, cap piece opening 133 is sealed by a lens 134. Lens or filter 134 provides a high degree of transmissivity (e.g., 80%–90%) to infrared radiation of the wavelength of interest but helps prevent foreign substances (e.g., dirt, dust, ear wax, etc.) from entering passage 123, 125. The material and thickness of lens 134 is selected so that the lens is substantially transparent to infrared magnetic radiation of the wavelength of interest. In this example, lens 134 is constructed out of 15 mil thick polyethylene plastic. The lens is made from inexpensive polyethylene sheet that will not crack from significant lateral stress and shock, or scratch easily. Other products use a silicate or germanium lens filter (window), the substrate of which is vulnerable to cracking, while the surface can be easily scratched. These prior filters are also easily marred by human body oils, affecting temperature measurement. In contrast, the polyethylene sheeting lens 134 is much more resistant to both body oils and dust.

In this example, lens 134 is fabricated to have an outside diameter that is slightly oversized relative to diameter of cap piece passage 125. In one example, lens 134 is press fit into the cap piece 126 and retained by friction. In another example, an additional retaining structure (e.g., a ring cut into the cap piece passage 125, a retaining ring or other structure, etc.) is provided to retain lens 134 at a predetermined position within cap piece passage 125.

In this example, a gold-plated waveguide 136 is inserted into passage 123, 125 between lens 134 and thermopile 106 to channel infrared radiation E as it travels from the lens to the thermopile while minimizing loss as infrared radiation travels through the passage. In one example, waveguide 136 comprises an elongated thin, gold-plated metal tube. The waveguide inner surface 138 may be gold-plated and polished to provide high reflectivity and low emissivity for infrared radiation E traveling from lens 134 to thermopile 106. In another example embodiment, waveguide 136 is not gold-plated, but has an inner surface 138 that is sufficiently reflective to minimize infrared radiation loss as the radiation travels down the length of the waveguide. In still another example, the separate waveguide 136 may be eliminated, and the inner passage 123, 125 (which may be plated and/or polished if desired) defined in part by housing extension portion 118 and in part by end piece 126 may be used to direct infrared radiation from lens 134 to thermopile 106.

As shown in FIG. 7, waveguide 136 is preferably snugly retained between lens 134 and thermopile 106 so that there is no rattling or other mechanical movement. A distal end 142 of waveguide 136 abuts lens 134, whereas the opposite end 144 of the waveguide abuts thermopile 106. The waveguide 136 is dimensioned so that its outside diameter is just slightly smaller than the inner diameters of extension portion inner passage 123 and cap piece passage 125. Waveguide 136 and lens 134 need not be in contact. For example, lens 34 may be held in place by friction, an O-ring, or a lip.

Threaded portions 122, 124 allow cap piece 126 to be easily unscrewed and removed from sensor module 113. Removal and replacement of cap piece 126 may be desirable, for example, if lens 134 has become scratched or otherwise damaged. An additional advantage of making end piece 126 as a separate component is that unscrewing and removing the end piece allows a technician to easily remove waveguide 136 from the sensor module 100 for inspection, cleaning and/or replacement, although this would necessitate recalibration. See also FIGS. 4A and 4B showing alternative cap pieces that may be interchangeably installed as desired.

Cap piece 126 may, in one example, include a conical portion 128 and a circularly cylindrical portion 130. Conical portion 128 reduces the diameter of housing extension portion 118 to provide a reduced diameter cylindrical portion 130 suitable for insertion into a probe cover 32 and into the outer ear canal. In one example, cap piece 126 may be made from a poor thermal conductor such as nylon or VESPEL (Polyimide). Fabricating end piece 126 out of a thermally insulative material has an advantage of allowing the end piece to act as a thermal barrier or insulator to minimize the "draw down" effected when sensor module 100 is inserted into the ear canal.

Example Sensing Module Force and Position Sensing

As discussed above, measuring unit 22 in the preferred embodiment is capable of sensing: (a) when a probe cover is inserted onto probe end 30; and (b) when the probe end 30 has sealed the patient's ear canal. In the preferred embodiment, such sensing is performed internally by self-contained sensing module 100 without requiring any wires or other conductors to connect external components to the sensing module. In particular, sensing module 100 senses magnetic fields emanating from magnets disposed in strategic places within other measuring unit 22 structures in order to determine the position of the sensing module relative to those other structures. For example, through such magnetic field sensing, sensing module 100 can determine whether ejection sleeve 35b is in a retracted position indicating that a probe cover 32 has been placed on probe end 30. Furthermore, through such magnetic field sensing, sensing module 100 can determine how much pressure (force) is being exerted on it by determining its own position relative to housing 40. Such force sensing is used in the preferred embodiment to determine whether the clinician has successfully sealed the patient's ear canal.

Figure 8A:
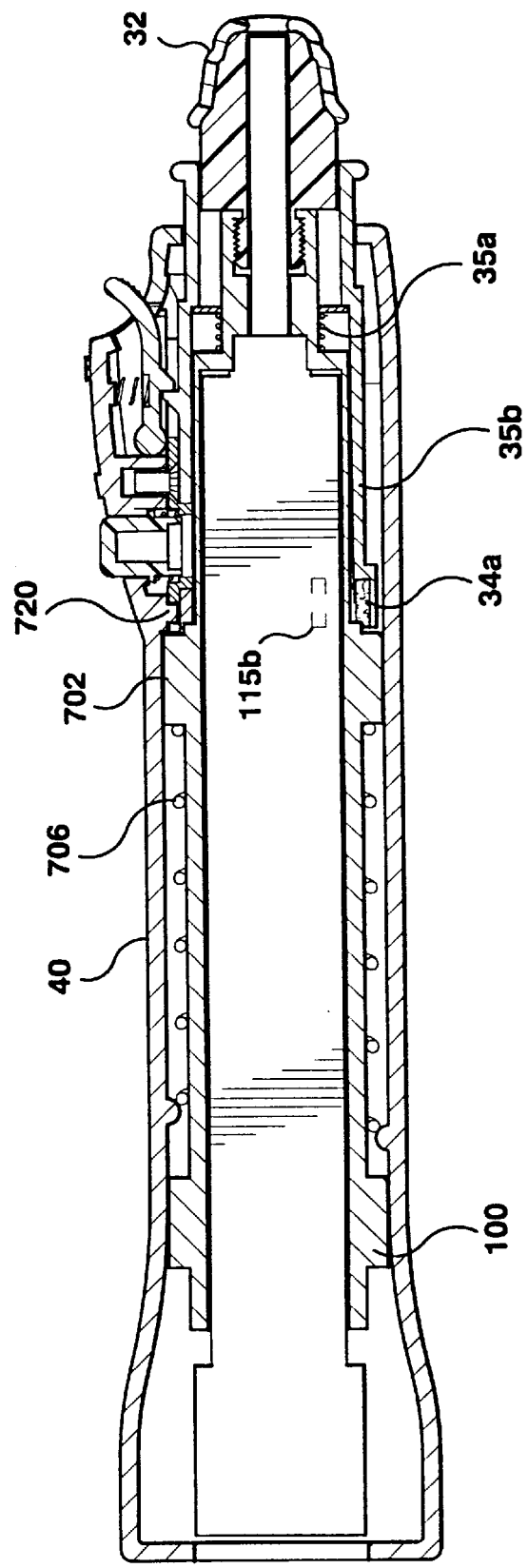
FIGS. 8A and 8B are cross-sectional views of the example measuring unit showing displacement of the sensing probe module within its casing for force and position transducing.
Figure 8B:
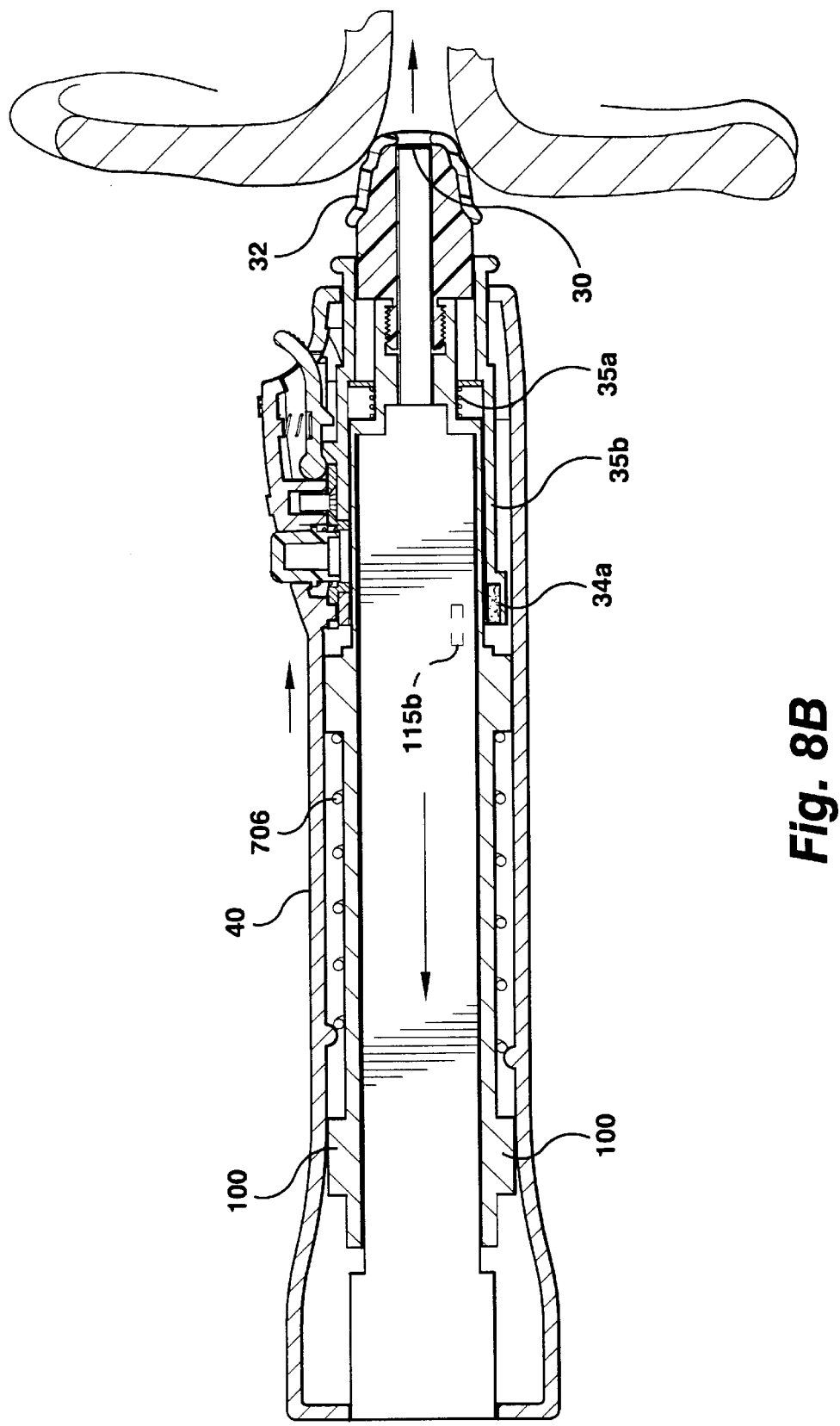

As briefly explained above, sensing module 100 is moveable along the longitudinal axis of measuring unit 22 between a forward position and a rearward position relative to housing 40. FIG. 8A shows the sensing module 100 in its fully forward position, and FIG. 8B shows the sensing module in a rearward position. Spring 706 normally biases sensing module 100 to its fully forward position relative to housing 40 as shown in FIG. 8A. Collar 702 abuts a ridge 720 defined within housing 40 to prevent spring 706 from pushing sensing module 100 further forward than a predetermined forward position as shown in FIG. 8A.

When a clinician uses measuring unit 22 to take a temperature, he or she inserts probe end 30 and associated probe cover 32 into the patient's outer ear canal and attempts to seal the patient's outer ear canal with the probe end and probe cover (see FIG. 8B and also FIG. 3C). The clinician's hand (which is grasping housing 40, see FIG. 3C) applies sufficient force to measuring unit 22 to press at least a portion of probe end 30 and/or probe cover 32 into the patient's outer ear canal. The patient's outer ear, in turn, exerts a force onto sensing module 100, tending to push the sensing module rearwardly against the bias of spring 706. In the preferred embodiment, this rearwardly extending force is capable of pushing sensing module 100 rearwardly by a maximum displacement of about 0.150". There is a predetermined relationship between the amount of force applied by the patient's outer ear to sensing module 100, and the rearward displacement of the sensing module 100 against the biasing force of spring 706. In the preferred embodiment, spring 706 is selected to have an appropriate biasing force (e.g., a 2 lb/in$^2$ compression spring) such that sensing module 100 travels rearwardly by an appreciable amount when a sufficient force to seal a typical patient ear canal is applied to it.

Sensing module 100 measures its own rearward displacement relative to housing 40 to determine whether the patient's ear canal has been sealed. In the preferred embodiment, this displacement is transduced by a linear Hall Effect magnetic sensor 115b, which senses its own position relative to the position of a permanent magnet 34a embedded within ejection sleeve 35b. From this sensed position, sensing module 100 can determine whether the patient's ear canal is sealed, and if desired, the quantity of pressure being exerted by measuring unit 22 onto the patient's outer ear.

In the preferred embodiment, there is an interaction between spring 706 used to bias sensing module 100 forwardly relative to housing 40, and spring 35a used to bias ejection sleeve 35b forwardly during ejection of probe cover 32. In particular, the two springs 35a, 706 are force-balanced. Before describing this detailed interaction between the two springs, it may be useful to describe ejection mechanism 34.

Figure 9A:
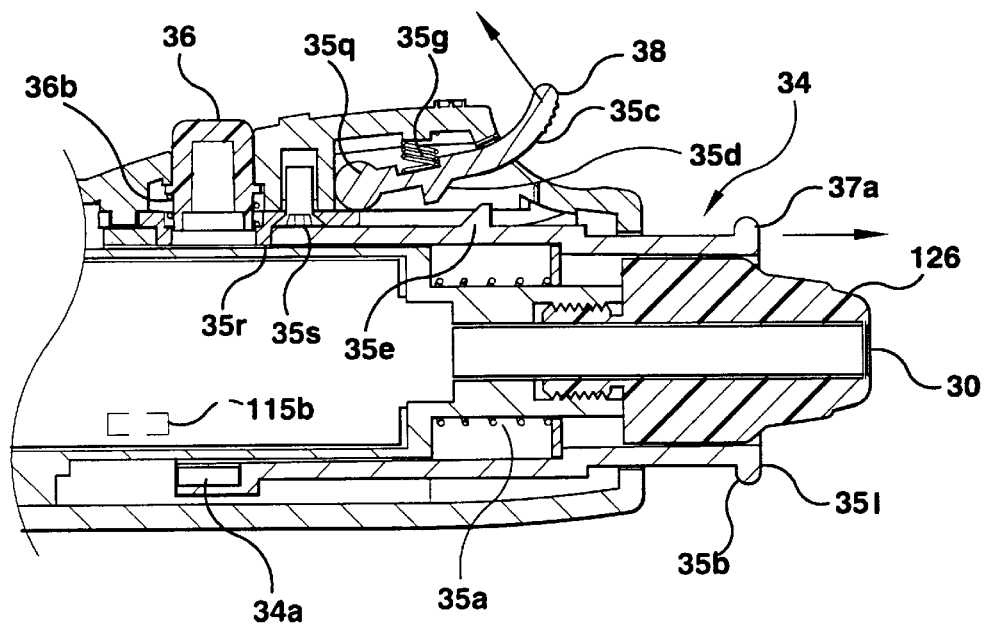
FIGS. 9A and 9B show an example probe cover ejection mechanism.
Figure 9B:
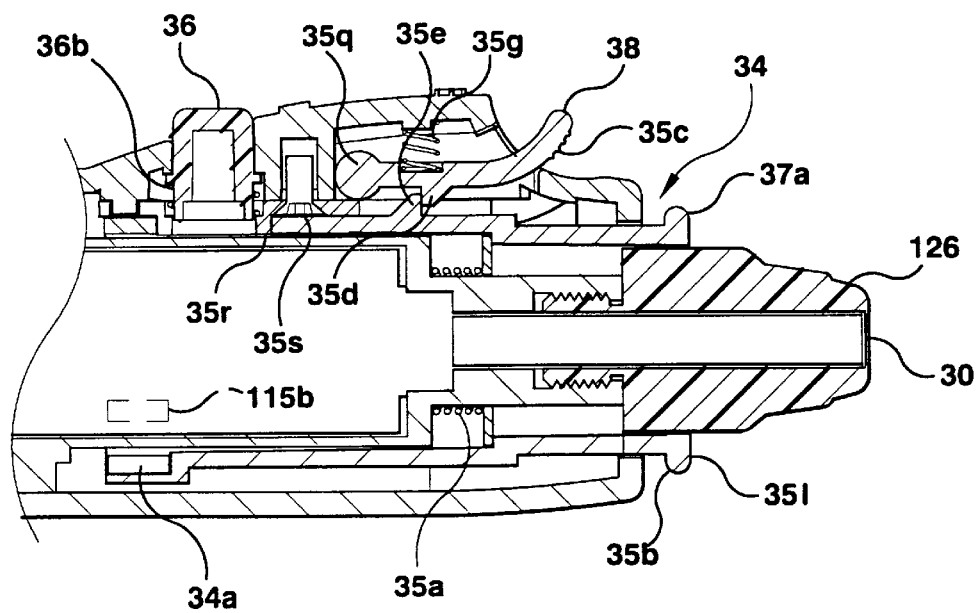

FIGS. 9A and 9B show details of an example probe cover ejection mechanism 34. FIG. 9A shows ejection mechanism 34 in an unretracted (unlatched) position, and FIG. 9B shows the ejection mechanism in a retracted (latched) position. In this example, compression spring 35a biases probe cover sleeve 35b toward probe end 30. Probe cover sleeve 35b has, at its distal end 351, a substantially planar and circular plateau-like surface 37a that is specially adapted to interface with a flat base portion of a disposable foam-based probe cover 32 (see above-referenced Cheslock et al patent applications). The probe cover 32 base portion pushes on the sleeve surface 37a upon installing the probe cover onto the probe end 30. The probe cover 32 frictionally engages and stretches around the probe cover end 30—so that the probe cover is retained on the measuring unit 22 during temperature measurement.

To install a probe cover 32 onto the measuring unit 22, the clinician places a probe cover 32 onto the probe end 30 and pushes the probe end into the probe cover. The outer diameter of probe cap piece 126 is made so that it is slightly larger than the unstretched inner diameter of the probe cover 32. Therefore, as the probe end 30 is inserted into the probe cover 32, the probe cover stretches around the probe end—frictionally engaging the probe end. As the probe end 30 is further inserted into the probe cover 32, the probe cover base portion contacts the sleeve plateau surface 37a. Further pressure from the probe cover 32 (e.g., via a seating structure) allows the probe cover plateau surface 37a to exert a force on sleeve plateau surface 37a—overcoming the biasing force of spring 35a and causing the sleeve 35b to move rearwardly from the probe end.

As sleeve 35b moves away from probe end 30 and toward the other end of the measuring unit 22, a catch tab 35e that extends from sleeve 35b catches on a projection 35d extending from a pivoting latching mechanism 35c. Latching mechanism 35c may be molded out of flexible plastic and include fingerpull 38. Latching mechanism 35c pivots about a pivot 35q, which pivot is retained by a plate 35r (which plate is retained by a screw 35s). A spring 35g biases the latching mechanism 35c downwardly toward catch tab 35e. The interaction between catch tab 35e and projection 35d retains the sleeve in a retracted position under the biasing force of spring 35a. A spring 35g thus biases projection 35d in catching contact with sleeve catch tab 35e. Pulling upwardly on fingerpull 38 causes structure 35c to pivot upwardly about pivot 35q—releasing catch tab 35e from projection 35d and allowing sleeve 35b to slide forwardly under the compressive force of spring 35a.

As described herein, sensing module 100 can sense the position of a magnet 34a embedded within sleeve 35b to determine whether the sleeve 35b is in the position shown in FIG. 9A or whether it has moved to the position show in FIG. 9B. Thus, sensing module 100 can magnetically determine whether the probe cover 32 is in place (based on the assumption that the clinician will not push back sleeve 35b into the latched position shown in FIG. 9B without first placing a probe cover 32 on the measuring unit). Furthermore, as described above, the same sensing mechanism can magnetically determine whether the clinician has inserted the probe end 30 (and the probe cover 32 that covers it) into the patient's ear to seal the patient's outer ear canal. This position sensing can be used, if desired, to set conditions for and/or prompt to take a temperature.

Upon removing the probe end 30 from the outer ear, sleeve 35b returns from the position of FIG. 9B latched position—spring 35g biasing structure 35e in a way that ensures that projection 35d acts as a stop catch 35e for sleeve 35b. In this way, sleeve 35b does not immediately strip a probe cover 32 from probe end 30 upon removing the probe end from the patient's ear.

As explained above, in this example, pulling back fingerpull 38 causes latching mechanism 35c to release projection 35d from catch tab 35e and allow sleeve 35b to slide forward under the force of spring 35a—thus stripping probe cover 32 from probe end 30. The stripping action occurs by the biasing force of spring 35a overcoming the frictional force that the probe cover 32 inner foam surface exerts on the probe end outer cylindrical surface 30', as the sleeve plateau surface 37a presses outwardly against the probe cover flat base portion. The biasing force exerted by spring 35a is sufficient to cause the probe cover 32 to automatically fly off into a waste receptacle such as a wastepaper basket when the clinician manually depresses button 38. As mentioned above, plastic spring 35g biases latching mechanism 35c downwardly to keep projection 35d in contact with catch tab 35e except when fingerpull 38 is pulled upwardly by the clinician's thumb.

Sleeve 35b may define one or more laterally disposed anti-rotation ridges and/or grooves (not shown) that mate with corresponding grooves and/or ridges defined in the housing inner surface 22a to prevent the sleeve from rotating relative to the housing.

Referring once again to FIG. 8B, the pressure applied by the patient's ear to probe end 30 may, depending on the stiffness of spring 35a, provide incidental rearward movement of ejection sleeve 35b as well as rearward movement of sensing module 100. The amount of movement of sleeve 35b may be relatively small (FIG. 8B shows the amount of movement exaggerated for purposes of illustration). Preferably, the compression rate of springs 35a and 706 are selected relative to one another to allow the sensing module 100 to displace a desired amount relative to housing 40 under pressures typically applied by clinicians to seal patient ear canals and without causing undue pressure to be exerted on the patient. The sensing module 100 should displace a sufficient amount to be detectable with a desired degree of resolution while effectively sealing the ear canal without the patient experiencing discomfort.

In the preferred embodiment, sensing module 100 can compare the amount of measured displacement to a threshold in order to determine whether the patient's ear canal has been sealed. This comparison can be used to indicate to the clinician that a temperature can be taken—or it may be used to automatically trigger a temperature measurement. In a subsequent temperature measurement for the same patient, this capability coupled with an otoscopic probe tip, enhances the clinician's ability to target the exact same spot within the ear canal—providing better repeatability.

In a further operating mode, sensing module 100 can quantify the amount of pressure being applied to the patient's ear canal. Based on certain assumptions, i.e., the vascular thermal recovery time of the patient's ear canal, and the surface contact between the probe end 30 and patient's external acoustic meatus (external ear canal), this quantity can be used in conjunction with the known thermal characteristics of probe end 30 and probe cover 32; the amount of time the probe end and probe cover have been in surface contact with the patient; and the time differential between successive temperature measurements, to develop an offset to be applied to a subsequent temperature measurement of the same patient to account for the heat loss from the ear canal.

FIGS. 9A and 9B also show a spring 36b used to bias the temperature-taking push button 36 upwardly away from sensing module 100. Push button 36 descends toward sensing module 100 against the biasing force of spring 36b when the clinician presses the push button—bringing the push button magnet 36a closer to the sensing module and allowing the sensing module to magnetically sense that the push button has been pushed.

Example Sensing Module Circuit Arrangement

FIG. 10 is a simplified block diagram of sensor module 100. Briefly, sensor module 100 works by sensing the heat emitted by the human eardrum. In this example, sensor module probe end 30 is sized and shaped so it may be comfortably and conveniently inserted into the outer ear canal of an adult or child human being. Infrared (heat) electromagnetic energy E emitted from an eardrum (not shown) impinges on sensor module sensing end 102. Sensor module 100 accurately senses the amount of electromagnetic radiation E impinging upon it, and generates a digital output D at an electrical connector 104. Digital output D represents the quantity of infrared radiation E being sensed by sensor module 100—which is, in turn, representative of the core body temperature of the person whose eardrum is emitting the infrared radiation. This digital output D may be further processed by base unit 24, which may convert it into a direct temperature reading for further processing, display and/or storage.

Sensor module 100 in this example is a self-contained removable and easily replaceable unit including the various components shown in the FIG. 10 simplified block diagram. Example sensor module 100 includes a special infrared radiation sensor component called a "thermopile" 106 that produces an electrical output responsive to the quantity of electromagnetic radiation E. Sensor module 100 further includes an additional temperature sensor 108 that monitors the temperature of a part of thermopile 106 called the "cold junction." The analog outputs of these two components 106, 108 are processed by analog circuits 110 within sensor module 100. Analog-to-digital (A/D) converter 112 converts the resulting processed analog signals into digital signals. These digital signals (which represent information by sequences of "on" and "off" signal levels) have a high resistance to external electrical noise and can be processed bymicrocontrollers.

Sensing module 100 can include a microcontroller 109 if desired. Microcontroller 109 is a microscopically small computer on a chip. Microcontroller 109 executes computer software to perform various tasks associated with the sensing module 100. For example, microcontroller 109 handles communications between the measuring unit 22 and the base unit 24 over cord 28. Microcontroller 109 can also control the detailed operation of analog-to-digital converter 112. Microcontroller 109 can also, if desired, perform certain digital signal processing on the signals obtained from analog-to-digital converter 112.

The base unit 24 can download software to measuring unit 22 for microcontroller 109. This ability to dynamically download software to microcontroller 109 provides flexibility. For example, downloading software makes it possible to dynamically change the tasks the microcontroller 109 is performing. In one example, microcontroller 109 can internally store software so it doesn't get erased when power is turned off. Such a "non-volatile" program storage can preserve software within the measuring unit 22 until the base unit 24 (or some other host device) changes the software.

The FIG. 10 example embodiment sensor module 100 further includes magnetic sensors 115. As mentioned above, magnetic sensors 115 in this example detect the presence of a magnet 36a mounted on push button 36, and can also detect the position of a magnet 34a mounted on ejection mechanism 34. In this example, the analog output(s) of magnetic sensors 115 are digitized by analog-to-digital converter 112, and provided to microcontroller 109 for analysis. Microcontroller 109 determines, from these digitized signals, whether the clinician has depressed button 36 to take a temperature and can also sense the force being applied by measuring unit 22 to the patient's outer ear canal (e.g., to determine whether the patient's ear canal has been sealed).

Microcontroller 109 can also monitor, using these digitized outputs of magnetic sensors 115, the position of probe cover ejection mechanism 34. For example, microcontroller 109 can deduce that a probe cover 32 has been placed on probe end 30 by detecting that the probe cover ejection mechanism 34 has been moved back to a retracted, latched position. Microcontroller 109 can also deduce that the probe end 30 has been inserted into the patient's outer ear by detecting that the ejection mechanism 34 has traveled beyond the latched position under the force of the clinician's hand pressing the probe end against the outer ear. Microcontroller 109 can report this information to base unit 24.

Example Base Unit Structure

Figure 11:
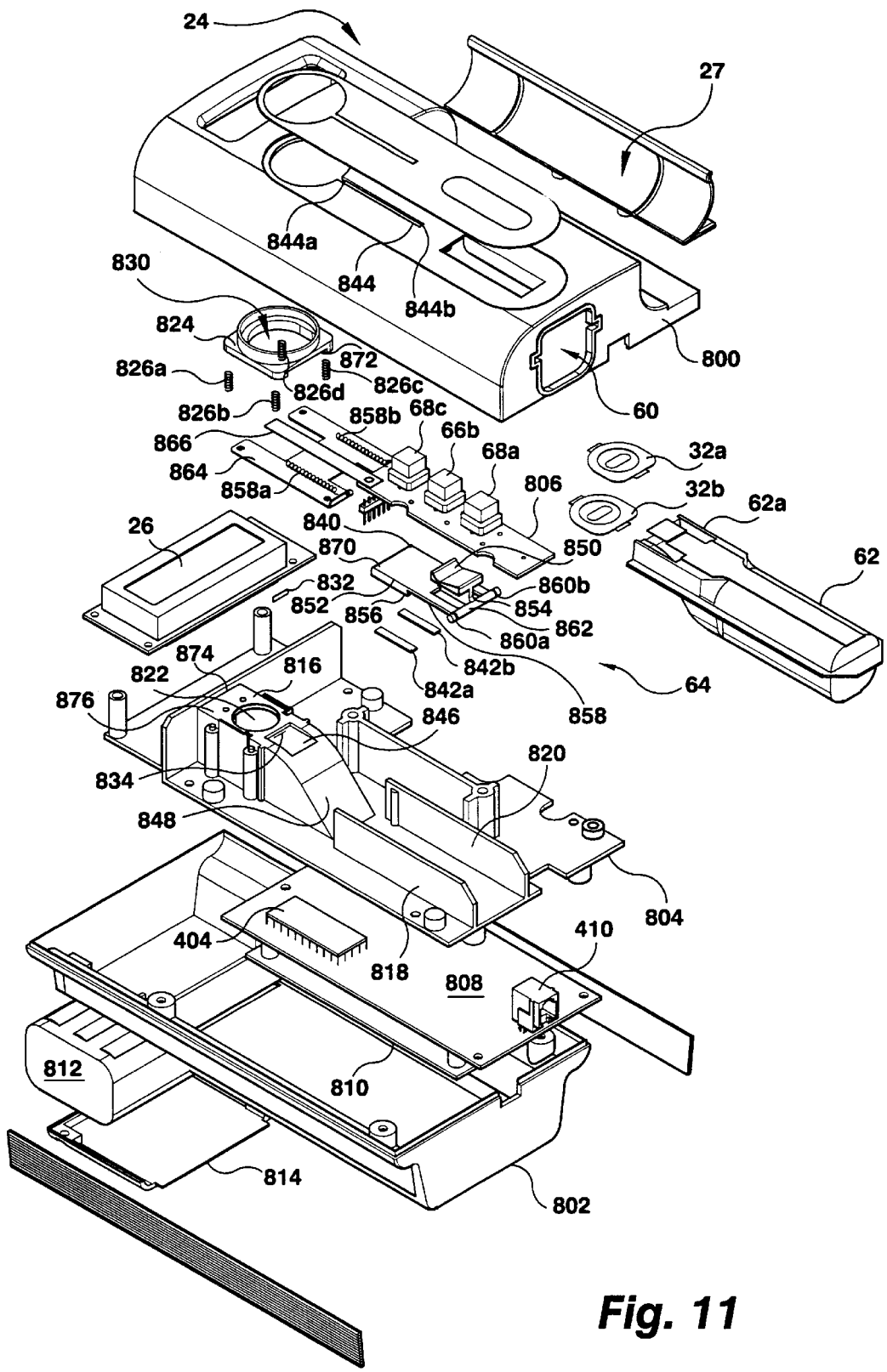
FIG. 11 is an exploded view of an example base unit.

FIG. 11 is an exploded view of an example base unit 24. In this particular example, base unit 24 includes an upper housing portion 800, a lower housing portion 802, and an internal frame member 804. Frame member 804 serves as a common mounting structure onto which most of the components of base unit 24 are assembled. This internal mounting frame member 804 allows the entire base unit 24 to be assembled and tested while all components are fully exposed and accessible. Once testing is complete, upper and lower housing halves 800, 802 are assembled together around frame member 804 to protect and encase the frame member and associated components.

Thus, in this example, the display 26 (which may comprise a two-line alpha numeric liquid crystal display unit) is mounted to frame member 804 along with three circuit boards 806, 808 and 810. Circuit boards 806, 808, 810 contain the electronics for driving display 26, communicating with measuring unit 22 and performing temperature measurement processing. Circuit board 806 has mounted on it the three push buttons 68a, 68b, 68c mentioned above. Circuit board 808 and piggyback circuit board 810 provide the main electronics of base unit 24.

In the preferred embodiment, at least one memory device 404 mounted on circuit board 808 or 810 is pluggable and interchangeable. This pluggable memory device 404 (which in one embodiment may be easily accessible and replaceable in the field) contains "personality" information associated with a particular measuring unit 22. This enables base unit 24 to be used with any desired measuring unit 22 by simply plugging in an appropriate memory device 404. In another embodiment, this programming can be accomplished by connecting a programmer to electrical connector 410 and downloading the information into a flash or another non-volatile memory device, accomplishing the same results electronically while avoiding the need to physically replace any memory device.

In the example shown, base unit 24 is powered by a battery pack 812 which also serves to power measuring unit 22. Battery pack 812 may be a conventional light-weight Nickel-Cadmium or Lithium rechargeable battery pack. Battery pack 812 should provide a sufficient power storage capacity to power base unit 24 and measuring unit 22 for a minimum of a twelve-hour acute care shift. In the preferred embodiment, base unit 24 and measuring unit 22 have been carefully designed to achieve very low power requirements such that battery pack 812 may provide up to a week of continuous service before having to be charged. The charging can be accomplished through use of a standard AC recharger that may connect to a recharging connector (not shown) on the base unit lower case portion 802. An access door 814 may be opened to replace battery pack 812 when necessary.

As discussed above in connection with FIGS. 1 and 2, base unit 24 includes a probe cover dispenser 64 for automatically dispensing probe covers 32 from a probe cover cartridge 62. Probe cover dispenser 64 in this particular example dispenses thin-film type flat probe covers 32 of the type sold by DIATEK. DIATEK probe covers 64 are sold in dispenser cartridges 62 each containing 100 probe covers (see DIATEK Catalog No. 050). These DIATEK probe covers were designed to be inserted into the handle of a gun-shaped tympanic thermometer DIATEK Model 9000. Although the particular example shown in FIGS. 11 and 12 dispenses DIATEK type probe covers, a dispenser for dispensing the foam-based, polystyrene or other probe covers could alternatively be provided integrally with base unit 24.

The DIATEK dispenser 62 includes a dispensing chute 62a that dispenses a strip of probe covers 32 joined together by paper tabs. In this particular example, probe cover dispenser 64 includes a platform 816 defined as part of frame member 804. Dispensing structure 64 successively delivers these probe covers 32 one by one onto platform 816 for application to measuring unit probe tip 30. As will be explained, the dispensing structure 64 further includes an ability to cut each probe cover 32 from the strip of probe covers being dispensed; and a structure that moves the measuring unit ejection mechanism from its unretracted to its retracted position as part of the same overall process a clinician uses to insert the probe tip 30 into the probe cover.

An advance mechanism 66 is used to advance the next probe cover 32 onto platform 816. Advance mechanism 66 in this example includes a slider 840, two rubberized gripping pads 842a, 842b and a slot 844 defined within the base unit upper housing portion 800. In addition, a cutout plateau 846 molded into a ramped region 848 leading to platform 816 cooperates with advance mechanism 66 to deliver a next probe cover 32 to platform 816.

In more detail, slider 840 includes a hand-operated control 850 that extends from upper housing slot 844. The clinician can move slider 840 between first and second positions at opposite ends of slot 844 by simply moving the extending portion 850 relative to base unit 24. The forward travel of slider 840 is stopped by a wall portion 874 defined within frame member 804 at a forward edge 876 of platform 816. Platform 816 is in proximity to a probe cover dispenser 62 retaining structure defined by sidewalls 818, 820 molded as part of frame member 804.

Slider 840 in this example comprises a substantially planar plastic body 852 connected to control 850 by a vertically extending tab 854 dimensioned to fit and slide easily within slot 844. Body 852 has a lower surface 856 defining detents 858 into which rubber grippers 842a, 842b are disposed. Grippers 842 are preferably adhered to the body 852 using a suitable adhesive. Springs 858 connected to grooves 860 (which are defined within a rearward cylindrical portion 862 of slider 840) cause the slider to be biased toward the rear portion 844b of slot 844. These springs 858 are anchored to a metal plate 864 in this example. Metal plate 864 also retains a leaf spring 866 disposed between the plate and slider 840. Leaf spring 866 tends to lift slider 840 upwardly away from plate 866 to prevent grippers 842 from gripping an already dispensed probe cover 32 during return travel of slider 840 under the force of springs 858.

To advance a new probe cover 32 from dispenser 62 onto platform 816, the clinician grasps control 850 and moves it forwardly from its retracted position at the one end of slot 844b to an advanced position at the slot other end 844a. This action causes a forward end 870 of body 852 to pass through a slot 872 defined within a ring portion 824. Meanwhile, grippers 842 grip the next probe cover 32 within dispense 62 and move it forwardly over plateau 846 and onto platform 816. When the forward travel of slider 840 is stopped by wall portion 874, the clinician will know that slider 840 has reached its maximum forward position because it will not go any further. The clinician then releases control 850. Releasing control 850 allows springs 858 to pull slider 840 rearwardly back to its initial position at the end 844b of slot 844. In addition, the clinician's release of downward pressure on control 850 allows leaf spring 866 to upwardly bias the slider to release grippers 842 from the now-dispensed probe cover 32—preventing the return travel of slider 840 from pulling the already dispensed probe cover 32 rearwardly off of platform 816.

Platform 816 provides a suitable orifice 822 through which measuring unit tip 30 may pass in order to envelop cap piece 126 with the probe cover 32. A ring structure 824 suspended over platform 816 by springs 826 is dimensioned to mate with and block the outer ring portion 35l of ejection sleeve 35b (see FIGS. 4 and 5). Ring structure 824 is normally suspended by springs 826 to leave a gap 828 between the ring portion and platform 816 through which probe covers 32 may pass from dispenser 62 into the region of orifice 822 during advancing by slider 840. Once a probe cover 32 is in place beneath ring portion 824, the clinician inserts the measuring unit probe end 30 into the opening 830 defined by ring portion 824. This causes ring portion 824 to move downwardly against the bias of springs 826 and into contact with platform 816. Additional downward pressure the clinician exerts onto measuring unit 22 forces probe end 30 to descend into an orifice 822—thus deforming probe cover 32 and stretching its thin film around the probe end.

At this point, because ejection sleeve outer ring 35l is in direct mating contact with ring portion 824, the ring portion acts as a clamp to clamp the outer periphery of probe cover 32 onto platform 816—preventing the entire probe cover from slipping downwardly into and through orifice 822. As the clinician continues to exert downward pressure onto measuring units 22, the measuring unit ejection sleeve 35b (which bears on the ring portion 824) is moved rearwardly relative to the rest of measuring unit 22 from the position shown in FIG. 9A to the position shown in FIG. 9B. At the same time, the ring portion 824's lower surface presses the dispensed probe cover 32 into a blade 832 disposed in a slot 834 defined within platform 816. The blade 832 cuts the tab between the probe cover 32 disposed within orifice 822 and the next probe cover in the strip being dispensed by dispenser 62.

The clinician knows to stop exerting pressure when he or she feels the ejection mechanism 34 snap into the retracted position—generating an audible click and a tactile sensation. The clinician may then lift measuring unit 22 away from dispensing mechanism 64—probe cover 32 now being inserted onto measuring unit probe end 30 and cut from the remaining probe covers within the strip being dispensed by dispenser 62.

Example Base unit Architecture and Operation

Figure 13:
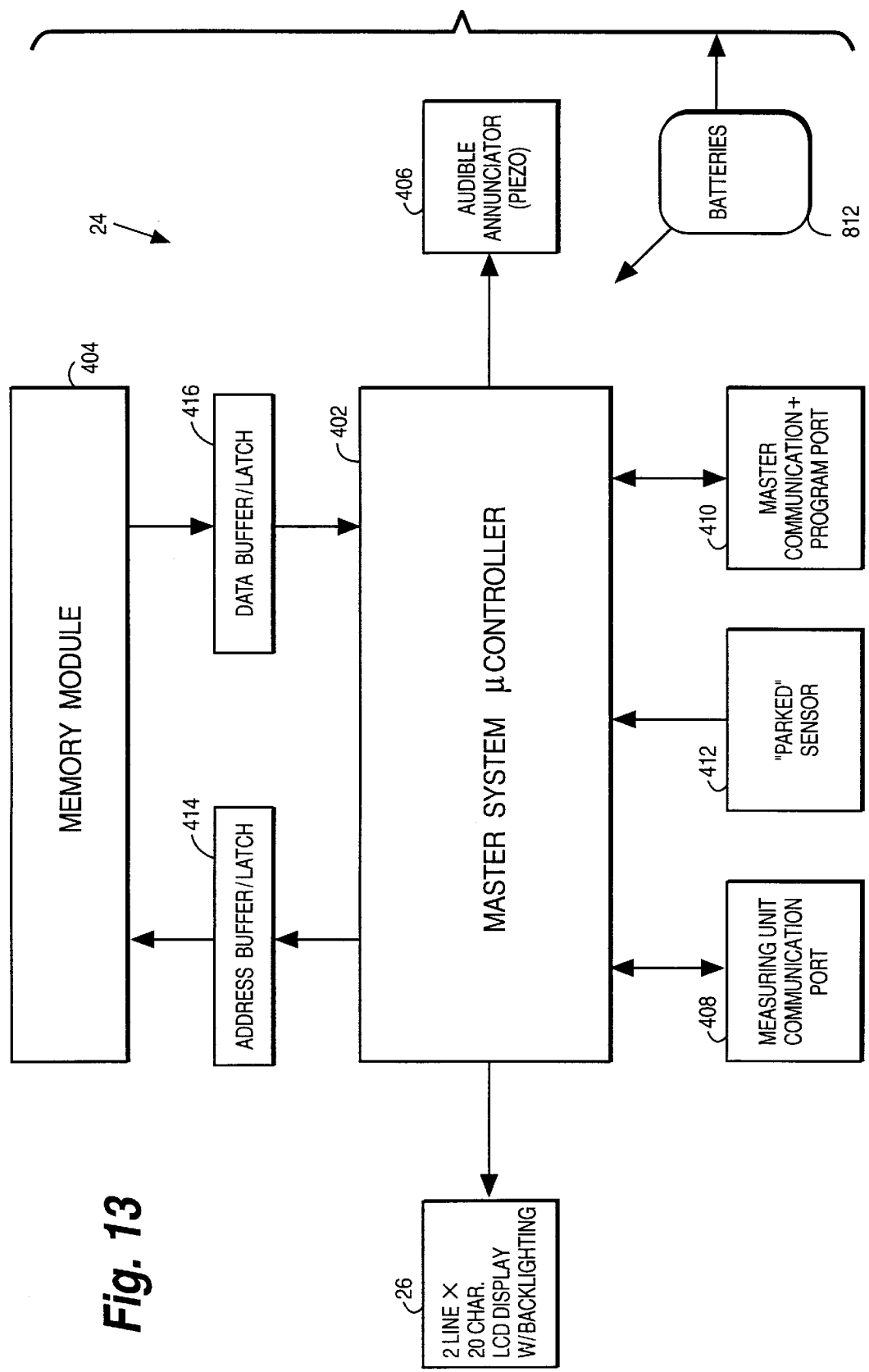
FIG. 13 is an example electrical block diagram of an example base unit.

FIG. 13 shows an example architecture for base unit 24 (or other host unit) adapted to interact with measuring unit 22. In this example, base unit 24 includes a master system microcontroller 402 and a memory module 404. The microcontroller 402 performs tasks under control of software (and based on data) stored in memory module 404. Microcontroller 402 can display information on display 26. Base unit display 26 in this example can display graphics in addition to alphanumeric text. Such graphics can, for example, include various status indicators. If desired, measuring unit 22 can also include a small display (not shown) for displaying core body temperature and/or other information. In this example, base unit can also generate sounds via a sound transducer or other audible annunciator 406.

Microcontroller 402 communicates with measuring unit 22 via a communication port 408 (e.g., a standard RJ-11 4-conductor modular jack that cord 28 plugs into). Microcontroller 402 can also communicate with the outside world via a master communications and programming port 410. A "parked" sensor 412 may be provided to allow the microcontroller 402 to tell whether measuring unit 22 is in its storage position within a cavity defined by the base unit 24 housing. Address and data buffer/latches 414, 416 allow microcontroller 402 to communicate with memory module 404.

Example System Control Steps

Figure 14:
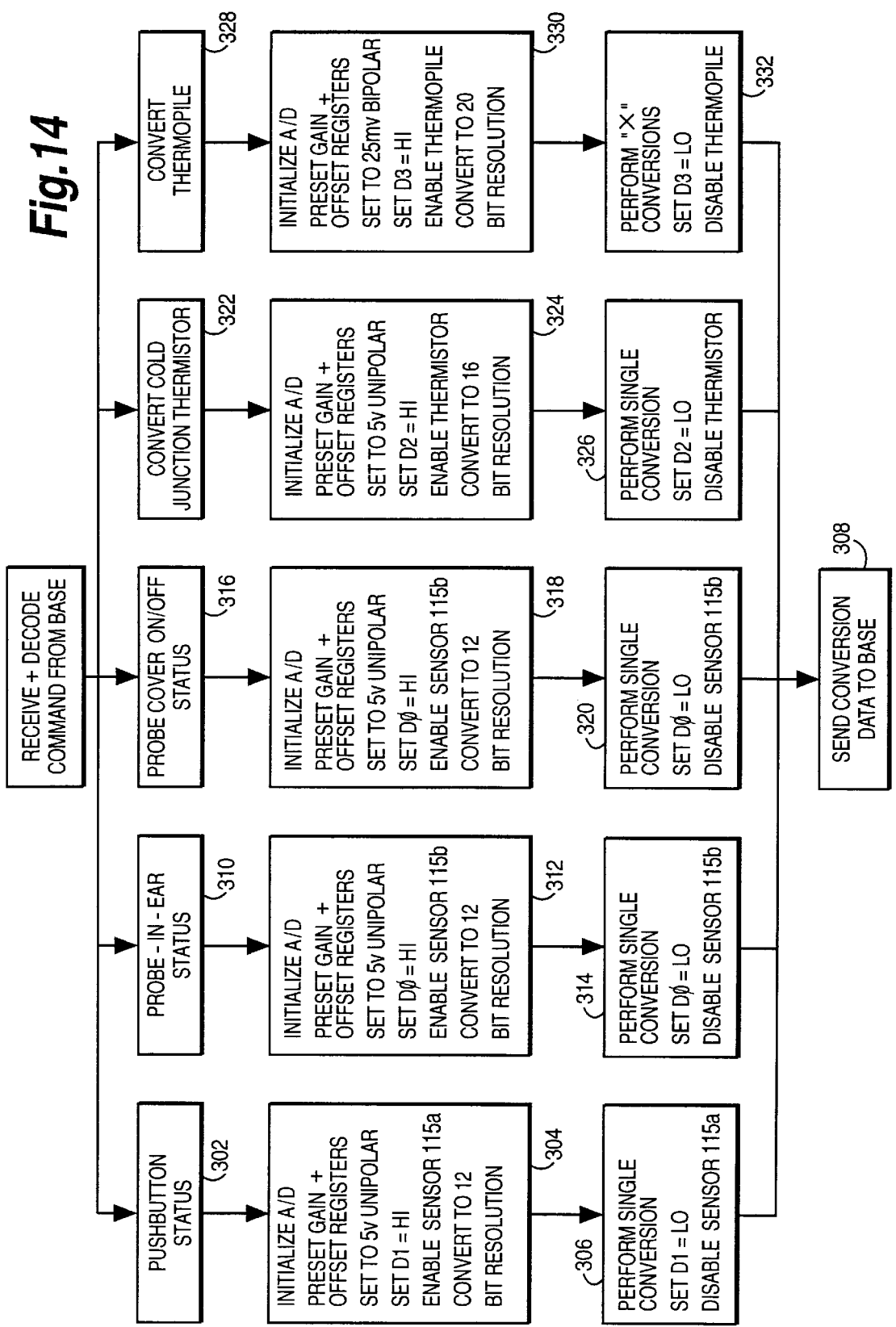
FIG. 14 shows example steps performed by the sensing probe module.

FIG. 14 shows example operational steps performed by sensing module 100 under program control. In this example, the sensing module microcontroller 109 responds to the following commands from base unit 24 or other host:

Read push-button status,

Read Probe-In-Ear status,

Read probe cover on/off status,

Convert cold junction thermistor output, and

Convert thermopile output.

In this example, receipt of a "read push-button status" command from base unit 24 (block 302) causes microcontroller 109 to initialize A/D converter 112 and download configuration data into the converter (e.g., to preset gain and offset registers, and set the device to convert a maximum 5 VDC unipolar input) (block 304). Microcontroller 109 then controls the A/D converter 112 to control multiplexer 206 to select the push button 36 Hall Effect sensor 15a—thus powering on that sensor through decoder 117a and inverter (s) 117b. For example, such configuration data controls multiplexer 110 to select the Hall Effect sensor 15a output for routing to the A/D converter 112 input. Microcontroller 109 then, at the appropriate time, sends clocking signals on the $S_{clk}$ A/D converter 112 input and reads the resulting digital measurement on the $S_{do}$. Microcontroller 109 then downloads appropriate configuration data to the A/D converter 112 via the $S_{di}$ input.

In this example, the microcontroller 109 configures and controls the A/D converter 112 to digitize the output of selected Hall Effect sensor 115a using 16-bit resolution (block 304). The A/D converter performs the requested conversion, and de-selects the multiplexer 206 input—thereby disabling the Hall Effect sensor 115a (block 306). Microcontroller 109 reads the resulting digitized value from the A/D converter 112, and sends it to base unit 24 (block 308).

In this example, upon receipt of a "probe in ear" status command (block 310) or the "speculum on/off status" command (FIG. 14, block 316), microcontroller 109 controls the A/D converter 112 to enable Hall Effect sensor 115b (block 312, 318). Microcontroller 109 also sets up the AID converter for 5 VDC unipolar, 16-bit conversion (block 312, 318). A/D converter 112 reads the output of Hall Effect sensor 115b, and provides it to microcontroller 109 (block 320). In either case, microcontroller 109 determines the relative position of ejection mechanism 34 by measuring the magnetic field that magnet 34a mounted on the ejection mechanism applies to the Hall Effect sensor 115b. Microcontroller 109 provides the determined state value to base unit 24 (block 308).

In one example, system 20 performs a temperature measurement automatically upon sensing that the patient's outer ear has been sealed by probe cover 32. In another example, system 20 can perform a temperature measurement in response to depression of push button 36 only once it detects the patient's outer ear has been sealed by probe cover 32. These features provide improved repeatability, prevent bad readings, and assist the clinician in using proper technique. For example, using the otoscopic probe cover and a DIATEK type thin film probe cover, there is a high degree of assurance that for a given patient, waveguide 136 will be aimed at the same spot within the patient's outer ear each time a certain pressure threshold has been sensed. This provides substantial improvements in repeatability.

In one example, system 20 performs a temperature measurement automatically in response to depression of push button 36, only once it detects that the patient's outer ear has been sealed by probe cover 32 This provides improved repeatability, prevents bad readings, and assists the clinician in using proper technique.

Hall Effect sensor 115B is used to detect the position of ejection mechanism 34. In one example, Hall Effect sensor 115B is exactly in registry with associated ejection sleeve magnet 34a when the ejection mechanism 34 is in the FIG. 9B "latched" position (i.e., the magnet is in registry with the sensor when probe cover 32 is in place but has not yet been pressed into the patient's outer ear canal). Hall Effect sensor 115b can detect the magnetic flux density corresponding to this condition, and can also detect a specific, decreased magnetic flux density value when the sleeve magnet 34a moves out of registry as sleeve 35b "over travels" to a position corresponding to sealing of the patient's outer ear with the probe cover 32. Factors affecting the Hall Effect sensor 115b output for the "sealing" position of sleeve 35b include the tensile strength of springs 35a and 706, and the limit of travel of the sleeve 35b when the clinician inserts probe cover 32 into the patient's outer ear and presses the probe cover into the ear to seal the ear canal. During calibration, Hall Effect sensor 115b may be controlled to sample the magnetic flux densities under these various conditions so that system 20 can "learn" what outputs the Hall Effect sensor 115*b* generates when probe cover 32 has effectively sealed the ear canal. Such empirical data collected during an initial calibration or testing procedure can be used to develop Hall Effect threshold and/or calibration profile data for use in determining the position of sensing module 100 relative to ejection sleeve 35*b*.

In the preferred embodiment, the range of travel of ejection sleeve 35*b* is different when probe cover 32 is ejected versus during pressure sensing. However, Hall Effect sensor 115*b* may not in all cases be able to distinguish between travel of sleeve 35*b* due to probe cover 32 loading and its travel relative to sensing module 100 due to sealing of the ear canal—and thus may not be able to determine whether a decrease in measured flux is due to the probe cover 32 being ejected or because the probe cover is being pressed into the outer ear. To handle such cases, microcontroller 109 can be controlled to continually or periodically check the Hall Effect sensor 115*b* output, and to also periodically or continually check the output of push button 36 Hall Effect sensor 115*a*. Microcontroller 402 can correlate the output of Hall Effect sensor 115*b* with real time events (e.g., the rate at which the magnetic flux density changes the output of thermopile 106, and the output of Hall Effect sensor 115*a*) to reliably deduce the position of sleeve 35*b*. For example, pressure sensing can be "AND'ed" with infrared energy detected from the patient to determine that probe end 30 is in the ear. System 20 may assume under at least some circumstances that any decrease in magnetic flux measured by Hall Effect sensor 115*b* before push button 36 is depressed, has resulted from travel as the probe cover 32 is pushed into the patient's ear—and can determine whether probe cover 32 has successfully sealed the patient's outer ear by looking for a particular measured magnetic flux density corresponding to that sealed position.

In another embodiment, sleeve magnet 34*a* does not move into registry with Hall Effect sensor 115*b* until the sleeve 35*b* has traveled to a position relative to sensing module 100 corresponding to sealing of the patient's ear canal with probe cover 32. In this embodiment, system 20 may deduce that probe cover 32 has sealed the patient's outer ear canal upon detecting a certain (e.g., maximum) flux density output of Hall Effect sensor 115*b*.

If the host sends microcontroller 109 a "convert cold junction thermistor" command (block 322), the microcontroller sets the A/D converter to convert 5 VDC unipolar values at 16-bit resolution, and also controls the A/D converter to make multiplexer 110 select the cold junction thermistor 108 output (block 324). A/D converter 112 converts the thermistor 108 output and provides it to the microcontroller 109 (block 326). Microcontroller 109 provides the sampled thermistor value to base unit 24 (block 308).

If the host sends microcontroller 109 a "convert thermopile" command (block 328), the microcontroller sets the A/D converter to convert 25 millivolt DC bipolar values at 20-bit resolution (this allows the A/D converter to handle situations in which the ambient temperature is either higher or lower than the patient's body temperature). Microcontroller 109 also controls the A/D converter to make multiplexer 110 select the output of thermopile 106 (block 330). A/D converter 112 converts the thermopile 106 output and provides it to the microcontroller 109 (block 332). Microcontroller 109 provides the sampled thermopile value to base unit 24 (block 308).

Figure 15:
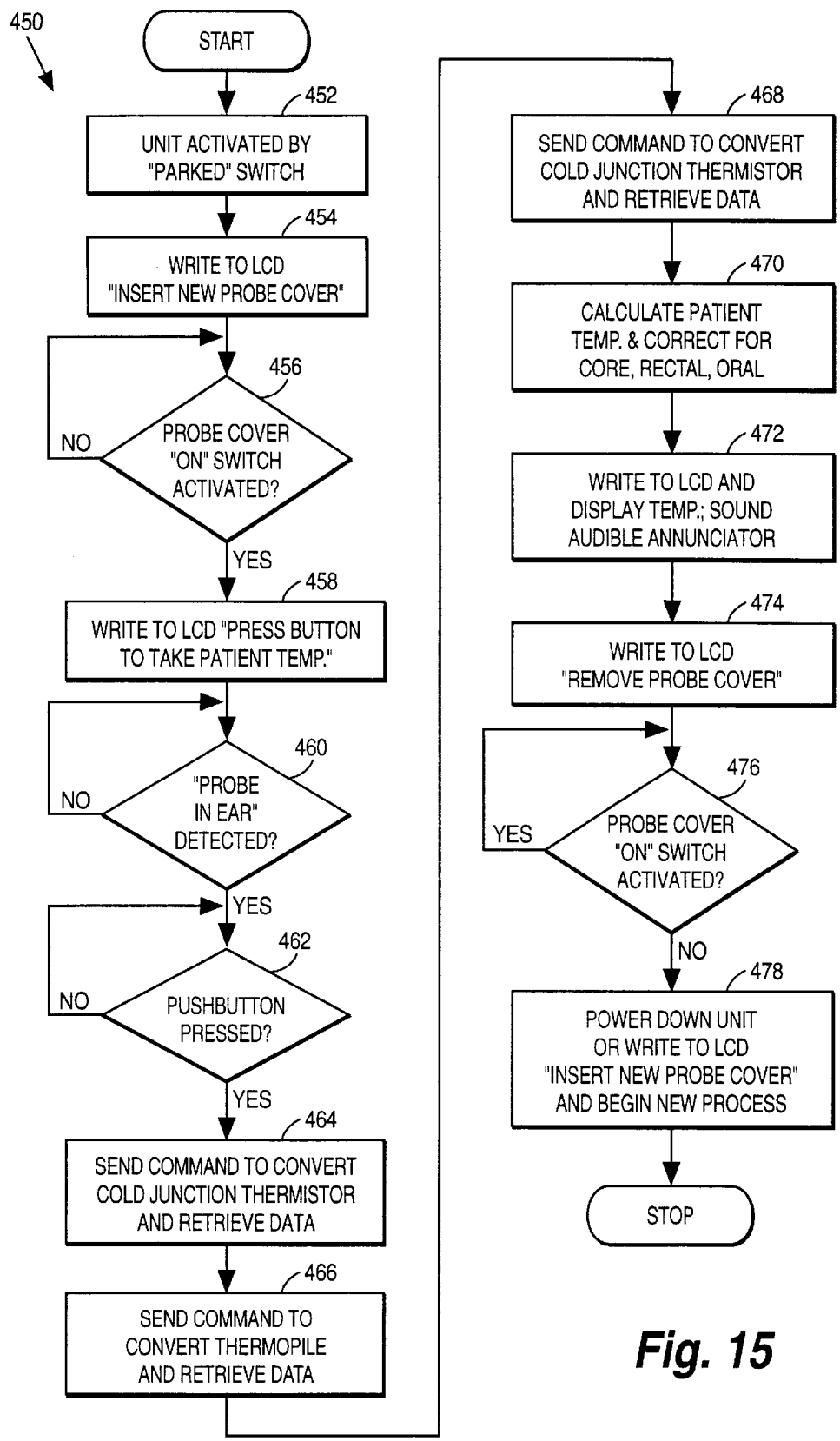
FIG. 15 shows example steps performed by the base unit microcontroller to interact with the sensing module.

FIG. 15 shows an example software routine 450 that base unit microcontroller 402 may perform. In this example, the base unit 24 is activated by removing the measuring unit 22 from its "parked" or storage position—as sensed by sensor 412 (block 452). Microcontroller 402 may then write a message such as "Insert New Probe Cover" to display 26 to remind the clinician to place a new probe cover 32 onto the measuring unit probe end (block 454). Microcontroller 402 then periodically sends a "speculum on/off" status command to the measuring unit 22 and waits for a determination that the clinician has put a probe cover 32 onto the measuring unit (block 456). In this example, microcontroller 402 will not control the system 20 to take a temperature until a new probe cover 32 has been installed—thus discouraging the clinician from using the system in a way that may present risks of cross-contamination.

Once measuring unit 22 informs base unit 24 that a new probe cover 32 is in place ("yes" exit to decision block 456), base unit microcontroller 402 in this example writes the message "Press Button to Take Patient Temperature" to display 26 (block 458). Microcontroller 402 then sends a "Probe in ear status" command to measuring unit 22, and waits for a determination that the measuring unit has been pressed into (and has adequately sealed) the patient's outer ear (block 460). Once this event occurs, microcontroller 402 sends a "push button status" command to the measuring unit 22, and waits for the clinician to press push button 36 (block 462). Upon detecting that button 36 has been depressed, microcontroller 402 commands the base unit 24 to read the cold junction thermistor (block 464), then commands the base unit to read the thermopile (block 466), and then commands the base unit to again read the cold junction thermistor (block 468). In this example, thermistor 108 is read both before and after the thermopile 106 is read in order to determine how much the thermopile cold junction has heated up during the measuring due to the "draw down" effect and physical handling by the clinician (i.e., heat transfer to measuring unit 22 due to proximity to the patient's body and the clinician's hand).

In this example, microcontroller 402 may control measuring unit A/D converter 112 (through microcontroller 109) to read multiple (e.g., 8) samples of the thermopile 106 output in addition to the two thermistor 108 values that "frame", in time, the multiple thermopile values. At the conclusion blocks 464–468, microcontroller 402 has two thermistor output values representing the cold junction temperature of thermopile 106, and eight measurements of the thermopile hot junction. Microcontroller 402 may perform various averaging or other techniques on these multiple measurements to reduce the effects of noise and/or other extraneous factors—deriving accurate and repeatable hot and cold junction digitized values for calculation/conversion into a patient temperature value (block 470). For example, the values may be corrected for body core, rectal and/or oral factors. The temperature can be calculated using mathematical functions, or accessed from a stored database of linearized empirical values collected for each individual thermometer based on laboratory testing that sweeps ambient and "black body" reference target temperature across desired ranges.

In this example, the particular technique used to calculate or derive temperature preferably takes into account the transmissivity of foam probe covers 32 to infrared radiation of particular wavelengths of interest. Probe covers 32 have sufficient uniformity to ensure that accuracy and repeatability are achieved from one probe cover to another.

Once microcontroller 402 has derived patient temperature, it writes the temperature to display 26 and may also control annunciator 406 to generate a sound such as a "beep" or a speech synthesized message (block 472). Microcontroller 402 can then control display 26 to display a "Remove Probe Cover" message (block 474). Microcontroller 402 may then periodically send measuring unit 22 a "speculum on/off status" command, and wait for the clinician to eject the probe cover 32—thus minimizing the risks of cross-contamination by requiring the clinician to dispose of the used probe cover (block 476). In this example, microcontroller 402 can power down system 20 at this point, or it can write a message prompting the clinician to "insert new probe cover" and begin a new measuring cycle (e.g., by repeating blocks 456–476) (block 478).

More Detailed Sensing Module and Base Unit Electronics

Figure 16:
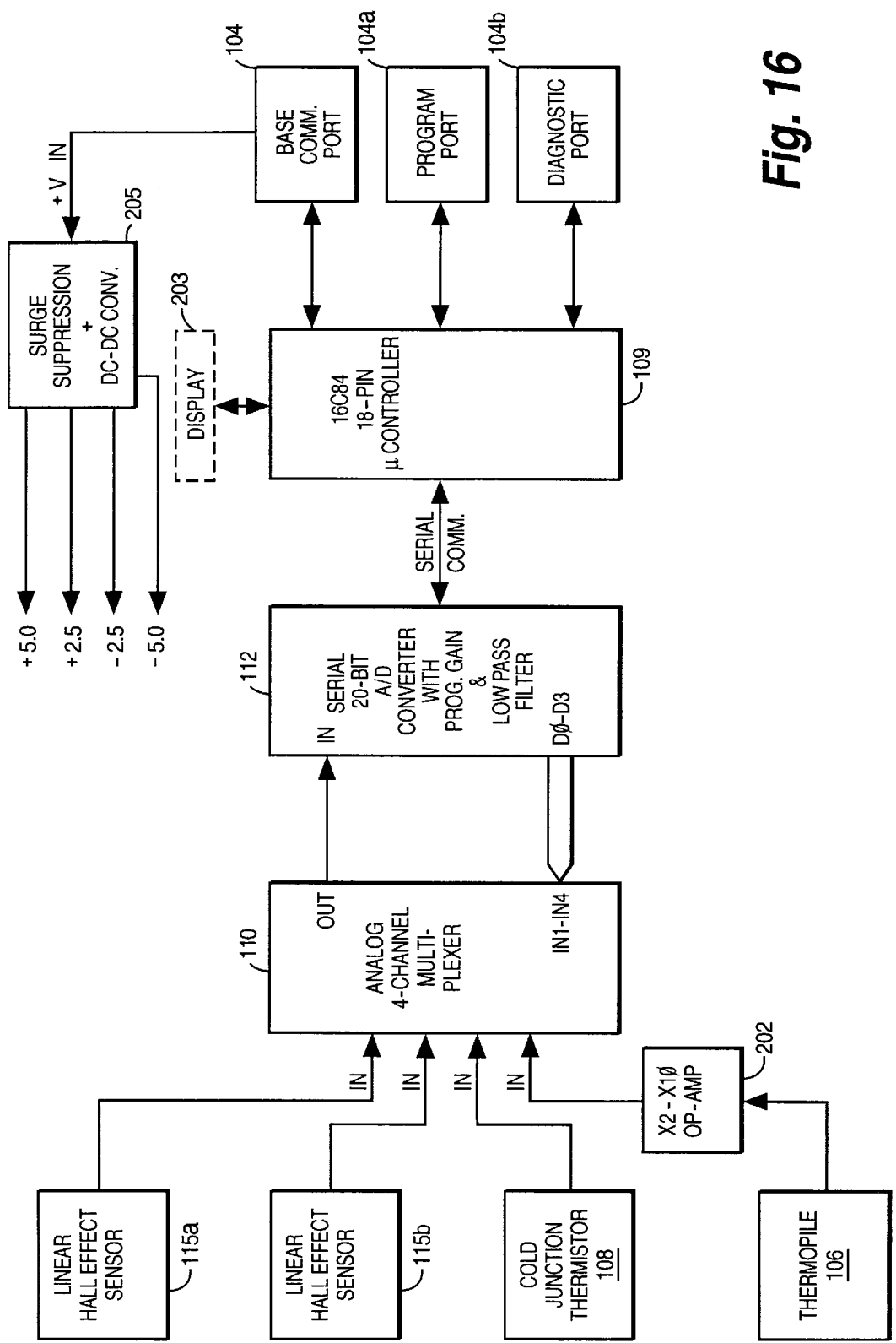
FIG. 16 is a more detailed sensing probe module block diagram.

FIG. 16 shows a more detailed example block diagram of an example circuit arrangement for use in sensing module 100. In this example, the outputs of cold junction thermistor 108, thermopile 106, and a pair of linear Hall Effect magnetic sensors 115a, 115b (one for push button 36, the other for ejection mechanism 34 and force sensing) are connected to separate inputs of an analog 4-channel multiplexer 110. In this example, the signal generated by thermopile 106 is amplified by an amplifier 202 before being input to multiplexer 110. Multiplexer 110 selects one of its four inputs based on a four-bit value the A/D converter 112 sends to the multiplexer's IN1–IN4 input. The multiplexer 110 provides the selected analog output signal on its OUT line to the analog input of the A/D converter 112.

In this example, A/D converter 112 comprises a serial 20-bit A/D converter with programmable gain and low pass filter. The A/D converter 112 converts the analog signal provided by multiplexer 110 to a digital signal with 20-bit resolution, and provides it to microcontroller 109 via a serial communications link. Microcontroller 109 (which in one example comprises a 16C84 18-pin PIC type device) operates under software control to command the operations of the A/D converter 112 (include determining the A/D multiplexer selector output). Microcontroller 109 communicates with base unit 24 (or other host) via base communication port 104 (i.e., a 4-pin modular telephone connector), and may communicate with the same or different host(s) via auxiliary ports/connectors 104a, 104b in this example. Microcontroller 109 may also, as an option, control an LED display 203 to display temperature for example. The measuring unit 22 is energized through a surge and transient protected DC-to-DC converter circuit 205 that produces various different positive and negative DC voltages to power different components within the system.

Figure 17A:
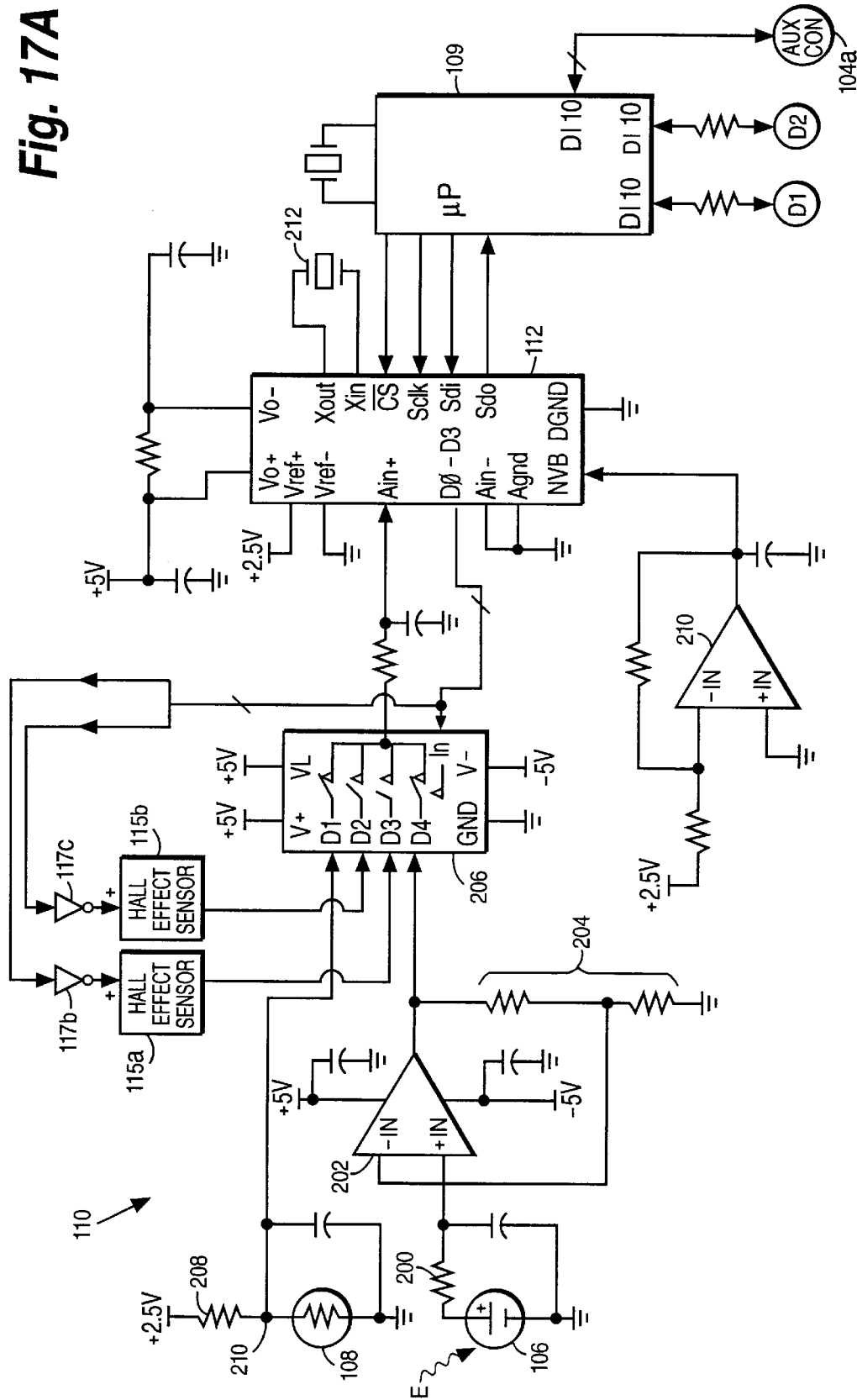
FIGS. 17A and 17B show an example sensing probe module and power supply schematic diagrams.
Figure 17B:
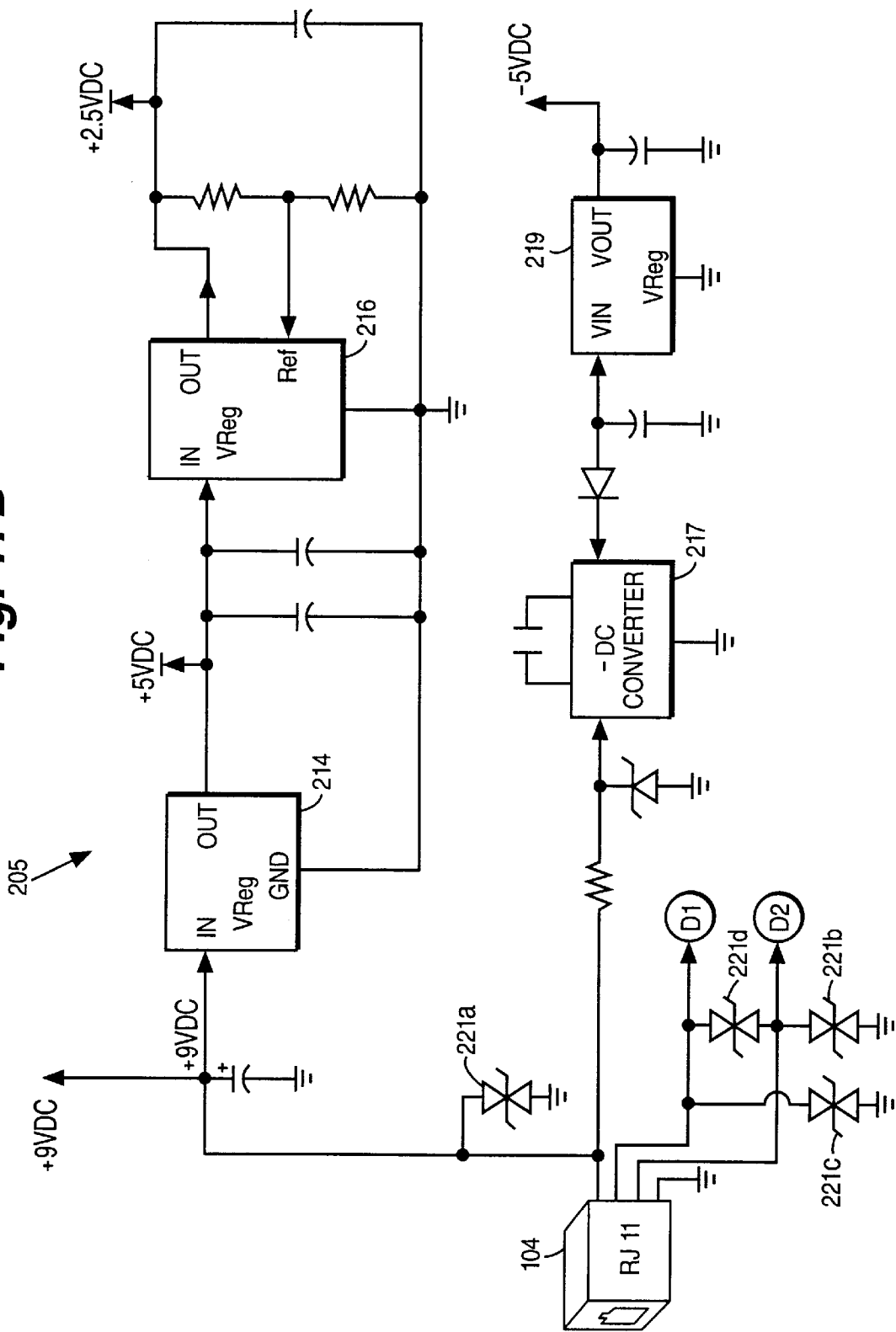

FIGS. 17A and 17B show a more detailed electrical embodiment for use in the preferred sensor module 100. Referring to FIG. 8A, infrared electromagnetic energy E impinges upon thermopile 106, which is connected via a resistor 200 to the non-inverting input (+) of operational amplifier 202. The inverting (−) input of op amp 202 may be coupled in a feed back loop to the op amp output via voltage divider 204. The gain of op amp 202 is set by appropriate selection of resistor values within voltage divider 204 to provide an appropriate gain that optimizes the dynamic range of A/D converter 112. This gain may be set in the range of between 2 and 10 for example, depending upon empirical test results based on the particular type of thermopile 106 and other factors.

The output of op amp 202 is connected to the normally open (NO) input of analog multiplexer 206. Thermistor 108 (which in the preferred embodiment is disposed within the thermopile 106 can and is closely thermally coupled to the thermopile cold junction) is connected in a voltage divider configuration in series with resistor 208—the summing point 210 of the voltage divider being connected to the normally closed (NC) input of analog multiplexer 206. Analog multiplexer 206 can select between the op amp 202 output and the thermistor 108 voltage based on the selection signal applied to the multiplexer's appropriate input. The microcontroller 109, through a setup configuration, determines the data output states of A/D converter 112 for controlling selection of the multiplexer 206 input.

In a further embodiment, an analog switch (not shown) can be used to temporarily short out thermopile 106 to allow for total system calibration. The analog switch can simply be another channel of analog multiplexer 206.

The multiplexer 206 can also select either of Hall Effect sensors 115a, 115b for digitizing by the A/D converter 112. If one of the Hall Effect sensors is selected, the decoder outputs a logic level 0 signal to a corresponding inverter (or plural inverters) 117b, 117c. Inverters 117b, 117c provide a TTL level signal (with sufficient current) to power the Hall Effect sensor 115 being measured. Power is saved by powering the sensor 115 only when its output is being selected by the multiplexer 206.

In this example, Hall Effect sensors 115a, 115b may each comprise an off the shelf linear Hall Effect sensor integrated circuit (e.g., manufactured by ITT, Panasonic or others). Linear Hall Effect sensors 115a, 115b have outputs that provide an analog voltage that corresponds to the magnetic flux density, with the voltage swing around 2.5V depending on the pole of the magnet being sensed (V1<V2 for south magnetic pole, V1>V2 for north magnetic pole). Use of linear Hall Effect sensors 115a, 115b eliminate the need for tight mechanical and magnetic tolerances for threshold activation of the Hall Effect sensors, and also provide a system that will tolerate magnetic pole reversals, decreasing the manufacturing burden for magnetic polarity compliance.

The output of analog multiplexer 206 is connected to an analog input (Ain+) of A/D converter 112. In this example, A/D converter 112 includes a x20 preamplifier and a digital low pass filter. The differential Ain− input of A/D converter 112 is tied to ground potential. The voltage reference $V_{ref}$+of A/D converter 112 in this example is tied to a regulated +2.5 VDC. The output of an op amp 210 is applied to the negative voltage bias (NVB) input of A/D converter 112—allowing the A/D converter to measure bipolar (positive or negative) voltages. Inverter op amp 210 provides a negative bias into the NVB input of A/D converter 112, allowing the A/D converter 112 to operate in a bipolar mode (i.e., swing negative on the input). This allows sensing module 100 to accommodate ambient temperatures that are higher than the patient temperature (under such circumstances, the output of thermopile 106 will swing negative rather than positive).

A crystal 212 (e.g., 32.768 or other convenient frequency) is connected to the crystal input and output connections of A/D converter 112. A serial clock input $S_{clk}$ is used to drive data transfers to/from A/D converter 112 with configuration data being serially transferred into the A/D converter via the $S_{di}$ line and measurement data being serially transferred out of the A/D converter via the $S_{do}$ line. A/D converter 112 communicates with microcontroller 109 via these serial lines.

In this example, microcomputer 109 provides tasking for sensing probe cover position, activation via push button 36, controlling the A/D converter 112 (sampling and averaging), etc. Placing microcontroller 109 within sensing module 109 allows all communications with the host (i.e., base unit 24) to take place over the 4-wire handset cord, and relieves the host from having to manage the A/D conversion process. In this example, microcontroller 109 has on board programmable EEPROM or flash RAM that allows the host to change the programming within the microcontroller via an auxiliary programming connector 104a. Such programming features allow sensing module 100 to be reprogrammed easily to accommodate program changes, bug fixes or to work with a variety of different hosts.

In this example, sensor module 100 includes an onboard voltage regulator arrangement 205 shown in FIG. 8B. Onboard voltage regulators 214, 216, for example, regulate +9 VDC power supply voltage down to ±5 VDC and +2.5 VDC. In this example, regulators 214, 216 regulate the +9 VDC power input via connector 104 down to +5 VDC and +2.5 VDC, respectively. Appropriate filter capacitors are provided to ensure good regulation and to minimize power supply noise. A DC-to-DC converter 219 converts the +9 VDC voltage to a negative voltage, which is regulated down to −5 VDC by a negative voltage regulator 219. Surge protectors 221 are used to protect sensing module 100 against surges coupled to connector 104.

Figure 18:
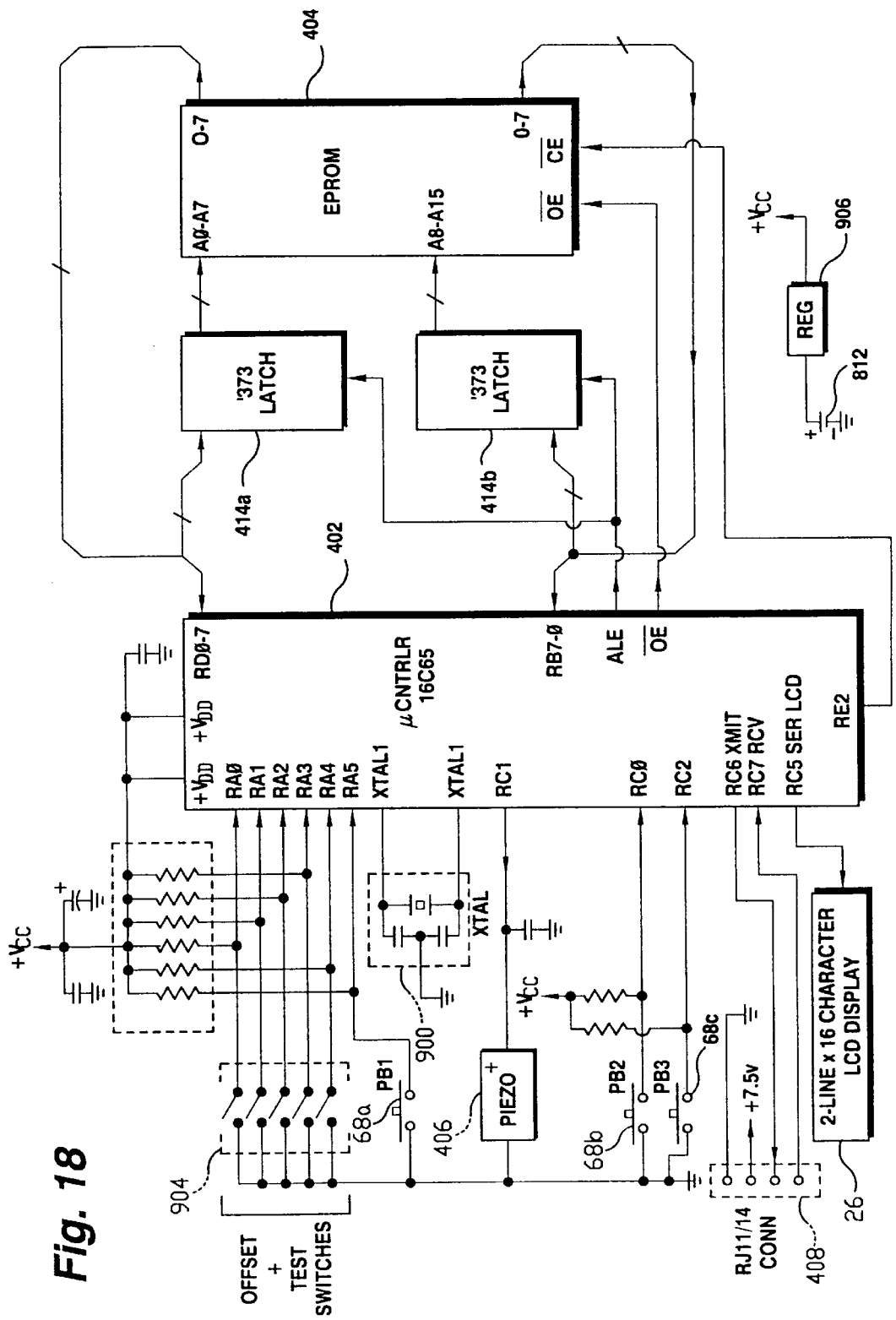
FIG. 18 shows a detailed example base unit schematic diagram.

FIG. 18 shows an example more detailed schematic diagram of the electronic circuitry within base unit 24. As shown in FIG. 18, microcontroller 402 in this example comprises a Motorola 16C65 microcontroller driven by a crystal 900. Memory module 404 in this example, comprise a 64 K by eight EPROM coupled to microcontroller 402 by a pair of address buffer/latches 414a, 414b. Offset and test switches 904 coupled to one of the I/O ports of microcontroller 402 allow field programming using DIP switch selection. Push buttons 68 may be coupled to the same input port to allow microcontroller 402 to read the state of these switches. RJ-11/14 connection 408 includes power and ground pins in serial input and output pins coupled directly, in this example, to input/output pins of microcontroller 402 which act as serial input/output ports. A regulator 906 is provided to regulate the power from batter pack 812.

Example Single Unit Embodiment

Figure 19:
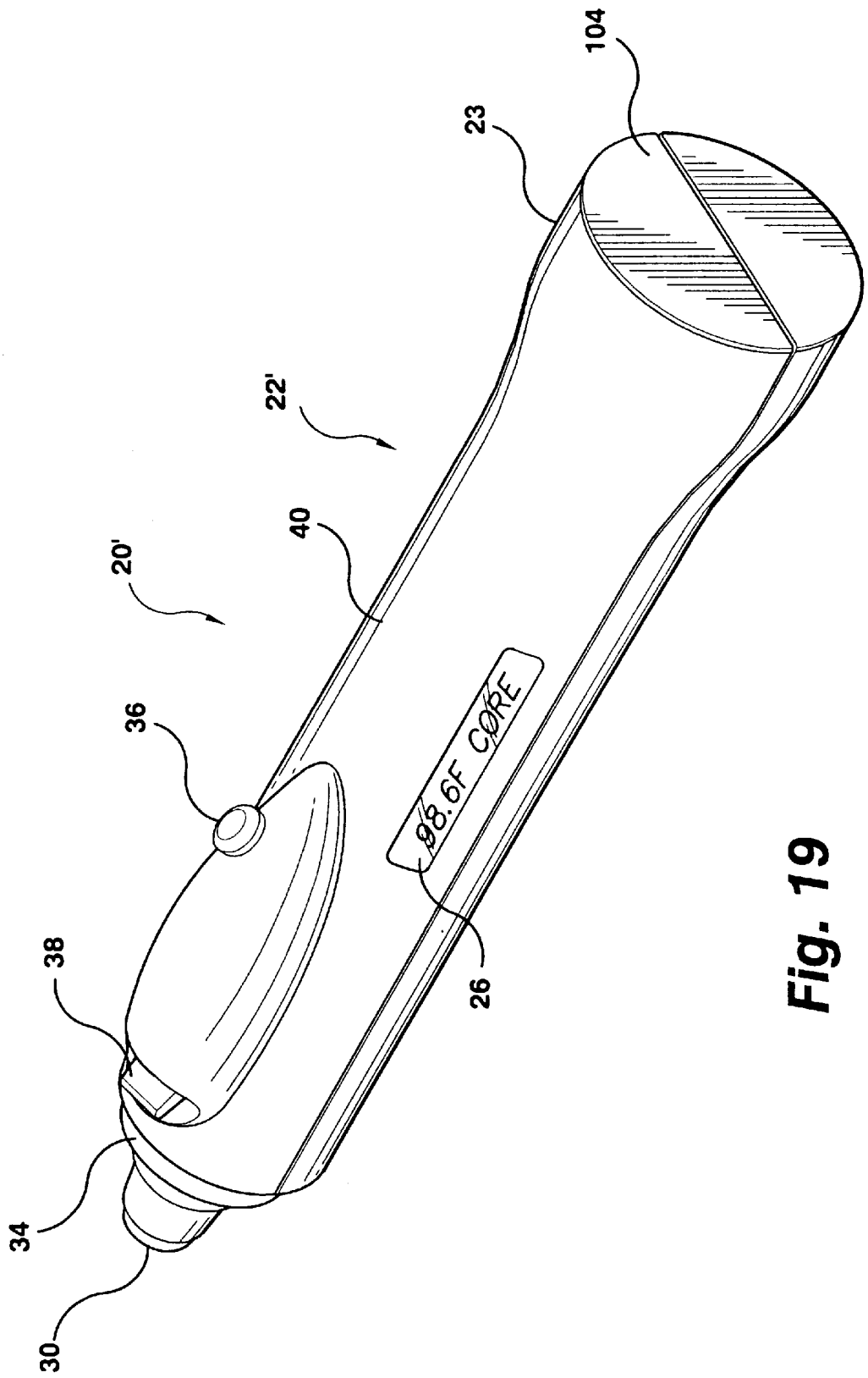
FIG. 19 shows an example unitary one-piece thermometer.

FIG. 19 shows a further embodiment of a temperature measuring system 20' comprising a unitary handheld unit including an integral display 26. In this example, miniature display 26 may be mounted directly to sensing unit housing 40 to provide integral temperature display. All of the temperature processing functions described above as being performed by base unit 24 are performed in this example by the microcontroller 109 within measuring unit 22. A programming port (not shown) may be provided if desired to dynamically load calibration or other information into the measuring unit 22. In addition, a small rechargeable battery may be disposed within measuring unit 22', providing power for the measuring unit without need to connect it to a base unit 24. The battery pack could mate with the lower portion of housing 40 (the end away from tip 30) as in certain cellular phone designs to provide an easily replaceable battery pack module that can be recharged in a recharging fixture of conventional design.

Figure 20B:
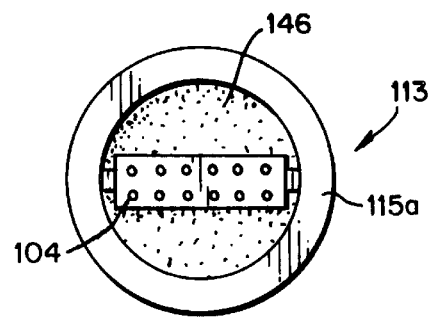
FIGS. 20A–20C show a further example sensing probe module.
Figure 20C:
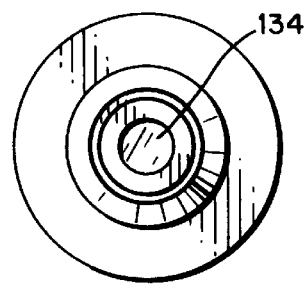
Figure 20A:
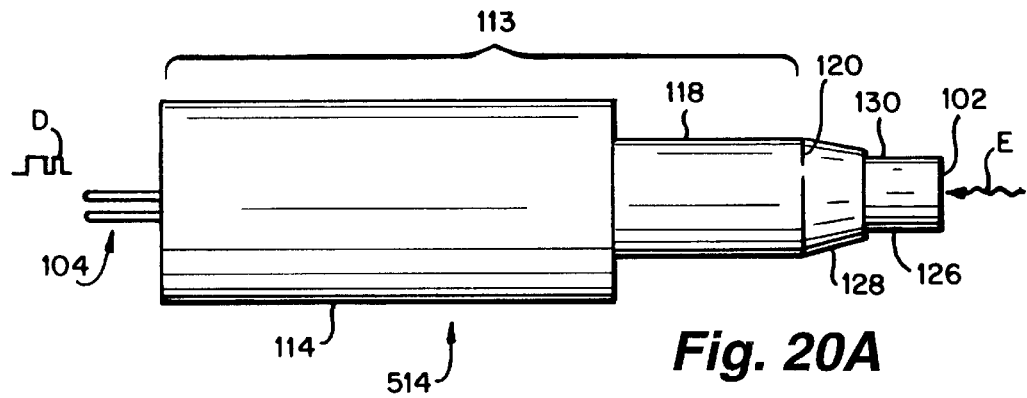
Figure 22A:
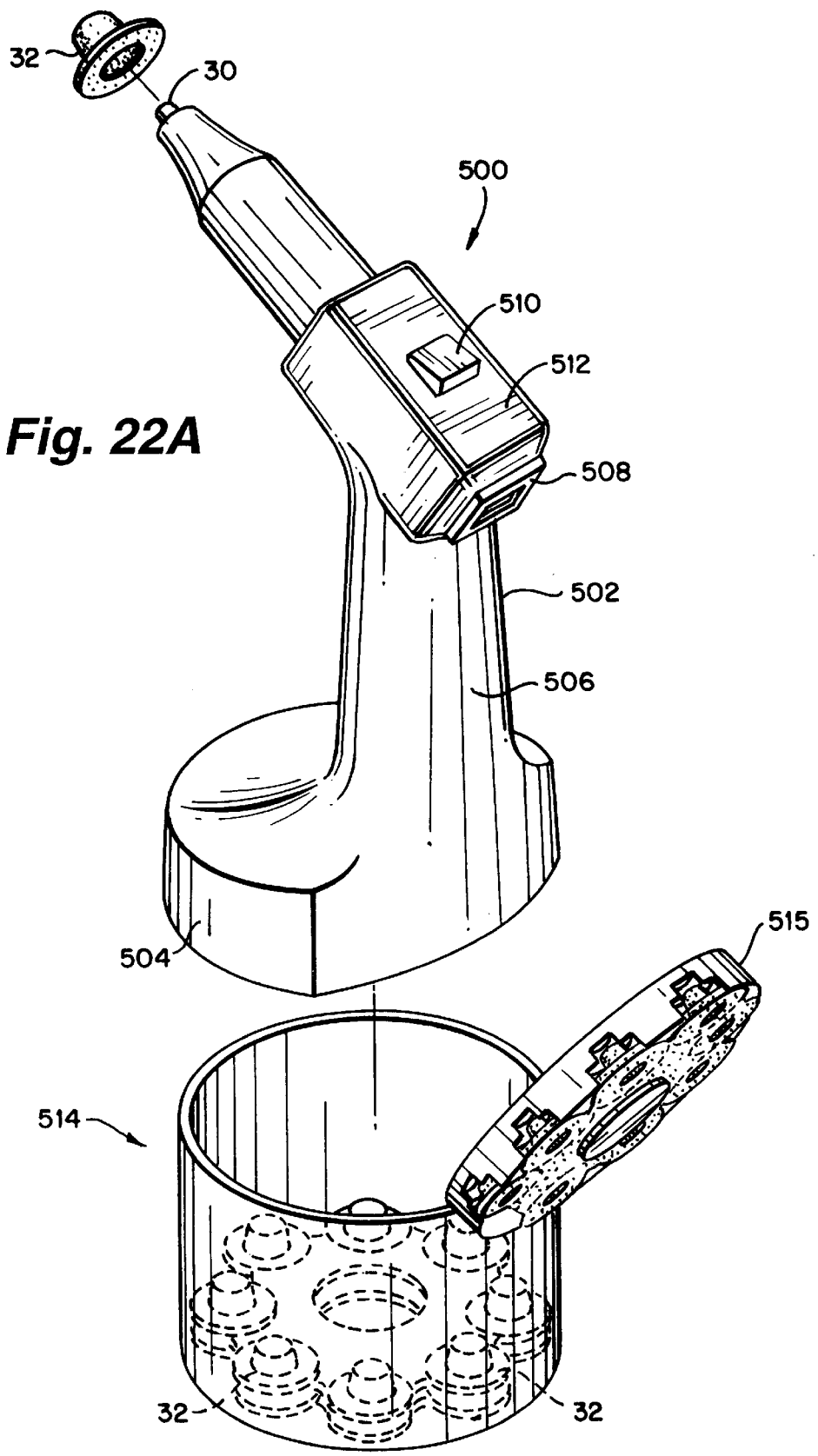
Figure 22B:
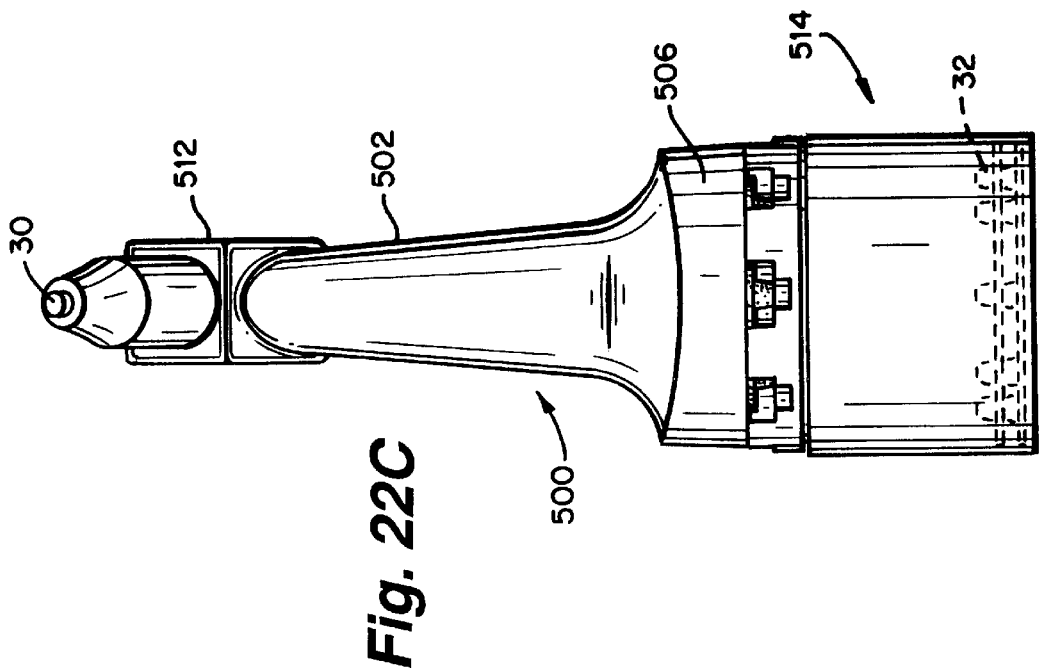
Figure 22C:
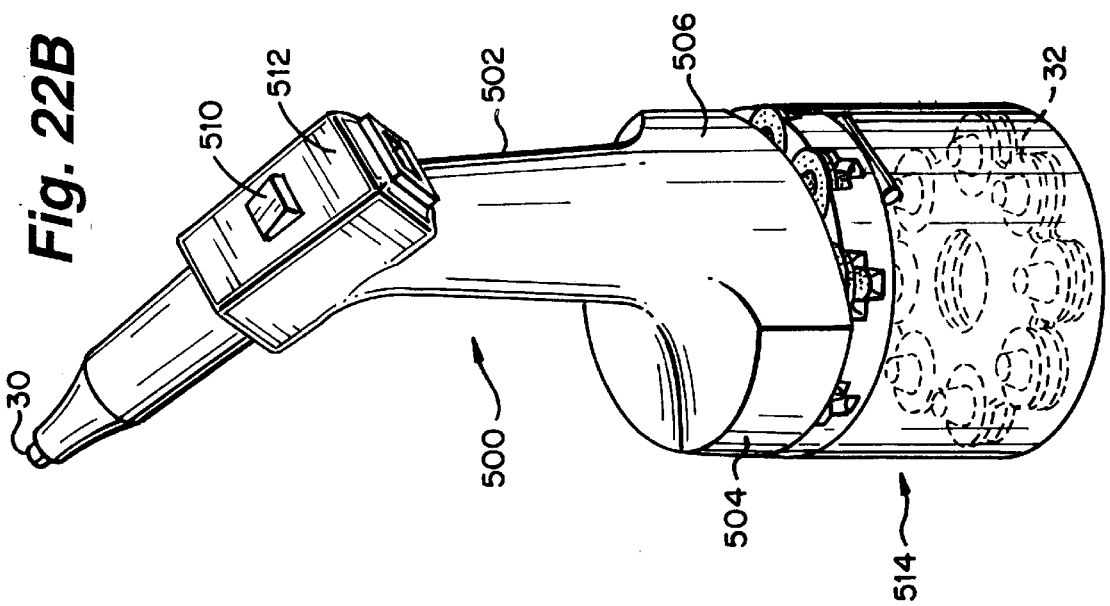

The system 22' shown in FIG. 19 may include a sensing module 514 shown in FIGS. 20A–20C. Sensing module 514 may be similar to the one shown in FIGS. 5–7 except that it can be more compact (i.e., shorter) because the internal microcontroller 109, Hall Effect sensors 115 and/or RJ-11 modular jack can be eliminated if desired to save space and expense.

Example Further Ejection Mechanism Embodiment

FIGS. 21A–21B show a variation in the ejection mechanism shown in FIGS. 9A–9B. FIG. 21A shows ejection mechanism 34' in a retracted (latched) position, and FIG. 21B shows the ejection mechanism in an unretracted (unlatched) position. In this example, a spring 135a biases probe cover sleeve 135b toward probe end 30. Probe cover sleeve 135b has, at its distal end, a substantially planar and circular plateau-like surface 321A that is specially adapted to interface with a flat base portion of a disposable foam-based probe cover 32 (see above-referenced Cheslock et al patent applications). The probe cover 32 base portion pushes on the sleeve surface 321A upon installing the probe cover onto the probe end 30. The probe cover 32 frictionally engages and stretches around the probe cover end 30—so that the probe cover is retained on the measuring unit 22 during temperature measurement.

To install a probe cover 32 onto the measuring unit 22, the clinician places a probe cover 32 onto the probe end 30 and pushes the probe end into the probe cover. The outer diameter of probe end 30 is made so that it is slightly larger than the unstretched inner diameter of the probe cover 32. Therefore, as the probe end 30 is inserted into the probe cover 32, the probe cover stretches around the probe end— frictionally engaging the probe end. As the probe end 30 is further inserted into the probe cover 32, the probe cover base portion contacts the sleeve plateau surface 321A. Further pressure from the probe cover 32 (e.g., via a seating structure) allows the probe cover plateau surface 321A to exert a force on sleeve plateau surface 321A—overcoming the biasing force of spring 135a and causing the sleeve 135b moves away from the probe end.

As sleeve 135b moves away from probe end 30 and toward the other end of the measuring unit 22, a catch 135e disposed on an arm 135z that extends from sleeve 135b catches on a projection 135d extending from a pivoting latching mechanism 135c. Latching mechanism 135c may be molded as part of button 38, and may pivot about a pivot point 135f. A spring 135g (which may be made of plastic and molded as part of button 38) biases the latching mechanism 135c in a clockwise direction about the pivot point 135f. The interaction between catch 135e and projection 135d retains the sleeve in a retracted position under the biasing force of spring 135a. A spring 135g thus biases projection 135d in catching contact with sleeve catch 135e.

In this example, sleeve 135b is capable of a slight overtravel rearwardly from projection 135d (i.e., toward the right as shown in FIG. 21A) from latched position as the clinician presses probe end 30 (covered with a probe cover) into the patient's outer ear. In this example, sleeve 135b can overtravel until it comes into contact with a stopping surface 321B defined in the outer housing of sensing module 100. In one example, magnet 34'a is in registry with magnetic sensor 115 when ejection mechanism is in the FIG. 21A latched position. In another example, the embedded magnet 34'a moves into registry with magnetic sensor 115 when the sleeve 135b is in its overtravel position (i.e., when the instrument has sealed the patient's outer ear). An additional spring and associated structure(s) may be provided for the if the force of latching spring 135a is high enough to exert an uncomfortably large force on the patient's outer ear.

As described herein, sensing module 100 can sense the position of a magnet 34'a embedded within sleeve 135b to determine whether the sleeve 135b is in the position shown in FIG. 21A or whether it has overtraveled. Thus, sensing module 100 can magnetically determine whether the probe cover 32 is in place (based on the assumption that the clinician will not push back sleeve 135b into the latched position shown in FIG. 21A without first placing a probe cover 32 on the measuring unit), and whether the clinician has inserted the probe end 30 (and the probe cover 32 that covers it) into the patient's ear. This position sensing can be used, if desired, to set conditions for and/or prompt to take a temperature.

Upon removing the probe end 30 from the outer ear, sleeve 135b returns from the over-traveled position to the FIG. 21A latched position—spring 135g biasing structure 135e about pivot 135f in a way that ensures that project 135d acts as a stop catch 135e and thus for sleeve 135b. In this way, sleeve 135b does not immediately strip a probe cover 32 from probe end 30 upon removing the probe end from the patient's ear.

In this example, depressing button 38 causes latching mechanism 135c to pivot downward about pivot 135f— releasing projection 135d from catch 135e and allowing sleeve 135b to slide forward under the force of spring 135a—thus stripping probe cover 32 from probe end 30. The stripping action occurs by the biasing force of spring 135a overcoming the frictional force that the probe cover 32 inner foam surface exerts on the probe end outer cylindrical surface 30', as the sleeve plateau surface 321A presses outwardly against the probe cover flat base portion. The biasing force exerted by spring 135a is sufficient to cause the probe cover 32 to automatically fly off into a waste receptacle such as a wastepaper basket when the clinician manually lifts fingerpull 38. As mentioned above, plastic spring 135g biases latching mechanism 135c upwardly (i.e., in a clockwise direction relative to pivot 135f) to keep projection 135d in contact with catch 135e except when button 38 is depressed.

Example Gun-Shaped Embodiment

Figure 12A:
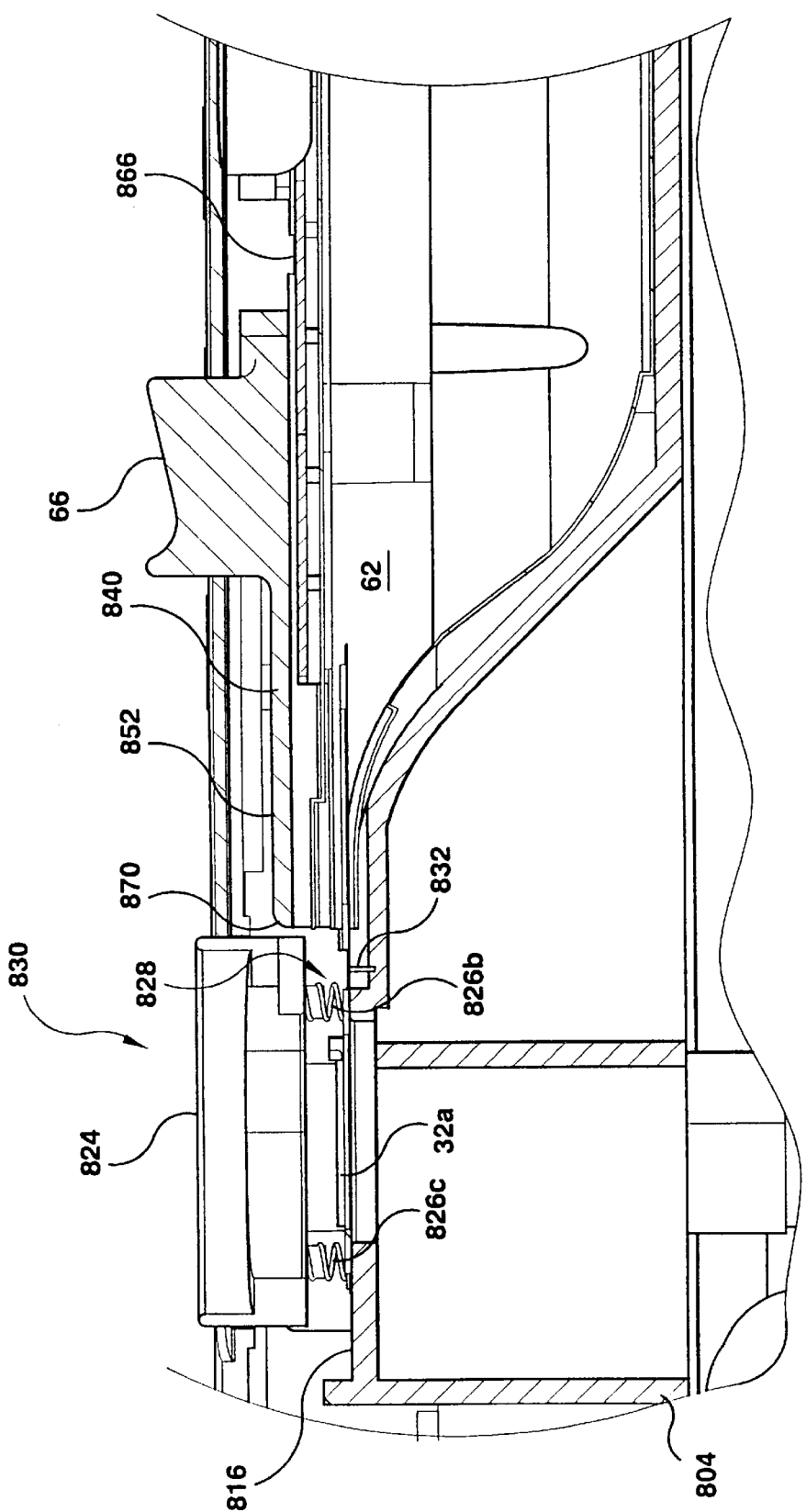
FIG. 12A is a cross-sectional view of the example base unit probe cover dispensing structure shown in FIG. 12.

FIGS. 22A–22E show a further embodiment of a tympanic measuring system 500 provided in accordance with the present inventions. Example system 500 includes a self-standing main unit 502 including a base portion 504 that can be placed on a table top or other support surface. The clinician grasps a gripping portion 506, and may actuate the unit by depressing button 508. Button 508 may include a display area, so that system 500 can display temperature on the front surface of button 508. If desired, self-standing main unit 502 can mate with a corresponding probe cover dispenser 514 that dispenses probe covers 32 for use with the system. Probe cover dispenser 514 may include a removable cap 515 that allows the clinician to access probe covers 32 stored within the dispenser. As shown in FIG. 12A, probe covers 32 may be fabricated in a cluster to allow easy handling. Dispenser cap 515 may accept such a cluster, and may include one or a number of molded probe cover seats to allow easy installation of a probe cover onto the thermometer probe end 30 (see below).

The electrical components shown in FIG. 10 may be included within a central housing portion 512 of system 500, and the system may include a sensing module 514 shown in FIGS. 20A–20C.

Figure 23:
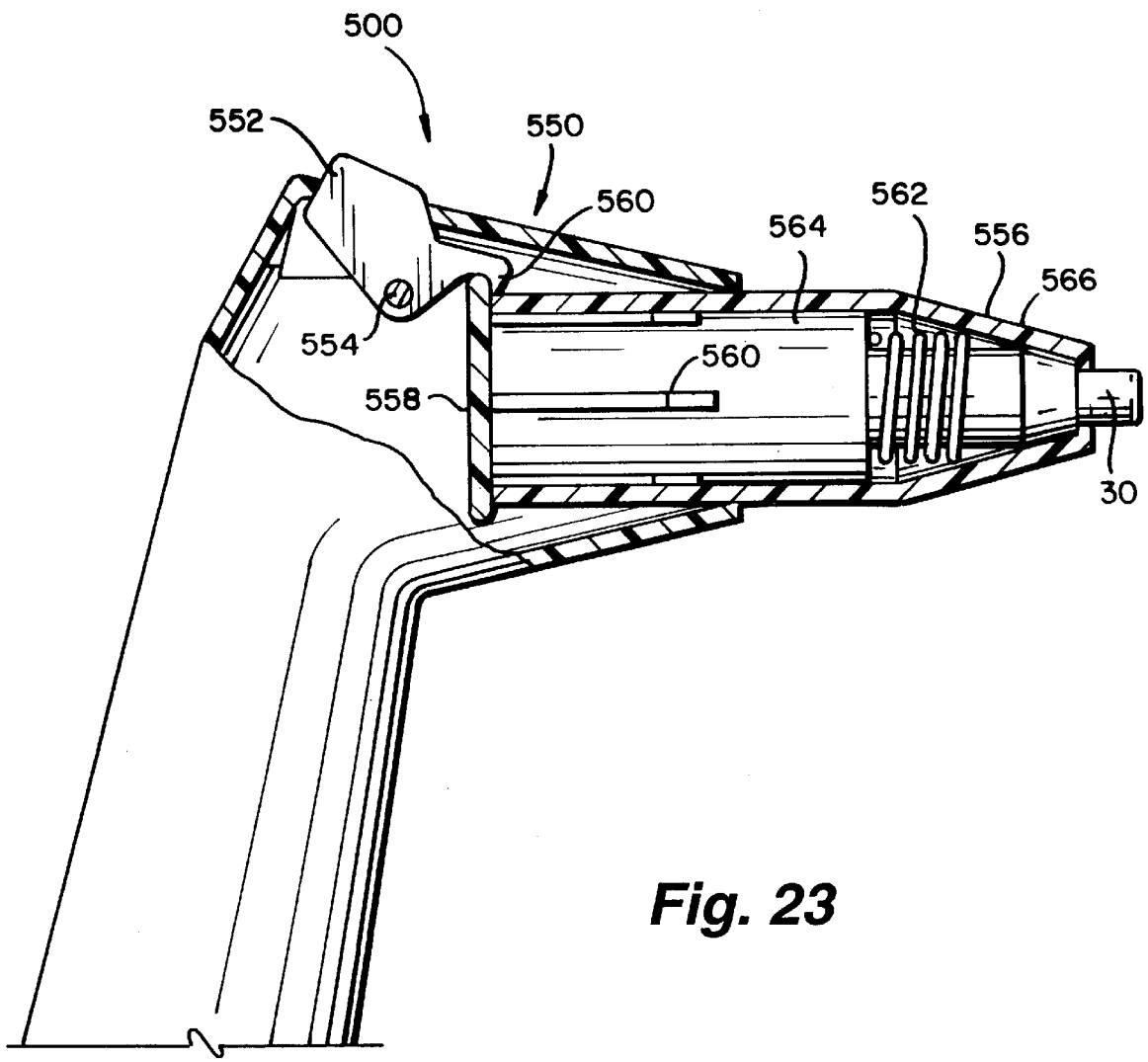
FIGS. 23–23B show an example probe cover ejection mechanism for the FIG. 22A–22E embodiment.
Figure 23A:
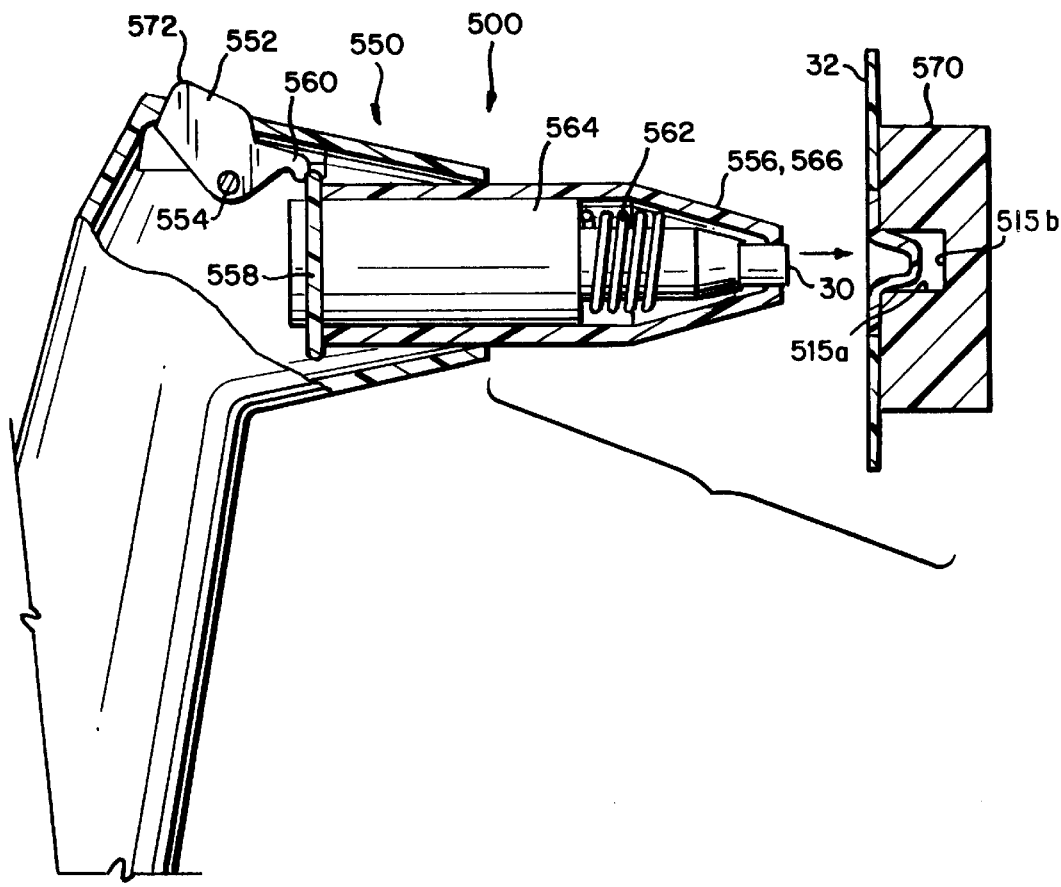
Figure 23B:
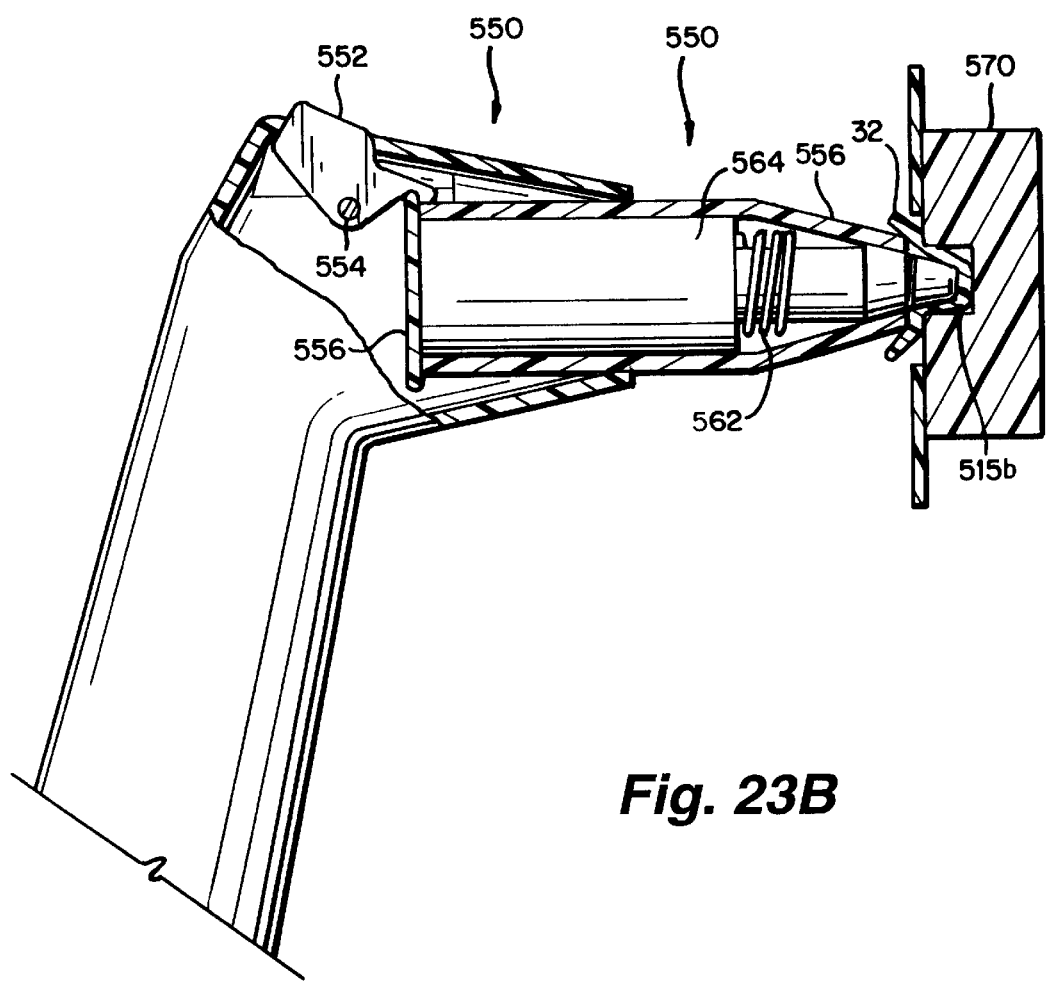

FIGS. 23, 23A and 23B show an example ejection mechanism 550 for the gun-shaped embodiment of FIGS. 22A–22E. Ejection mechanism 550 in this example includes a catch 552 mounted on a pivot 554. The catch 552 defines a button portion 572 and a hook 560. A torsion spring (not shown) is provided at pivot 554 biases the catch 552 downwardly (i.e., in a clockwise direction relative to the pivot).

A cylindrical ejection sleeve 556 is disposed around a cylindrical housing portion 564 of thermometer 500. Ejection sleeve 556 includes a grabbing portion 558 that can be grabbed and retained by a catch hook 560. A spring 562 disposed between the thermometer housing portion 564 and a sleeve conical end portion 566 biases the sleeve toward the sensing module probe end 30. Tracking structures 560 defined in housing portion 564 interact with grooves (not shown) defined within sleeve grabbing portion 558 to prevent the sleeve 556 from rotating relative to the housing portion 564.

FIG. 23 shows ejection mechanism 550 in a latched, retracted position but without a probe cover 32 installed. Normally, ejection mechanism 550 assumes this latched, retracted position when a probe cover 32 is disposed on the thermometer 500. Referring to FIG. 14A, ejection mechanism 550 is initially in an unretracted position. To install a probe cover 32 onto thermometer 500, the clinician typically inserts the probe cover into a seat 570. Seat 570 may be molded on plastic dispenser lid 515 for example (see FIG. 12A).

The clinician then presses the probe end 30 into the probe cover and associated seat opening 515a. Under this force, the probe end 30 and ejector sleeve 556 are pushed into the probe cover 32 and continue to move through seat 515 until the probe cover and the probe end strike the bottom stop 515b (see FIG. 14B). The seat 515 is designed so that it allows the probe end 30 and the probe cover 32 to pass, but it interferes with the ejection sleeve 556. During the course of the movement of the probe end 30 and probe cover 32 into the seat 515, the ejection sleeve 556 is moved back, loads the spring 562, and is retained by catch hook 560 (catch 552 now being in a cocked position).

When the clinician is finished taking a temperature, he or she presses catch button portion 572. This pressing action causes catch 552 to pivot in a counter-clockwise direction against the bias of the pivot torsion spring, allowing it to release sleeve 556. This action unloads spring 562, producing a forward movement of the ejection sleeve 556 and stripping the probe cover 32 from probe end 30.

While the invention has been described in connection with what is presently considered to be the most practical and preferred embodiment, it is to be understood that the invention is not to be limited to the disclosed embodiment, but on the contrary, is intended to cover various modifications and equivalent arrangements.

We claim:

1. A method of operating a tympanic thermometer comprising:

biasing a probe having a tip to a forward position relative to a housing;

inserting the probe tip into a patient's outer ear canal;

applying pressure to said housing in order to seal the patient's outer ear canal with the probe, the applied pressure forcing the probe to move rearwardly in said housing against the bias and forcing the probe tip further into said patient's outer ear canal;

measuring said rearward probe displacement relative to said housing; and comparing said measured rearward probe displacement to a predetermined threshold to determine when the probe tip has sealed the patient's outer ear canal.

2. A method as in claim 1 further including automatically taking a temperature measurement in response to said comparing step.

3. A method as in claim 1 further including inhibiting taking of a temperature measurement in response to said comparing step.

4. An ear thermometer comprising:

a modular sensing probe including a probe casing defining a cavity therein, and electronics disposed within said cavity, said electronics including at least an infrared sensor and a temperature sensor, said infrared sensor having a cold junction, said temperature sensor measuring the temperature of said infrared sensor cold junction, and a base unit electrically coupled to said modular sensing probe, said base unit including at least one pluggable memory device, wherein said base unit can be interchangeably used with any of plural said modular sensing probes upon installation into said base unit of a pluggable memory device containing information specific to said modular sensing probe.

5. An ear thermometer as in claim 4, further including a standard telephone handset cord and associated RJ-11 connectors for electrically coupling said base unit to said modular sensing probe.

6. An ear thermometer as in claim 4, wherein said modular sensing probe further includes a field-replaceable waveguide or filter.

7. An ear thermometer as in claim 4, wherein said modular sensing probe further includes a field-replaceable optical lens.

8. An ear thermometer as in claim 4, wherein said modular sensing probe further includes a field-replaceable probe tip.

9. An ear thermometer kit including:

a sensor module comprising an infrared sensor having a cold junction, a tip mounting structure optically coupled to said infrared sensor, a temperature sensor thermally coupled to said cold junction, and electronics coupled to said infrared sensor and said temperature sensor, said electronics determining a patient's temperature in response to outputs from said infrared sensor and said temperature sensor;

a first replaceable probe tip defining a first form factor that is specially adapted to accept a first disposable probe cover type; and a second replaceable probe tip defining a second form factor different from said first form factor, said second form factor being specially adapted to accept a second disposable probe cover type, wherein either of said first or second probe tips can be coupled to said tip mounting structure and said infrared sensor.

10. A probe cover dispenser comprising:

an advance mechanism including gripping means for gripping a probe cover and moving it onto an insertion platform, said insertion platform defining an orifice therein; and a clamp that clamps at least a portion of said probe cover to said insertion platform under application of pressure of a tympanic thermometer probe being inserted into said probe cover.

11. A probe cover dispensing mechanism as in claim 10, further including a cutting arrangement that automatically cuts said probe cover from a strip of connected probe covers.

12. A probe cover dispensing mechanism as in claim 10, wherein said clamp includes a structure that moves further structure associated with said tympanic thermometer probe from an unretracted position to a retracted position.

13. A probe cover dispensing mechanism as in claim 10, wherein said probe cover dispensing mechanism is adapted to receive and dispense probe covers from a cartridge.

14. A probe cover dispensing mechanism comprising:

a frame member; and a ring member suspended above said frame member in a first position, said ring member being movable from said first position to a second position, said ring member in said first position allowing a disposable probe cover to slide beneath it, said ring member in said second position clamping at least a portion of said disposable probe cover to said frame member.

15. A probe cover dispensing mechanism as in claim 14, wherein said frame member has a cutting blade disposed therein, and said ring member causes said probe cover to be cut by said cutting blade when pressed toward said second position.

16. A probe cover ejection mechanism for use with a tympanic thermometer of the type that accepts disposable probe covers thereon, said probe cover ejection mechanism comprising:

an ejection sleeve moveable between a retracted position and a further position, said ejection sleeve including a stripping ring disposed thereon, said stripping ring, in use, stripping a disposable probe cover from said tympanic thermometer when said ejection sleeve moves from said retracted position to said further position;

a biasing spring coupled to said ejection sleeve, said biasing spring urging said ejection sleeve toward said further position; and a catch mechanism pivotable between a locking position and a release position, said catch mechanism retaining said ejection sleeve in said retracted position against the urging of said biasing spring when in said locking position, said catch mechanism allowing said ejection sleeve to move to said further position when in said release position.

17. A method for using an infrared sensing probe to measure a patient's temperature through the patient's ear canal while accounting for the heat loss from the patient's ear canal, said method comprising:

quantifying the amount of pressure the sensing probe applies to the patient's ear canal; and correcting a measured temperature based at least in part on said quantified amount of pressure.

18. A method as in claim 17, further including:

measuring or estimating the amount of time the sensing probe has been in surface contact with the patient; and wherein said correcting step comprises developing an offset based on said quantity, and said time amount.

19. A method as in claim 17, wherein said correcting step includes correcting said measured temperature based on known thermal characteristics of said probe.

20. A method as in claim 17, further including measuring the time differential between successive temperature measurements, and said correcting step includes correcting said measured temperature based on said measured time differential.

21. A method as in claim 17, wherein said correcting step includes the step of developing said correction further based on empirical data concerning the vascular thermal recovery time of the patient's ear canal.

22. A method as in claim 17, wherein said correcting step includes the step of developing said correction further based on empirical data concerning the surface contact area between the probe and patient's external acoustic meatus.

* * * * *